(12) United States Patent
Van Nocker et al.

(10) Patent No.: US 7,365,182 B2
(45) Date of Patent: Apr. 29, 2008

(54) **PLANT *VERNALIZATION INDEPENDENCE* (VIP) GENES, PROTEINS, AND METHODS OF USE**

(75) Inventors: Steven R. Van Nocker, East Lansing, MI (US); Hua Zhang, Holt, MI (US)

(73) Assignee: Michigan State University, Lansing, MI (US)

( * ) Notice: Subject to any disclaimer, the term of this patent is extended or adjusted under 35 U.S.C. 154(b) by 192 days.

(21) Appl. No.: 10/427,224

(22) Filed: May 1, 2003

(65) Prior Publication Data

US 2004/0033607 A1    Feb. 19, 2004

Related U.S. Application Data

(60) Provisional application No. 60/376,765, filed on May 1, 2002.

(51) Int. Cl.
*C12N 15/29* (2006.01)

(52) U.S. Cl. .................................................. 536/23.6

(58) Field of Classification Search .............. 536/23.1, 536/23.6, 24.1; 800/278, 287, 298, 290; 435/252.3, 419, 468
See application file for complete search history.

(56) References Cited

U.S. PATENT DOCUMENTS 6,492,575 B1 * 12/2002 Wagner et al. ................ 800/25

OTHER PUBLICATIONS

Zhang et al (2002, The Plant Journal 31(5):663-673).*
Bowie et al, Science 247:1306-1310, 1990.*
McConnell et al, Nature 411 (6838):709-713, 2001.*
Beven et al (1999, NCBI Accession No. ATF27B13).*
Smith et al. (1999) Trends Biochem Sci 24, 181-185.
Simpson et al. (1999) Annu. Rev. Cell Dev. Biol. 99, 519-550.
Coupland (1995) Trends Genet. 11, 393-397.
Mueller and Jaehning (2002) Mol Cell. Biol. 22: 1971-1980.
Wilson et al. (1992) Plant Physiol. 100, 403-408.
Koornneef et al. (1994) Plant J. 6, 911-919.
Lee et al. (1994) Plant J. 6, 903-909.
Michaels and Amasino (1999) Plant Cell, 11, 949-956.
Sheldon et al. (1999) Plant Cell, 11, 445-458.
Rouse et al. (2002) Plant J. 29, 183-191.
Koornneef et al. (1998) Genetics, 148, 885-892.
Koornneef et al. (1991) Mol. Gen. Genet. 229, 57-66.
Lee et al. (1994) Plant Cell 6, 75-83.
Aukerman and Amasino (1996) In Seminars in Developmental Biology, vol. 7 (Amasino, R.M., ed). Cambridge: Academic Press, pp. 427-434.
van Nocker et al. (2000) Plant Mol. Biol. 44, 107-122.
Macknight et al. (1997) Cell 89, 737-745).
Schomburg et al. (2001) Plant Cell, 13, 1427-1436.
Koornneef et al. (1998) Plant Mol. Biol. 49, 345-370.
Johanson et al. (2000) Science, 290, 344-347.
Lee et al. (1993) Mol. Gen. Genet. 237, 171-176.
Michaels and Amasino (2001) Plant Cell, 13, 935-941.
Michaels and Amasino (2000) Plant Cell Environ. 23, 1145-1153.
Gilmour et al. (2000) Plant Physiol., 124, 1845-1865.
Liu et al. (2002) Physiol. Plant. 114, 125-134.
Gendall et al. (2001) Cell, 107, 525-535.
Pirrotta (1997) Curr. Opin. Genet. Dev. 7, 249-258.
Ronemus et al. (1996) Science, 273, 654-657.
Finnegan et al. (1996) Proc. Natl Acad. Sci. USA, 93, 8449-8454.
Finnegan (1998) Proc. Natl Acad. Sci. USA, 95, 5824-5829.
Tian and Chen (2001) Proc. Natl Acad. Sci. USA, 98, 200-205.
Burn et al. (1993) Proc. Natl Acad. Sci. USA, 90, 287-291.
Torii et al., (1998) EMBO J. 17, 5577-5587.
Hajdukiewicz et al. (1994) Plant Mol. Biol. 25, 989-994.
Onouchi et al. (2000) Plant Cell 12, 885-900.
Neer et al. (1994) Nature 371, 297-300.
Soppe et al. (1999) Development 126: 4763-4770.
Lee et al. (2001) Genes Dev. 15, 912-924.
Verma et al. (2001) Mol. Biol. Cell, 11, 3425-3439.
Ito et al. (2001) Proc. Natl Acad. Sci. USA, 98, 4569-4574.
Gavin et al. (2002) Nature, 415, 141-147.
Alvarez-Buylla et al. (2000) Plant J. 24, 457-466.
Ratcliffe et al. (2001) Plant Physiol. 126, 122-132.
Scortecci et al. (2001) Plant J. 26, 229-236.
Goodrich et al., (1997) Nature 386, 44-51.
Gómez-Mena et al., (2001) Plant Cell 13, 1011-1024.
Serrano-Cartagena et al., (2000) Genetics 156, 1363-1377.

* cited by examiner

*Primary Examiner*—Stuart F. Baum
(74) *Attorney, Agent, or Firm*—Medlen & Carroll, LLP

(57) ABSTRACT

The present invention relates to plant genes involved in regulating flowering, and especially to genes involved in the induction of flowering in response to cold, or vernalization. In particular, the present invention provides the identification, cloning, and characterization of genes involved in vernalization, and specifically of VIP genes, as well as to the proteins encoded by these genes, and to methods of using the VIP genes and proteins. Mutants of VIP genes, where the mutation is a knock-out mutation, confer a vernalization independence, or constitutively vernalized, phenotype in a plant which in the non-mutant form requires vernalization to flower.

2 Claims, 26 Drawing Sheets

Figure 3

VIP3 Nucleic Acid Sequence

Sequence and annotation of the F27B13.70 (VIP3) region

```
21901  gcccgtaaaattcaaagacgagagctaaaagcgatctcaatcgattaaaattaaataaca
21961  gagagaccacgagagcagagaagacgcaagaagaagagtgaagaaaggtgtcgtagtcgg
22021  atcactgagacgtggcggctccagagagtacttctccgcaattagctgacgacggcggga
22081  gagtgaggaagaagatattaatgggcctgttacgatattaatgggcctttagtagtaaac
22141  aagaatacggaacgatgttaaacactctattgtttccaactactaaaaacgacgcgagtt
22201  tctattttataactaaaaaacgagaatcaaagtctctgtttcaaatttgggtcttttgct
22261  tcttcttgctcacttgaggaaacacaGTAAAAACCTAAAAAGAGAATGAAACTCGCAGGT
22321  CTGAAATCGATCGAGAACGCTCACGAAGATTCCGTTTGGGCAGCGACGTGGGTTCCGGCG
22381  ACGGAAGATCGACCGGCGTTGCTTCTGACTGGATCTCTTGACGAGACGGTGAAGTTATGG
22441  CGACCGGACGAGCTGGATCTTGTGCGGACTAATACTGGACACTCTTTGGGAGTAGCAGCT
22501  TTGGCTGCGCATCCTTCTGGGATTATTGCAGCATCTTCTTCGATTGATAGCTTTGTCCGT
22561  GTGTTTGATGTTGATACTAATGCTACGATTGCTGTTTTGGAAGCTCCTCCTTCTGAGGTT
22621  TGGGGAATGCAATTTGAACCTAAGGTAATTGACTCAATGAGATTGCCTCCAATTTTAGGG
22681  TTTTGAAGGATTTTGGGTTGTTTTGTGGTGAAAGAATTCGATTGCTTCATTGAATTTCAC
22741  TTCTTAGTTGCGAGTAATGCTTCTCCTGATCTATATAACAATGCTTGGGTACTATATGGA
22801  ATTGCTGAGTATCGTTTGAATCTGTAGCTCTGATCAGATAGGGTCATCTACTCTGCTCGG
22861  AAAATAGATCTAGATCATCTTCTGATTTTTCATTGAGTCTTATATAGTAGATTAAGAACA
22921  ATTTATTGGTGCTTTGATGATAAATCTTGATTTGGTATGATAGAATTTTGACCTGGTGAC
22981  TATCAAGTATCAGTGCAATGATCTCTCTTTTAGTTTGCAGTGGAGTTTTTATTTGCTTCT
23041  GAGCTTATAATTTCAACATTACTCTTTAGAATGGTGCTCTGCTAACATAGTATTTTACAT
23101  GTTCCAAGGGTACGATCCTTGCTGTTGCAGGTGGAAGTAGTGCCTCAGTCAAGCTTTGGG
23161  ACACTGCAAGCTGGAGATTAATCTCAACTCTATCAATCCCACGCCCAGATGCACCAAAAC
23221  CTTCCGATAAAACCAGCAGCAAGAAATTCGTTCTCTCGGTGGCTTGGTCTCCTAATGGGA
23281  AACGACTTGCTTGTGGTTCAATGGATGGTACGATCTGTGTTTTTGATGTTGACCGCTCAA
23341  AGCTACTTCACCAGCTAGAAGGTCACAATATGCCTGTAAGGTCCCTTGTGTTCTCCCCTG
23401  TAGACCCGAGAGTCCTCTTCTCTGGATCAGATGATGGGCATGTGAACATGCACGATGCAG
23461  AAGGGAAAACGCTGTTGGGGTCCATGTCAGGGCACACGAGTTGGGTGCTGAGCGTTGATG
23521  CTAGCCCAGACGGTGGAGCCATAGCAACCGGCTCAAGCGATAGAACTGTGAGGCTATGGG
23581  ATCTTAAAATGAGAGCTGCGATTCAGACAATGAGCAACCACAATGACCAGGTTTGGTCTG
23641  TGGCCTTTAGACCACCAGGTGGAACCGGTGTCCGGGCTGGTCGACTTGCTAGTGTCTCTG
23701  ATGACAAGAGTGTATCGCTCTATGATTACTCATGAACAATTCGGTTTTTTGACTTTTTTC
23761  TTTTATGCATTCTCCAAGACGCATCtagttgtaacaatataatctgcaacaggttgattt
23821  tgaccggagtctttagatttatcgcttacacaaaaaacaaagaagataaaatgattcaaa
23881  ctttgcgatagaactttattggaaaactgagaaacagataaagatcacagagagatgagt
23941  tgaagagtaacgcaaacaaacgtctaaaagttttcaaaaaacaaaacagctaaagattat
24001  ggtcttgtctctt
```

Figure 4

VIP3 Amino Acid Sequence

**Sequence and annotation of the F27B13.70 (*VIP3*) region**

MKLAGLKSIENAHEDSVWAATWVPATEDRPALLLTGSLDETVKL

WRPDELDLVRTNTGHSLGVAALAAHPSGIIAASSSIDSFVRVFDVDTNATIAVLEAPP

SEVWGMQFEPKGTILAVAGGSSASVKLWDTASWRLISTLSIPRPDAPKPSDKTSSKKF

VLSVAWSPNGKRLACGSMDGTICVFDVDRSKLLHQLEGHNMPVRSLVFSPVDPRVLFS

GSDDGHVNMHDAEGKTLLGSMSGHTSWVLSVDASPDGGAIATGSSDRTVRLWDLKMRA

AIQTMSNHNDQVWSVAFRPPGGTGVRAGRLASVSDDKSVSLYDYS

Figure 5

VIP4 Nucleic Acid Sequence

Sequence and annotation of the MAF19.15 (VIP4) region

```
52141 attggttttt ttttttttgg ccaggatacg aaactcatct tagtttcgga ttgttatttg
52201 gggtttgaac aagaacactc cattgaacaa cttgcacgac gcggatgagc cattagatga
52261 tggattgtag taaccccata tttttttgga atttgtttta tatattgtca aaattttctt
52321 aaaattctgg ttttttttg tcgtcttctt aatgtaaaac caaattttac cttacgtttt
52381 gtaataaaac agtgttacag atcttttgag atacataaga aaaataatga agagcttaag
52441 gtaaatgtgt taattttaca taacgttatg tagaacagtg ttacaaaaaa attgggctac
52501 atgactacat aataaattaa tcaagagatt aaaactaaat gtgtttactc tgtgacagtc
52561 tgtttggtaa atttgtttgg gtcaacaagt ttacgttATT TGAACTATC TCCATATCAA
52621 ATTACCAATT ATTCATTACA GTTACAGAAG GGAAATAAAA TCCATTATTA CATGAATTTA
52681 AAAAAATCAT GATTCTGTCT TTATTTTGAT TAAAACGAGT CTAATTCCAG ACTACATTAT
52741 AACAAATGGA CGAAAGGAGA GTGAAAGATT TGACGAACAT GATTAATCTT CGTCACTGTC
52801 ATCAATCACG GCCTTACGAC GATGAGTCGG AGCTTTTCTA GGCGGAGACT CCTCCTCGTC
52861 AGACTCAATC CCTTTCCTTT TCCGGCCACT TCCACGGTGA TCCTTCTCTG CCCTACCTCC
52921 CTGCATAAAC CACATTTCAC CACACATTAC AATCTCAATG AACTTCCTCA TTGACAACAA
52981 TAAAAATGGA AGAACATTCT AATTTGCGTA CCGCAACCTC TTCCTCTTCT TCATCTTCAT
53041 CTGAGTATCT GTTAGATTTT CCTCGTTCCT CTTCATCTTC TTCTGCATCT TCCTCATATT
53101 CATCTTCTGA ATCCTTGCCC CTTCCACGGG CCGGTGACTT TTCTTCCTCT TCTTCTTCCG
53161 TCTCATATTC TGATTCCTCT CTCTCACTCT CAGAATACTC CATTTGACGT CTTGACGGTC
53221 TGGCCGAAGT CATTGAAGAC CTCCCCGGAA TGCCTTTGTG GCTCTGGTTT TACCCCAGTG
53281 AGAAGCAGTT GAATATTAGT TCAATTTCTA ATGCTTTTTT TGCATTCCGA GATATATGAG
53341 TTTTTGTTTT GTTTACCTTC TTGGCGTTTA GAATCCGGCG TTCCCGTTGC GCTTCAGCTT
53401 CGAGATCTTC CTCATAGCCA CGGTTTGAGC GGTAATCCTC GTCATCCTGG TTCCAAGAAA
53461 CAATCAGTCG TTACTAGTGC AATCTTTGCT TTAGAAAATG GAAGAACCCA ATATACACAA
53521 ACTAATCAAA CAGACCTCAT CAAGAGCATC TTCCAAGTAG CCAGTGGAAA GTTGTCTCCT
53581 TTCAACAGGA AGTGGATACT TGCGCTTGAT TTTCTCCCTC GCCTGACTCA GCTTTGTACT
53641 AGCCTTGAGG TTTTGGCTTT CCGCCTTCAG AATTTGAGAT ATTAAATGAG AAAAGTCTAC
53701 AAACACTGCA ATAAAACTAT TGTTGGATTG TCTGAGCTCA ATTAAGAGGT AACCTTTTCT
53761 CTCTTCTCCT TCTCCCTCTC AGGGTCAATG TCAGTGACAC AGTTCTTAAC TTTGAAGGCC
53821 TTCTTCTGCC TCGATTCAAC AATGGCAGTC AAGAGCCTAT GGGAATTTGA CGTCAGCGAT
53881 GATGGGGTAA ATCTCATTTT CTTCAAAATT CTTCCTTGTG ATTGAAGGAT ACCCTACACC
53941 AACATCCAAA TAAGACAACA CTTTGAGATA TAGCAGAGTT GGAATGCAGG AGACATTTGG
54001 TTTCCTAATG AGAAGTTTTG TCATTTAGTA TAGAGAATCG TATGGGTGCT CTAAAATGAA
54061 TCAGTGTATC TAGGAGGCTG GAGCAACTAC AAATTGATCG CTAACTAAGG CAGAAGGAAT
54121 GACGAAGTAA CACCTTTTCA TGTTTGATAA AGAGGTGATT CTGGTCTTCT TTTGCATCTT
54181 GTTCAGTTAT GTTAAGAACT TCGTTTCCTA TCAATAGCTG TAAGCTTCCA TCTGACCACC
54241 TTACAAACCG AGCATTACTT TCACTCTGCA TACGAATATA GAGTGACTTG AGTTTACTAC
54301 AGCAAAAGTA ACGGAAAAAG TAGAAGAAAT GTGTGCAATA AGCAACAAAA CCAAGAATTC
54361 TTGTTTATGG GCAGATTTCT AATGAAGCCT AAAGAATAAG AAGAACTGTT GAACAGAGAT
54421 ATCATAAAAT TTCATCTCCA ACTATATGAA CACATGTCCG TAGTGAAAAG CACAAAGTAA
54481 ACTAATTCGG AATACATAAA TTGCATCAAA AGTATGTACT TATAATACAT CATTGCATCA
54541 GAAGTACTAG TAATAGGCAA ACTACATAGC TTCATTGCAG GTTTGATGGA AAATTTAAAA
54601 GCAGAAAAGC TTTGAAGAAG TGTTCACTTA CATATGTTTT GCCATCTCGA CTCTTAACAA
54661 ACCTATGGCG AACAATATTA TTGTCCAAAC GGATACGATT CTTTGCTCCG GGTTCATCTG
54721 TCATGAATGT GTCTTCTTCA ACGAATGTTT TGGCATCAAA AGGCTTTGGA TCAATCCCCA
```

Figure 5, continued

```
54781 TGATATTGGA AACTTTTATC ATGTTCATCT GAAAAAGATC AAAGAGAAAA CGGTATATGA
54841 GGAAGCGCAA TTTTGCTACA GAACATCTTC ACTACAGATA GACAACTAGA AAATGGGGTT
54901 TCAGATATAA AACAGAATAG CACGCTCATG TACACCAAAT GGCCCTTCAT GCTAAGTAAA
54961 TGTAGAAGCA TGTTTCAGTG CAATGGTTCT CCACATAAAA GACATCAGAT ACTCACTCTT
55021 CGAACCACAA TGATATGAGA GATTTTGGTA ACTTGGAAAT ACCAGAAAGG AAACTATTGA
55081 TTTGAAGCCA TGTCAGCGAA TAATCTTTTA 'GCAACATAAA GCAGGTATAC CTTAACGGGG
55141 TCACCTGGAG GAGGGCGGAA AGGAACCTCC ACTTCCAAAG GGGGACCAAC TGGCCTCTCC
55201 CTGTACCTAG CTTAACATG TTCAGCTTCT GACTCGTATT GAGGATCTTC TTCAGGGATT
55261 ATATCATCAA GCACCATATC ATCGGGTCTC AGATCCTTCT CAGAGCCCTC TTCATCTTCG
55321 ATTGGCGATC TCTACAAAAT TAGACATCTC ATCATACATA CATGCAATTT CATATGGTTT
55381 CTAAAAGGAA GCAAACACTG GAAAGGAAAC AGATATTCTG TAAACTGAAA TGTAATATTA
55441 GATGCAAGAC TCACATGTTC ATCCTGCTCA ACGTCATTCC GAACATATTC TTCTGCGTCT
55501 TCATCATCCG AAGATCCGAA AACATTACGA ATATTTACGT CTGACTGTGC AACTTGAACC
55561 TCTTCCTTCT CCTCACTAGG TGATCTACCC ACCACGCCAT ATTTCCATGT ACAAAAGACA
55621 AAGTGATCCA TAAGAAATTT GAAAATCCAA GGAACCTCAG AGGACTAGCA AGTATTATTA
55681 AATCCAGAGC ACAGAAAAGA TCAAAAGAA GCTATGAAAC AGCTAGGAAA AAAAAGAATG
55741 GAAAAGGGG TACCTTGGAC TCCTAGTCTG ATCAACCTCT TCATCTTCAG ACTCATAATG
55801 CTTTTCACCA GACCTCTCTG ATCCGCTCTC AACAACCTCC TGTCTCCTCT TTTTGGCTAC
55861 TCTACCCCCA TGTTCTTCTT CTTTGTTATC ACTATCACTA TCTCTTGCTT CACTTTCCTC
55921 TTGTGGATCA GCCTCCTGTG AACTTTGCTC CCTCTCACCC TCACTTTCTC CAGGATCAAG
55981 TTCTACATCT CCCTGTTCCC CGTCAGACTC AGCTTCAGCT TCTCCGTGAA CTTCAACCTC
56041 AGCTTCACCT TCTCCTTCAG GCTCCACCCC GCCCTCAGCC TCATCCTATC AGTGTTTACA
56101 TTGGAAATTT CAGCCACAAT TTCACTGATA TCTTAGTCTA GTTGATATTA AGAAGAACTG
56161 AAGCTGAATT AGGCCTAATA AGTTGCATTG GTTCCTGCAA TTAACCTAAA ACCCTAAATT
56221 CAAGCGAGAA GAACTCCAGA AACCATTCGT ATTCCAAGGT GTAATTGAAG AACAGTGGCA
56281 GTGAAAAATA CGAAAACTGA AACAATCAAT AGTGACGAAA CGAAGGAGAT AAACATGGAG
56341 AGAGTTACGG AAGCGTAGTT AGGCTGACGA CGATTGCATT CATGTTCGGA TTCGATCTCT
56401 TCTTCCTCGG AATTATCTCC GAACAGATTA AGCATCATCT CGGATCTCTT TTCTCCTTTA
56461 ACCATCTTCG CCTCACTTAC TCAAAGTCA CTGCCTCTTA GCTGGTGACG GCGGCTCGTG
56521 ATCTGAGCTC CGACGAAGGG TTCACTGTTA TCGGCCTTTG TTGAAGAAGC TATTTTTTTT
56581 TCATCTCTAC CTCGCGATTT TATGGCATCA GAATTATTAT TATTAAAAAC AATTGTTACA
56641 ACTTACAAAG AAAAGGAAAT TTcatcgat atatctttt taacgcatta ccggattatt
56701 aaaaatcatt ttttttacgt gtaacgacga ctagagaggg aaaaaagatg ggattttatg
56761 ggctttttg agattggaat tcaatatttt tggcccacaa attttgggtt atggatacca
56821 gtttctttgt gatagtgagc ttgtgtttgc cttggccct atgtatatga atgatacaac
56881 atcctttaa ctgattcttt tggccctat tttttatat ttaattatt ttaaaaacta
56941 attattaact tctttgatca aataacttga gttgccaaaa taaatgttat gtcttcttct
57001 aaaacattgt tgttggttta tagatttat ctgctttaga aattaacaag agacaaagat
57061 taggtaaaag cataaccgac ttgtgttcta tgaaaactta agtgacaact aaacatcatg
57121 aatattcagg aaatcctgaa aatttaaaca gaattatagt aatttctgaa aaactcaaga
57181 aattatggaa taaaaagaaa aagaaaaaa ctatggacac ttttaaatta ctcaaactag
57241 tttaaggctt ttggaaattt cactttttgc ttttttttaa ctcgagaaaa ttacaatttt
57301 atgtagacac attttgctca caaatgttta tttatatatt ttccataaat ttattttca
```

Figure 6

VIP4 Amino Acid Sequence

Sequence and annotation of the MAF19.15 (*VIP4*) region

MVKGEKRSEMMLNLFGDNSEEEEIESEHECNRRQPNYASDEAEG

GVEPEGEGEAEVEVHGEAEAESDGEQGDVELDPGESEGEREQSSQEADPQEESEARDS

DSDNKEEEHGGRVAKKRRQEVVESGSERSGEKHYESEDEEVDQTRSPRSPSEEKEEVQ

VAQSDVNIRNVFGSSDDEDAEEYVRNDVEQDEHRSPIEDEEGSEKDLRPDDMVLDDII

PEEDPQYESEAEHVEARYRERPVGPPLEVEVPFRPPPGDPVKMNMIKVSNIMGIDPKP

FDAKTFVEEDTFMTDEPGAKNRIRLDNNIVRHRFVKSRDGKTYSESNARFVRWSDGSL

QLLIGNEVLNITEQDAKEDQNHLFIKHEKGILQSQGRILKKMRFTPSSLTSNSHRLLT

AIVESRQKKAFKVKNCVTDIDPEREKEKREKAESQNLKASTKLSQAREKIKRKYPLPV

ERRQLSTGYLEDALDEDDEDYRSNRGYEEDLEAEAQRERRILNAKKSHKGIPGRSSMT

SARPSRRQMEYSESEREESEYETEEEEEEKSPARGRGKDSEDEYEEDAEEDEEERGKS

NRYSDEDEEEEEVAGGRAEKDHRGSGRKRKGIESDEEESPPRKAPTHRRKAVIDDSDE

```
             A                      B       C
MKLAGLKSIEN  AHEDSV WAATWV PATEDRPA  LLLTGS LDE TVKLWR  PDELDLVRTNT                          57
             GHSLGV AALAAH PSGI      IAASSS IDS FVRVFD  VDTNATIAVLE                          99
             APPSEV WGMQFE PKGTI     LAVAGG SSA SVKLWD  TASWRLISTLSIPRPDAPKPSDKT            155
             SSKKFV LSVAWS PNGK      RLACGS MDG TICVFD  VDRSKLLHQLE                         197
             GHNMPV RSLVFS PVDPR     VLFSGS DDG HVNMHD  AEGKTLLGSMS                         240
             GHTSWV LSVDAS PDGG      AIATGS SDR TVRLWD  LKMRAAIQTMS                         282
             NHNDQV WSVAFR PPGGTGVRAG RLASVS DDK SVSLYD YS                                  321
            ┌─────────────────────────────────────────────────┐
            │GHxxxV xxVxFx PDG       xLASGS xDx TIKVWD         │
            │A      I      SNS       IVTAG      SVRLFN         │
            │       I L    DSP       VL SA     L IY            │
            │       C I              FI C      A               │
            │         V                                        │
            └─────────────────────────────────────────────────┘
```

B

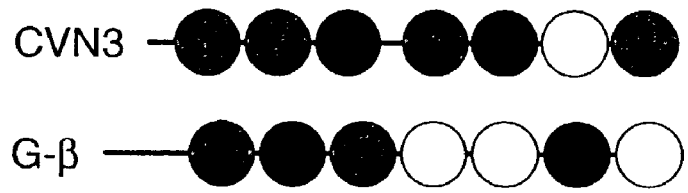

Figure 12

*VIP5* Nucleic Acid Sequence

Sequence and annotation of the AT1G61040.1 (*VIP5*) region

Panel A: Genomic Sequence from AGI (length: 2736)

```
CTTAAAAAATAAAAAGACTTCAGCATCTGCTTCCTCTCGACAATTTCGACATTACTCTTTCGTTTTTCACC
CCTTCCTTCTTCTCCTTTAGCCGCCCGTCGTCGATCTCTGCAACACTTTCCGACGATTTCTCCGTCTGATC
TCAAGTGAGTCTCCTTCAACTTTTCTCTTCTTTTCTATACCCTTCCCTCTCTCTATTTCCTTTTCTCCGCC
ACAAACGGCTTCTGCGTTCCCTGTTTCCGCCGTCCTTACCTCTTCCAATCAAATTGAAGATCCATACCAGA
AATCGATCCTTCTCCGTCTCCGAATTCGCTTGATTAACCTCAGAAACTCGTATTGGTTTTCGCAAAACCGC
GATTTGGCTTTAGACTTCACCGTTACCTGATTGGGTGAAAAGTTTTCCTTAACCCTATTAATGGCTTATCT
AGGGTTAGAATCCAAAGGATTGTTTTGCTCTTGTAGTTAGCTATCTACTGGTTTTTTGTGGTATACACCGT
ACTTGACCAATGTGGTGAGGTCTTTTGCTTCTCTAACTGTATACTTCTCATAATTTCAGGTGACAGTGAAA
ACCATTTAAATTCGTTACTTGTGAGCCTCCTTAGAAGATTATGGGTGATTTAGAGAACTTGCTTTTGGAAG
CTGCTGGGAGAACAAATTCAGCAGGGAGGAGTCGTCATCCTCCATCATCGAGGAGACGTGAGGGTTCTTAC
TCTGATGGTAGTAGCCGATTCAAGCGATCATTCTGATGAAGATCGTGGCTATCCTAGTAGAAAACCCTCTGG
GTCTCAAGTTCCTTTGAAGAAGAGATTGGAGGCAGAGAGAGAAGATCGAGCTGCTCGAGTTGAAGGTGGTT
ATGGTGATGGACCATCTGATCGTGAAGGTGACAGCAGCGAGGAGTCTGATTTTGGAGATGACCTTTACAAG
AATGAGGAAGACAGGCAGAAGCTTGCTGGAATGACTGAGTTTCAGAGAGAGATGATTCTCTCTGAACGTGC
TGATAAGAAAGGTGATAAGAACTTCACTGAGAAACTTAGGTCCAAGAGAGAAAGTGAGAAAACCCCTGTTT
CTAAAAAGGAGACTCAGCCTCTTCCGGCCTCTCGTGGTGTGCGTTCATCTGCTAGATCTGCAGACAGAGCC
GCTGCTAAGGATGATGCCCTGAATGAATTGAGGGCGAAGCGTATGAAGCAGCAGGACCCAGCAGCTCTCAG
GAAACTGAGAGATGCATCAAAAGGTGGTTCAGGTAGTCGAGATTTCTCATCAACGAAGAGGAAACCGTTAG
CTTCCTCCAATTTGAGTAGTTCCAGCCAAAGTGACAGTGATAGTAGGTCTCAGAGTGATGATGAAGGCTCG
AATGGAGGAATGCTAGACAGTGATGATGACAGGTCAGATGTGCCTACGTTTGAGGATGTTAAGGAAGTTAC
CATTAGACGGTCTAAGCTTGCCAAATGGCTAATGGAGCCTTTCTTTGAAGAGCTTATAGTTGGGTGCTTTG
TGAGGGTTGGGATCGGAAGGTCAAAGAGTGGTCCAATTTACAGACTCTGCTGGGTGAAGAATGTTGATGCA
ACCGATCCTGACAAGACCTACAAGCTAGAGAATAAAACTACACACAAGTACCTTAACGTCGTCTGGGGAAA
TGAAACCTCGGCGGCTCGATGGCAAATGGCTATGATCTCAGATGGTCATCCGCTGGAGGAAGAGTATAGGC
AATGGATCAGAGAGGTTGAGCGAACAAATGGTCGCATGCCCACAAAGCAAGATATATCGGAGAAGAAAGAA
GCGATACAAAGAACAAACAGTTTTGTTTACTCTGCGGAAACTGTTAAACAGATGCTGCAGGAGAAAAAATC
TGCGTCAGTCAGGCCAATGAATGTTGCGGCCGAGAAAGATCGGCTTAGAAAAGAATTGGAAATTGCGCAGA
GCAAAAACGATGAAGCAGGTGTAGAGAGGATCAAGTCGAAAATCAAACAGCTCGACGCTTCACGGAACAAG
AAAGGGGTAGATAAAAAAGCGCTTAAACTTGCTGAGATGAACAAGAAGAACAGAGCCGAGAATTTCAAGAA
CGCATCTGAGGTAAAATCAATAACTGCTAGTCTCAAAGCCGGTGAAGCAGGGTATGATCCGTTTTCAAGAA
GATGGACCCGATCATCAAACTACTACAACGGGAAAAACAAGGGGAAAGATGGAGAAGAGAACGAGGCAGCG
GTTGCAGCAGCGGTTGAGACCAATGGAGCAGATGCAGGAGCAGGTGTTGAAGCGACAGAAGCAGCTTTAGA
AGCAGCTGCAGAGGCAGGAAAGCTAATAGACACAAGAGCTCCAATAGGTCAAGGAGCAGAACACAATCAGC
TTCATAACTTTGAATTGTCGTTATCGCTAACGGCTTTACAGAAGTACGGAGGACCTCAAGGAGTACAGAAA
GCGTTCATGGCGAGGAAGCAACTGACCGAAGCAACTGTGGGATGCAGAGTCGCAGAGAACGATGGCAAGAG
ACATGGCCTTACGTTAACTGTTAGTGATTACAAGAGAAGGAGAGGTCTTCTCTGATTTATTTGCATTTTTT
TCAAGTCTCAGTGTTTCATTATCTTCTGAAAACTGCTTCTTGGTTCTTCTTTTCTTCATATCTTTCTTTTG
TACTCCACAAAATATGTTTAGATCAGTTTGTTTTTTCTTGAAATATTTTTGTACTCGTTTTTGTGTGAACT
CTCCTGATTAGTGTATGACTGC ATGAAATTAGAAAATC
```

Figure 12, continued

Panel B: cDNA Sequence from AGI (length: 1932)

ATGGGTGATTTAGAGAACTTGCTTTTGGAAGCTGCTGGGAGAACAAATTCAGCAGGGAGGAGTCGTCATCC
TCCATCATCGAGGAGACGTGAGGGTTCTTACTCTGATGGTAGTAGCGATTCAAGGGATGATTCTGATGAAG
ATCGTGGCTATGCTACTACAAAACCCTCTGGGTCTCAAGTTCCTTTGAAGAAGAGATTGGAGGCAGAGAGA
GAAGATCGAGCTGCTCGAGTTGAAGGTGGTTATGGTGATGGACCATCTGATCGTGAAGGTGACAGCAGCGA
GGAGTCTGATTTTGGAGATGACCTTTACAAGAATGAGGAAGACAGGCAGAAGCTTGCTGGAATGACTGAGT
TTCAGAGAGAGATGATTCTCTCTGAACGTGCTGATAAGAAAGGTGATAAGAACTTCACTGAGAAACTTAGG
TCCAAGAGAGAAAGTGAGAAAACCCCTGTTTCTAAAAAGGAGACTCAGCCTCTTCCGGCCTCTCGTGGTGT
GCGTTCATCTGCTAGATCTGCAGACAGAGCCGCTGCTAAGGATGATGCCCTGAATGAATTGAGCGCGAAGC
GTATGAAGCAGCAGGACCCAGCAGCTCTCAGGAAACTGAGAGATGCATCAAAAGGTGGTTCAGGTAGTCGA
GATTTCTCATCAACGAAGAGGAAACCGTTAGCTTCCTCCAATTTGAGTAGTTCCAGCCAAAGTGACAGTGA
TAGTAGGTCTCAGAGTGATGATGAAGGCTCGAATGGAGGAATGCTAGACAGTGATGATGACAGGTCAGATG
TGCCTACGTTTGAGGATGTTAAGGAAGTTACCATTAGACGGTCTAAGCTTGCCAAATGGCTAATGGAGCCT
TTCTTTGAAGAGCTTATAGTTGGGTGCTTTGTGAGGGTTGGGATCGGAAGGTCAAAGAGTGGTCCAATTTA
CAGACTCTGCTGGGTGAAGAATGTTGATGCAACCGATCCTGACAAGACCTACAAGCTAGAGAATAAAACTA
CACACAAGTACCTTAACGTCGTCTGGGGAAATGAAACCTCGGCGGCTCGATGGCAAATGGCTATGATCTCA
GATGGTCATCCGCTGGAGGAAGAGTATAGGCAATGGATCAGAGAGGTTGAGCGAACAAATGGTCGCATGCC
CACAAAGCAAGATATATCGGAGAAGAAAGAAGCGATACAAAGAACAAACAGTTTTGTTTACTCTGCGGAAA
CTGTTAAACAGATGCTGCAGGAGAAAAAATCTGCGTCAGTCAGGCCAATGAATGTTGCGGCCGAGAAAGAT
CGGCTTAGAAAAGAATTGGAAATTGCGCAGAGCAAAAACGATGAAGCAGGTGTAGAGAGGATCAAGTCGAA
AATCAAACAGCTCGACGCTTCACGGAACAAGAAAGGGGTAGATAAAAAAGCGCTTAAACTTGCTGAGATGA
ACAAGAAGAACAGAGCCGAGAATTTCAAGAACGCATCTGAGGTAAAATCAATAACTGCTAGTCTCAAAGCC
GGTGAAGCAGGGTATGATCCGTTTTCAAGAAGATGGACCCGATCATCAAACTACTACAACGGCAAAAACAA
GGGGAAAGATGGAGAAGAGAACGAGGCAGCGGTTGCAGCAGCGGTTGAGACCAATGGAGCAGATGCAGGAG
CAGGTGTTGAAGCGACAGAAGCAGCTTTAGAAGCAGCTGCAGAGGCAGGAAAGCTAATAGACACAAGAGCT
CCAATAGGTCAAGGAGCAGAACACAATCAGCTTCATAACTTTGAATTGTCGTTATCGCTAACGGCTTTACA
GAAGTACGGAGGACCTCAAGGAGTACAGAAAGCGTTCATGGCGAGGAAGCAACTGACCGAAGCAACTGTGG
GATGCAGAGTCGCAGAGAACGATGGCAAGAGACATGGCCTTACGTTAACTGTTAGTGATTACAAGAGAAGG
AGAGGTCTCTCTGA

Figure 13

VIP5 Amino Acid Sequence

Sequence and annotation of the AT1G61040.1 (*VIP5*) region

MGDLENLLLEAAGRTNSAGRSRHPPSSRRREGSYSDGSSDSRDDSDEDRGYASRKPSGSQVPLKKRLEAER
EDRAARVEGGYGDGPSDREGDSSEESDFGDDLYKNEEDRQKLAGMTEFQREMILSERADKKGDKNFTEKLR
SKRESEKTPVSKKETQPLPASRGVRSSARSADRAAAKDDALNELRAKRMKQQDPAALRKLRDASKGGSGSR
DFSSTKRKPLASSNLSSSQSDSDSRSQSDDEGSNGGMLDSDDDRSDVPTFEDVKEVTIRRSKLAKWLMEP
FFEELIVGCFVRVGIGRSKSGPIYRLCWVKNVDATDPDKTYKLENKTTHKYLNVVWGNETSAARWQMAMIS
DGHPLEEEYRQWIREVERTNGRMPTKQDISEKKEAIQRTNSFVYSAETVKQMLQEKKSASVRPMNVAAEKD
RLRKELEIAQSKNDEAGVERIKSKIKQLDASRNKKGVDKKALKLAEMNKKNRAENFKNASEVKSITASLKA
GEAGYDPFSRRWTRSSNYYNGKNKGKDGEENEAAVAAAVETNGADAGAGVEATEAALEAAAEAGKLIDTRA
PIGQGAEHNQLHNFELSLSLTALQKYGGPQGVQKAFMARKQLTEATVGCRVAENDGKRHGLTLTVSDYKRR
R GLL

Figure 14

*VIP6* Nucleic Acid Sequence

Sequence and annotation of the AT2G06210.1 (*VIP6*) region

Panel A: Genomic Sequence from AGI (length: 6788)

```
GATTCACTTCATCGTTGGCACACACACATACTCTCTATTCGAAAAATTCGCCACTGCAATTTCTTCTAGGG
TTTCTGGTAATCCTCACTTAGCCGGGCAATGGCGAGTGTGTACATACCGGTTCAGAATTCAGAAGAAGAAG
TTAGGGTTGTTCTTGATCAGCTCCCTCGTGACGCTTCTGATATACTTGATATTCTTAAAGCCGAACAAGCT
CCTCTCGATCTCTGGCTCATCATCGCGGTTCGTTCTTTTCCACTCTAATTAGGTTCTATCTGGAATCGAGT
TTTGTTGAGTTTTTCTTAGTTAATGGCTGATGGGTTTTGATTAACACTTCAAAAGTTAGTTGCTTTTGTGG
CTGATTTGCTTAAAGATTGTTTTTTTTTCCAATTCTGATTTTGGTTTCATCTATGGTGAAGAGGGAGTACT
TCAAACAAGGAAAAATTGAACAGTTTCGACAAATATTGGAGGAAGGGTCAAGTTCTGGTAAGCAGTTATAC
GATGATGCTGCTTCAATTTGTTCTAGAATTGGTTATTTCGAAAATATAAGTCCTTTTTGTTTCTTTTTGGC
AAGACATTGACGAGTACTATGCCGATGTTAAGTACGAGAGAATAGCGATTTTGAATGCTCTAGGTGCGTAT
TATAGCTACCTTGGTAAAACTGAGACCAAAAACAGAGAGAAAGAGGAGCAATTTATCTCTGCCACACGATA
TTATAACAAAGCATCGAGAATCGATATGCATGAACCTTCCACTTGGGTTGGGAAAGGTACTACCAGATTCG
TTTCGACTGATAAGTTTCTGTTGCAAGCAATTCCTATAACAATCTTTCTTTTCCGGTTCTCCCTGTACAAT
GTACGCTTTAAGAATTTGAAGGTTGTGATGATGCTCTATGTTTACTAAGATACAGAATCCTGAAATGTAAT
TGTCTGCTTACAGGTCAGCTCTTACTGGCTAAGGGTGAAATAGATAATGCTCTTCAGGCATTTAAGATTGT
GTTAGACACTGCCCCTGATAATGTTCCTGCTCTTCTGGGTCAGGTATAATGACTTGTGATTTCATTTTCTG
TCACTTAGCTAATAATTTGTAGGTAGGTAGATTCTGTATACTAGAATTTATTGGTGGTAGTAAGAATTTGA
TTCTGACGCTCTCTTTCTTACCAACCTAGGCCTGACACAGTATTAGTCTATTGTTTACTTTTCTGCAAATT
AATAACTTGCTCTATCACGTATACAGGCTTCTGTAGAATTTAATCGTGGACGATTTTCTGAGTCATTACAA
CTATACAAGGTAAGCTTTTCCTTATAACCTACTATATTTCTGTATACCACTTCTTCATTTTGGCTGTAAAT
CTCATGGCTTTGATTGTTCAAGTGAACCATCTAGTCTATTTATGGAACAAATTGGTAGTATTTTGATTTGT
CTATGTTTTGAATTCTTTTAGAGGGCCTTGCAAGTATTTCCCGGTTGTCCTGCAGCTGTGAGACTGGGAAT
TGGTTTTGTCGTTATAAGTTGGGGCAACTAGATAAAGCACGGCAAGCGTTTGATCGCGTTTTGCAGGCAAG
TGGGACTGGGATGTTTATCTCATCTTCTTATGACATAGCTGACTGTATGCGTCAACAAATAGTGCTAATTA
CCATAATTCTATTTCTGCAGCTAGATCCTGATAATGTTGAGGCTCTTGTGGCACTTGGGATTATGGATTTG
CAAGCAAATGATTGTAAGTATACCTCAGTTCTAAATCTTATGATAATGCGTGTGGGCTGGAAAGATTCTAT
TAACTTTACTTCTCTTTGGCCTTCACTGATGATATTACATATGTATAGCTATAGGAATGAGGAAAGGAATG
GACAGAATGCAGCAGGCATTCGAGATTTATCCCTATTGCGCATCAGCCTTAAATTATTTGGCCAATCACTT
TTTTTTCACCGGCCAGCACTTTCTTGTTGAGCAGCTGACTGAAACAGCATTAGCCGTCACAACTCATGGGC
CAACAAAGTCACATTCTTTTTACAATTTAGCACGGTCATATCATAGCAAGGTTTGACATTTTTGTCCTCCC
TTGTATATTCCATTCTTATCTACCCTCTGAGCTTGCCAGTGGAGGAAAAAATACGAGTAATAAATAATTTA
TTTGGGTTGTGATATATTTGAGGCGTTTTTTTCATTCTATGGGCTGTTATAGAAGAATGCATCTTTTTTTG
TTTCCTTTGTGTAACCTTCCTTTCTGATGTCTGATGATGGTCTTGTTTTAGGGGACTTTGAAAAGGCTGG
GATGTACTATATGGCAGCCATCAAAGAAACTAATAATAACCCACACGAATTTGTATTCCTTACTTTGGTA
ACTTTTCTCCACTCTTCTGCTGAATTCCCCTTAATTCTTCGGATGTTACCAATCTGAGTCATTACTCATTA
GCAATGAAGATACTGCACCTTTGTCATTTATTTCCCTTTAGCAGTAGCAGTAGAATATATGAAATGAGACCATCAA
TAATTAGTTCCAGTCTGTAAAACGTATGATTATGAACAAATTTGTGTATAATATCTCGTGCTTCAATTTCT
AGTATTGCTCAGTTTGGATTGATGATCTTATATGTTCATTTAGTTTGATTTTTTTTTTGTGTTGCAGGTT
TGGGTCAAGTACAACTAAAGTTGGGGGAGCTTAAAGGATCTGTATTTAATTTTGAGAAAGTATTAGAAGTT
TATCCTGACAACTGCGAGACTTTGAAGGTTAAATGACTGCAACCTTTTTCTTTATTGATCGTTCATTCTGT
ATTTCATCCTTTAAATATAAAATGCTTTATGTGCACGTTTCTTTTCTTTCTTAGGCTCTCGGGCACTTATA
CACCCAGCTTGGACAAAATGAGAAGGCCCTTGAGTACATGCGAAAGGCCACAAAACTTGATCCACGTGATG
CCCAGGTTAGTTTGGTTTAACATAATTCTTAAGCCTGATCTTTCAAAAGGTGTTGATACTTGCATGAATTC
TTTGGTTGTAGTTGTTATATAGTTTACCTTACTGTGGATCACTTTCGAGTGACACTTCCACTTTTGTTACC
TAAATTGTAACACCAGCACACTTAGTCCAAGTAAGGAAGAAAAACATAGTAGCAAGACATAGTTCTGCCA
TATATCTTGAGAATACCTTTTGGGTTTGTTTCCCCCACAGCTCATATGTGTGGTTGAAGATCTAATAGGGA
```

Figure 14, continued

```
TGATAATCATCTATTGACTATTGCGATAATTTTTTCCTTGATTTATAGTTTTGGGTTTTGTAGGCATTTGT
TGGCCTTGGTGAGCTGCTGATATCATCTGACACGGGAGCCGCCCTTGACGCCTTCAAAATGGTAAAGTGTG
ATCTTGATAATTGTATCTCCTCTTCAAGTACATGATGGCATGTTGTACATAAAGAAAGACATTAATTTTTC
TGAGAACCATTAATGAAAACTCCCAGGCACGGACGCTCATGAAAAAAGGAGGGCAAGAAGTGCCTATAGAA
GTCCTGAATGACATCGGTGCTTTACATTTTGAGAGAGAAGAATTTGAGGTTTGTAGTGAGGTTGTTTCTGC
TTCTTAGCTTTGATATTTTGCTATTGGCTTCAATACTCTTTTTCCTTGCAGTCTGCGCTTGAGAATTTTAA
CGAGGCTCTGGGTGATGGAATATGGATTAGCTTCCTTGATGAAAAAGAAAATTTGGAACAGACAGGTGTAT
CTGTTCTCGGGTACAAGGACACGGGCATTTTCCATAGGCTGATTGAAAGTGGTCACTCTGTCGATGTACCT
TGGAATAAAGTTACAACTTTGTTTAACCTGGCTAGATTACTTGAACAGATACACAAAACAGAAGCAGCGAC
TTTTATGTATCGGTTGATACTTTTCAAGGTCTATATTTCCTACTTATTTAATTTGATATTATTTGCTGTTT
CACTTTGTGATGAGTTTTCTAGTGGTAGACTTGAGGAGAAAAGAAGGAAAAAAACTTGAGGAGCCGTTTTC
TGATTATTCCTGTCTGATAGATGATTTTGAGTGGTTACTTGGTTTTTACAAATATATTTTGTCTTAAAACC
CTTCTTTCGCGGTTTTTTAAATATCTATTCATGTACTAAAAGTATAAAAATGGGAACATTGATTCGGCATA
ATGACTTCCTTGGTTATAATTGAGTGGCTTCTGCTCTCTTGGGAAGTTCAGCATCGTTTCGTATATGTGCT
ATATAGTTTTCTGCTTTATATTTCTTCTGTTTCTTATAGTTTTTGGATACACCTACCATGTCTTACATTAT
TTGTTTGAATGTTCACCCTGATATAAGCTTGATCCTTTTATTTCTCTTTCAATAATCTGATGACGACTTTT
GATTTCTGTCAACTTAATCTGACTGCCTATCCGGTGCAGTATCCTGGCTACATAGATGCTTATTTGAGGCT
TGCTGCAAGTGCAAAAGCTCAGAACAATCTTCCTCTGGCCATTGAACTGGTCGGTCTACCACCGTTTTCAA
CATTAATTTTATTTAATCTGTAGCAGCTTGTTTTCTCTCTCTGACCGTCTTTTCCTACTTCCCCTATAGGT
GAATGAAGCTCTGAAAGTGGACGATAAAAATCCAAATGCTTTGTCTCTACTTGGTGAATTGGAGCTTAAGA
ACGATGACTGGGTTAAGGCAAAGGAAACCTTTCGAGCTGCTAATGATGCAACTGATGGGAAGGACTCATAT
GCTATTCTTTCTCTGGTATATATTTTTATTTCCGATTTTTTTGCGTTTCAGAATAATAAGAATCATCATAT
TAAGTTCCTTTTGGGTTGTTCAAAGCTCATCGCATTATCATATCAATGAATCGATTTTATGTGAGCACCCC
ACACCCAAATATTTGTACCCTGCCTTTTCTATGGGTCCAATCTAATCAGCTATTACTGCGATCTGGGCTCT
CTTGTAAAACACTTCAGTCAAGATAACGATAGGGTTCTTTTCAATACGTGTATGGAAGACCAGCCCTCATT
CTGTATGGTTCCTCTACCAGCAGCCTGGTGAGGGCTGGTTGTCTAGCAGATATCTAACTACCTTGGAGTGA
ATTCTGTCTTGATTATAAATGATTGGAACAATTATTGTACAAGCTATTTTTGTGTGTGTAATATTTCTTCC
TGGAATGTTTTAGGGGAACTGGAACTATTTTGCAGCAATGCGCAATGAGAAAAGAAATCCAAAATTAGAAG
CTACACATCTGGAGAAGGCCAAGGAACTCTATACTAAAGTATGGTGTTTAGTTTTTCTCCTTTCTCTCTTC
TAATTATTAGTAATTTGGGAATATGTATGTGCTTCTGGGGGGTGTTTTGGGTGGAGGTTTGCCTGTAGAAA
CCTGAACACGTTGTTGAAATTTTTGCTATACCAGTAGCATTGCATGCTTAAATTGGCGATGTCCTCTTTCC
ATCAACGCTAATCGTCTTTCTCATTGTTGATCGTTGGGATTAACAGGTCCTGACTCAACATAATTCCAACA
TGTATGCTGCCAACGGTTCTGGCATTGTATTAGCAGAGAAAGGCCAATTTGATATTGCCAAGGATGTTTTT
ACTCAGGTCAGCTTTTATCATTTACTGTTCATAGTATAGGCTAGCTAAATTCTTGAAATCATTGGAATTTT
GTGAATGTTTTAGGTTCAAGAAGCTGCGAGCGGAAGTGTATTTCTTCAGATGCCTGATGTATGGGTGAATC
TGGCTCATGTTTACTTTGCTCAAGGGAATTTTGCCTTAACCGTGAAAATGGTTTGTCATTTTATATAGCGT
TTTTTTTTTTTTAAATTCTTTTGGTTGATTTCGATGTTTTGCTTAAGTACTCTGTTCATTATCTATGTTG
TTGGCAGTATCAAAACTGCTTGCGAAAGTTCTTTTACAACACAGACTCCCAAATCCTTCTTTACTTAGCCC
GTACCCATTATGAGGCTGAGCAGTGGCAAGAGTGCAAAAAGACACTATTAAGGGCCATTCACTTGACTCCT
TCAAATTACACATTCAGATTTGATTTGGGTGCTGTAATGCAAAATCATCGTCTTCCACACTGCAAAGAA
AAAAAGAACAGCTGATGAGGTTAACTAAAGATTTTCCCTTGCTTCTTTCTGACTCTAGTCTTGTGTCGTAG
AAGATAGACAGATATTAACATGCATCGATTGGGAATTTATCAGACTATGAACTTGCTTCTACAGCTTGTGT
ATCTAGAACTTTTCACCATGACCCTAGCATAGTATGTTAGTCATCCTTGCTAAGTAATGGCTAATCTAGAA
TGCAATACTAGGATTTGTTGTCTTGTTTTATTAGAAGATGTCTAGACAATACTAATTCGTCCAATGGGGAT
TAATTGATTTCCACCTGACAATTACTTGATGACTCTGCAGGTGCGCTCAACAGTTGCAGAAGCAGAGAATG
CTGTTCGTGTATTCACTCAATTGTCTGCTGCTTCAGACCTCCATGTTCATGGGTTTGATAGCAAGAAATA
CAAACCCATGTTCAGTATTGCTCGCACTTGCTGGAAGCAGCAAAAGTTCACCGTGAAGCTGCTGAGCAGGA
GGAGCTGCAGAACCGACAGAGATTAGAAGTTGCTCGTCAGGCTGCTTTGGCAGAAGAAGCACGCCGTAAAG
CTGAAGAACAGAGGAAATATCAGGTAACTATTGACTTGCAAGTTAACCATTTGCAGCAACAAATTTATTTT
GGTGATATATATGGAAGCTTTTCAAGTCAGTGATATGCATTTTTCTCTTGGGCAGTTGGAGAAAAGAAAAC
AGGAGGAAGAGCTGAGACGCCTAAAGCAAGAAGAAGAAAAATT
```

Figure 14, continued

Panel B: cDNA Sequence from cloned cDNA: Short form (length: 3679)

```
   1  cgattcactt catcgttggc acacacacat actctctatt cgaaaaattc
  51  gccactgcaa tttcttctag ggtttctggt aatcctcact tagccgggca
 101  atggcgagtg tgtacatacc ggttcagaat tcagaagaag aagttagggt
 151  tgttcttgat cagctccctc gtgacgcttc tgatatactt gatattctta
 201  aagccgaaca agctcctctc gatctctggc tcatcatcgC GAGggagtac
 251  ttcaaacaag gaaaaattga acagtttcga caaatattgg aggaagggtc
 301  aagttcTGAC attgacgagt actatgccga tgttaagtac gagagaatag
 351  cgattttgaa tgctctaggt gcgtattata gctaccttgg taaaactgag
 401  accaaaaaca gagagaaaga ggagcaattt atctctgcca cacgatatta
 451  taacaaagca tcgagaatcg atatgcatga accttccact tgggttggga
 501  aAGGTcagct cttactggct aagggtgaaa tagataatgc tcttcaggca
 551  tttaagattg tgttagacac tgccctgat aatgttcctg ctcttctggg
 601  tcAGGCttct gtagaattta atcgtggacg attttctgag tcattacaac
 651  tatacaAGAG ggccttgcaa gtatttcccg gttgtcctgc agctgtgaga
 701  ctgggaattg gttttgtcgt tataagttgg ggcaactaga taaagcacgg
 751  caagcgtttg atcgcgtttt gcaggcAAAT cctgataatg ttgaggctct
 801  tgtggcactt gggattATGG ATTTGCAAGC AAATGAttct ATAGGAATGA
 851  GGAAAGGAAT GGACAGAATG CAGCAGGCAT TCGAGATTTA TCCCTATTGC
 901  GCATCAGCCT TAAATTATTT GGCCAATCAC TTTTTTTTCA CCGGCCAGCA
 951  CTTTCTTGTT GAGCAGCTGA CTGAAACAGC ATTAGCCGTC ACAACTCATG
1001  GGCCAACAAA GTCACATTCT TTTTACAATT TAGCACGGTC ATATCATAGC
1051  AagggGGACT TTGAAAAGGC TGGGATGTAC TATATGGCAG CCATCAAAGA
1101  AACTAATAAT AACCCACACG AATTTGTATT TCCTTACTTt ggtTTGGGTC
1151  AAGTACAACT AAAGTTGGGG GAGCTTAAAG GATCTGTATT TAATTTTGAG
```

Figure 14, continued

```
1201  AAAGTATTAG AAGTTTATCC TGACAACTGC GAGACTTTGA aggcTCTCGG

1251  GCACTTATAC ACCCAGCTTG GACAAAATGA GAAGGCCCTT GAGTACATGC

1301  GAAAGGCCAC AAAACTTGAT CCACGTGATG CCCaggcATT TGTTGGCCTT

1351  GGTGAGCTGC TGATATCATC TGACACGGGA GCCGCCCTTG ACGCCTTCAA

1401  AAtggcACGG ACGCTCATGA AAAAGGAGG GCAAGAAGTG CCTATAGAAG

1451  TCCTGAATGA CATCGGTGCT TTACATTTTG AGAGAAGA ATTTGagtcT

1501  GCGCTTGAGA ATTTTAAGGA GGCTCTGGGT GATGGAATAT GGATTAGCTT

1551  CCTTGATGAA AAAGAAAATT TGGAACAGAC AGGTGTATCT GTTCTCGGGT

1601  ACAAGGACAC GGGCATTTTC CATAGGCTGA TTGAAAGTGG TCACTCTGTC

1651  GATGTACCTT GGAATAAAGT TACAACTTTG TTTAACCTGG CTAGATTACT

1701  TGAACAGATA CACAAAACAG AAGCAGCGAC TTTTATGTAT CGGTTGATAC

1751  TTTTCAagta TCCTGGCTAC ATAGATGCTT ATTTGAGGCT TGCTGCAAGT

1801  GCAAAAGCTC AGAACAATCT TCCTCTGGCC ATTGAACtgg tGAATGAAGC

1851  TCTGAAAGTG GACGATAAAA ATCCAAATGC TTTGTCTCTA CTTGGTGAAT

1901  TGGAGCTTAA GAACGATGAC TGGGTTAAGG CAAAGGAAAC CTTTCGAGCT

1951  GCTAATGATG CAACTGATGG GAAGGACTCA TATGCTATTC TTTCTCtggg

2001  GAACTGGAAC TATTTTGCAG CAATGCGCAA TGAGAAAAGA AATCCAAAAT

2051  TAGAAGCTAC ACATCTGGAG AAGGCCAAGG AACTCTATAC TAaagtCCTG

2101  ACTCAACATA ATTCCAACAT GTATGCTGCC AACGGTTCTG GCATTGTATT

2151  AGCAGAGAAA GGCCAATTTG ATATTGCCAA GGATGTTTTT ACTCaggtTC

2201  AAGAAGCTGC GAGCGGAAGT GTATTCTTC AGATGCCTGA TGTATGGGTG

2251  AATCTGGCTC ATGTTTACTT TGCTCAAGGG AATTTTGCCT TAACCGTGAA

2301  AATGGTTTGT CATTTTATAT AGcgttttt ttttttttaa attcttttgg 2351  ttgatttcga tgttttgctt aagtactctg ttcattatct atgttgttgg 2401  cagtatcaaa actgcttgcg aaagttcttt tacaacacag actcccaaat 2451  ccttctttac ttagcccgta cccattatga ggctgagcag tggcaagagt
```

Figure 14, continued

```
2501  gcaaaaagac actattaagg gccattcact tgactccttc aaattacaca
2551  ttcagatttg atttgggtgc tgtaatgcaa aaatcatcgt cttccacact
2601  gcaaagaaa aaaagaacag ctgatgAGGT gcgctcaaca gttgcagaag
2651  cagagaatgc tgttcgtgta ttcactcaat tgtctgctgc ttcagacctc
2701  catgttcatg ggtttgatag caagaaaata caaacccatg ttcagtattg
2751  ctcgcacttg ctggaagcag caaagttca ccgtgaagct gctgagcagg
2801  aggagctgca gaaccgacag agattagaag ttgctcgtca ggctgctttg
2851  gcagaagaag cacgccgtaa agctgaagaa cagaggaaat atcAGTTgga
2901  gaaaagaaaa caggaggaag agctgagacg cctaaagcaa gaagaagaaa
2951  aatttcagcg tataaAGGAa caatggaaga gctccacacc tggatctaat
3001  aagcggaagg atagagtgga agatgatgat ggggaaagta agcccagtga
3051  gcggagaaga aagaagggtg gaaagagaag aaagaaggac aaaagctcaa
3101  gggctcgaca ctacgaggac gatgaagaag aagctgccac tatggatgat
3151  cataatgaag tggaagatga agacgccaac actaattata acagggaaga
3201  tgagatgact actcaagaag ctgaggaacc tgtggatgat gatgctcatg
3251  atcttctcgc tgctgctggg ctcgaagatc ctgatgttga tgatgatgAG
3301  GTacctactt cgggtgtaag gcgaagaagg gcgttatcgt catcagacga
3351  agaaggtgaa ttaatggagg agagtcatcc aaattcaagc ccccagaaag
3401  aaaagaaga gagcaatggg gaagctggtg atcctaacat ggaggaagaa
3451  gaggaagagg aagaggccaa ttgagagata tttcatacat aacaacagat
3501  atctcttgtg tgtttgtaac tttagtgaca aagatttcat tgattcaatt
3551  tctctagtag tcagagtgtg aagacaattt acattcacag gccaaggatg
3601  atcagtttgt attttgggtt atttggattg agccttgttt ttatttgcta
3651  ttgttactaa tagaaaagct tttttcttt
```

Figure 14, continued

Panel C: cDNA Sequence from cloned cDNA: Short Form (length: 3582)

```
   1  cgattcactt catcgttggc acacacacat actctctatt cgaaaaattc
  51  gccactgcaa tttcttctag ggtttctggt aatcctcact tagccgggca
 101  atggcgagtg tgtacatacc ggttcagaat tcagaagaag aagttagggt
 151  tgttcttgat cagctccctc gtgacgcttc tgatatactt gatattctta
 201  aagccgaaca agctcctctc gatctctggc tcatcatcgC GAGggagtac
 251  ttcaaacaag gaaaaattga acagtttcga caaatattgg aggaagggtc
 301  aagttcTGAC attgacgagt actatgccga tgttaagtac gagagaatag
 351  cgattttgaa tgctctaggt gcgtattata gctaccttgg taaaactgag
 401  accaaaaaca gagagaaaga ggagcaattt atctctgcca cacgatatta
 451  taacaaagca tcgagaatcg atatgcatga accttccact tgggttggga
 501  aAGGTcagct cttactggct aagggtgaaa tagataatgc tcttcaggca
 551  tttaagattg tgttagacac tgcccctgat aatgttcctg ctcttctggg
 601  tcAGGCttct gtagaattta atcgtggacg attttctgag tcattacaac
 651  tatacaAGAG ggccttgcaa gtatttcccg gttgtcctgc agctgtgaga
 701  ctgggaattg gttctttgtc gttataagtt ggggcaacta gataaagcac
 751  ggcaagcgtt tgatcgcgtt ttgcaggcAA ATcctgataa tgttgaggct
 801  cttgtggcac ttgggattAT GGATTTGCAA GCAAATGAtt ctATAGGAAT
 851  GAGGAAAGGA ATGGACAGAA TGCAGCAGGC ATTCGAGATT TATCCCTATT
 901  GCGCATCAGC CTTAAATTAT TTGGCCAATC ACTTTTTTTT CACCGGCCAG
 951  CACTTTCTTG TTGAGCAGCT GACTGAAACA GCATTAGCCG TCACAACTCA
1001  TGGGCCAACA AAGTCACATT CTTTTTACAA TTTAGCACGG TCATATCATA
1051  GCAagggGGA CTTTGAAAAG GCTGGGATGT ACTATATGGC AGCCATCAAA
1101  GAAACTAATA ATAACCCACA CGAATTTGTA TTTCCTTACT TtggtTTGGG
1151  TCAAGTACAA CTAAAGTTGG GGGAGCTTAA AGGATCTGTA TTTAATTTTG
```

Figure 14, continued

```
1201  AGAAAGTATT AGAAGTTTAT CCTGACAACT GCGAGACTTT GAaggcTCTC
1251  GGGCACTTAT ACACCCAGCT TGGACAAAAT GAGAAGGCCC TTGAGTACAT
1301  GCGAAAGGCC ACAAAACTTG ATCCACGTGA TGCCCaggcA TTTGTTGGCC
1351  TTGGTGAGCT GCTGATATCA TCTGACACGG GAGCCGCCCT TGACGCCTTC
1401  AAAAtggcAC GGACGCTCAT GAAAAAGGA GGGCAAGAAG TGCCTATAGA
1451  AGTCCTGAAT GACATCGGTG CTTTACATTT TGAGAGAGAA GAATTTGagt
1501  cTGCGCTTGA GAATTTTAAG GAGGCTCTGG GTGATGGAAT ATGGATTAGC
1551  TTCCTTGATG AAAAGAAAA TTTGGAACAG ACAGGTGTAT CTGTTCTCGG
1601  GTACAAGGAC ACGGGCATTT CCATAGGCT GATTGAAAGT GGTCACTCTG
1651  TCGATGTACC TTGGAATAAA GTTACAACTT TGTTTAACCT GGCTAGATTA
1701  CTTGAACAGA TACACAAAAC AGAAGCAGCG ACTTTTATGT ATCGGTTGAT
1751  ACTTTTCAag taTCCTGGCT ACATAGATGC TTATTTGAGG CTTGCTGCAA
1801  GTGCAAAAGC TCAGAACAAT CTTCCTCTGG CCATTGAACt ggtGAATGAA
1851  GCTCTGAAAG TGGACGATAA AAATCCAAAT GCTTTGTCTC TACTTGGTGA
1901  ATTGGAGCTT AAGAACGATG ACTGGGTTAA GGCAAAGGAA ACCTTTCGAG
1951  CTGCTAATGA TGCAACTGAT GGGAAGGACT CATATGCTAT TCTTTCTCtg
2001  ggGAACTGGA ACTATTTTGC AGCAATGCGC AATGAGAAAA GAAATCCAAA
2051  ATTAGAAGCT ACACATCTGG AGAAGGCCAA GGAACTCTAT ACTAaagtCC
2101  TGACTCAACA TAATTCCAAC ATGTATGCTG CCAACGGTTC TGGCATTGTA
2151  TTAGCAGAGA AAGGCCAATT TGATATTGCC AAGGATGTTT TTACTCaggt
2201  TCAAGAAGCT GCGAGCGGAA GTGTATTTCT TCAGATGCCT GATGTATGGG
2251  TGAATCTGGC TCATGTTTAC TTTGCTCAAG GAATTTTGC CTTAACCGTG
2301  AAAATGtatc aaaactgctt gcgaaagttc ttttacaaca cagactccca
2351  aatccttctt tacttagccc gtacccatta tgaggctgag cagtggcaag
2401  agtgcaaaaa gacactatta agggccattc acttgactcc ttcaaattac
2451  acattcagat ttgatttggg tgctgtaatg caaaaatcat cgtcttccac
```

Figure 14, continued

```
2501  actgcaaaag aaaaaaagaa cagctgatgA GGTgcgctca acagttgcag 2551  aagcagagaa tgctgttcgt gtattcactc aattgtctgc tgcttcagac 2601  ctccatgttc atgggtttga tagcaagaaa atacaaaccc atgttcagta 2651  ttgctcgcac ttgctggaag cagcaaaagt tcaccgtgaa gctgctgagc 2701  aggaggagct gcagaaccga cagagattag aagttgctcg tcaggctgct 2751  ttggcagaag aagcacgccg taaagctgaa gaacagagga aatatcAGTT 2801  ggagaaaaga aaacaggagg aagagctgag acgcctaaag caagaagaag 2851  aaaaatttca gcgtataaAG GAacaatgga agagctccac acctggatct 2901  aataagcgga aggatagagt ggaagatgat gatggggaaa gtaagcccag 2951  tgagcggaga agaaagaagg gtggaagag aagaagaag gacaaaagct 3001  caagggctcg acactacgag gacgatgaag aagaagctgc cactatggat 3051  gatcataatg aagtggaaga tgaagacgcc aacactaatt ataacaggga 3101  agatgagatg actactcaag aagctgagga acctgtggat gatgatgctc 3151  atgatcttct cgctgctgct gggctcgaag atcctgatgt tgatgatgat 3201  gAGGTaccta cttcgggtgt aaggcgaaga agggcgttat cgtcatcaga 3251  cgaagaaggt gaattaatgg aggagagtca tccaaattca gcccccaga 3301  aagaaaaga agagagcaat ggggaagctg gtgatcctaa catggaggaa 3351  gaagaggaag aggaagaggc caattgagag atatttcata cataacaaca 3401  gatatctctt gtgtgtttgt aactttagtg acaaagattt cattgattca 3451  atttctctag tagtcagagt gtgaagacaa tttacattca caggccaagg 3501  atgatcagtt tgtattttgg gttatttgga ttgagccttg tttttatttg 3551  ctattgttac taatagaaaa gcttttttct tt
```

Figure 14, continued

Panel D: cDNA Sequence from AGI (length: 1506)

```
ATGGATTTGCAAGCAAATGATTCTATAGGAATGAGGAAAGGAATGGACAGAATGCAGCAGGCATTCGAGAT
TTATCCCTATTGCGCATCAGCCTTAAATTATTTGGCCAATCACTTTTTTTTCACCGGCCAGCACTTTCTTG
TTGAGCAGCTGACTGAAACAGCATTAGCCGTCACAACTCATGGGCCAACAAAGTCACATTCTTTTTACAAT
TTAGCACGGTCATATCATAGCAAGGGGGACTTTGAAAAGGCTGGGATGTACTATATGGCAGCCATCAAAGA
AACTAATAATAACCCACACGAATTTGTATTTCCTTACTTTGGTTTGGGTCAAGTACAACTAAAGTTGGGGG
AGCTTAAAGGATCTGTATTTAATTTTGAGAAAGTATTAGAAGTTTATCCTGACAACTGCGAGACTTTGAAG
GCTCTCGGGCACTTATACACCCAGCTTGGACAAAATGAGAAGGCCCTTGAGTACATGCGAAAGGCCACAAA
ACTTGATCCACGTGATGCCCAGGCATTTGTTGGCCTTGGTGAGCTGCTGATATCATCTGACACGGGAGCCG
CCCTTGACGCCTTCAAAATGGCACGGACGCTCATGAAAAAAGGAGGGCAAGAAGTGCCTATAGAAGTCCTG
AATGACATCGGTGCTTTACATTTTGAGAGAGAAGAATTTGAGTCTGCGCTTGAGAATTTTAAGGAGGCTCT
GGGTGATGGAATATGGATTAGCTTCCTTGATCAAAAAGAAAATTTGGAACAGACAGGTGTATCTGTTCTCG
GGTACAAGGACACGGGCATTTTCCATAGGCTGATTGAAAGTGGTCACTCTGTCGATGTACCTTGGAATAAA
GTTACAACTTTGTTTAACCTGGCTAGATTACTTGAACAGATACACAAAACAGAAGCAGCGACTTTTATGTA
TCGGTTGATACTTTTCAAGTATCCTGGCTACATAGATGCTTATTTGAGGCTTGCTGCAAGTGCAAAAGCTC
AGAACAATCTTCCTCTGGCCATTGAACTGGTGAATGAAGCTCTGAAAGTGGACGATAAAAATCCAAATGCT
TTGTCTCTACTTGGTGAATTGGAGCTTAAGAACGATGACTGGGTTAAGGCAAAGGAAACCTTTCGAGCTGC
TAATGATGCAACTGATGGGAAGGACTCATATGCTATTCTTTCTCTGGGGAACTGGAACTATTTTGCAGCAA
TGCGCAATGAGAAAAGAAATCCAAAATTAGAAGCTACACATCTGGAGAAGGCCAAGGAACTCTATACTAAA
GTCCTGACTCAACATAATTCCAACATGTATGCTGCCAACGGTTCTGGCATTGTATTAGCAGAGAAAGGCCA
ATTTGATATTGCCAAGGATGTTTTTACTCAGGTTCAAGAAGCTGCGAGCGGAAGTGTATTTCTTCAGATGC
CTGATGTATGGGTGAATCTGGCTCATGTTTACTTTGCTCAAGGGAATTTTGCCTTAACCGTGAAAATGGTT
TGTCATTTTATATAG
```

Figure 15

VIP6 Amino Acid Sequence

Sequence and annotation of the AT2G06210.1 (*VIP6*) region

Panel A: Amino Acid Sequence from cloned cDNA, Short Form (length: 1193)

MDLQANDSIGMRKGMDRMQQAFEIYPYCASALNYLANHFFFTGQHFLVEQLTETALAVTTHGPTKSHSFYN
LARSYHSKGDFEKAGMYYMAAIKETNNNPHEFVFPYFGLGQVQLKLGELKGSVFNFEKVLEVYPDNCETLK
ALGHLYTQLGQNEKALEYMRKATKLDPRDAQAFVGLGELLISSDTGAALDAFKMARTLMKKGGQEVPIEVL
NDIGALHFEREEFESALENFKEALGDGIWISFLDEKENLEQTGVSVLGYKDTGIFHRLIESGHSVDVPWNK
VTTLFNLARLLEQIHKTEAATFMYRLILFKYPGYIDAYLRLAASAKAQNNLPLAIELVNEALKVDDKNPNA
LSLLGELELKNDDWVKAKETFRAANDATDGKDSYAILSLGNWNYFAAMRNEKRNPKLEATHLEKAKELYTK
VLTQHNSNMYAANGSGIVLAEKGQFDIAKDVFTQVQEAASGSVFLQMPDVWVNLAHVYFAQGNFALTVKMY
QNCLRKFFYNTDSQILLYLARTHYEAEQWQECKKTLLRAIHLTPSNYTFRFDLGAVMQKSSSSTLQKKKRT
ADEVRSTVAEAENAVRVFTQLSAASDLHVHGFDSKKIQTHVQYCSHLLEAAKVHREAAEQEELQNRQRLEV
ARQAALAEEARRKAEEQRKYQLEKRKQEBEELRRLKQEEEKFQRIKEQWKSSTPGSNKRKDRVEDDDGESKP
SERRRKKGGKRRKKDKSSRARHYEDDEEEAATMDDHNEVEDEDANTNYNREDEMTTQEAEEPVDDDAHDLL
AAAGLEDPDVDDDEVPTSGVRRRRALSSSDEEGELMEESHPNSSPQKEKEESNGEAGDPNMEEEEEEEAN

Panel B: Amino Acid Sequence from cloned cDNA, Long form

MDLQANDSIGMRKGMDRMQQAFEIYPYCASALNYLANHFFFTGQHFLVEQLTETALAVTTHGPTKSHSFYN
LARSYHSKGDFEKAGMYYMAAIKETNNNPHEFVFPYFGLGQVQLKLGELKGSVFNFEKVLEVYPDNCETLK
ALGHLYTQLGQNEKALEYMRKATKLDPRDAQAFVGLGELLISSDTGAALDAFKMARTLMKKGGQEVPIEVL
NDIGALHFEREEFESALENFKEALGDGIWISFLDEKENLEQTGVSVLGYKDTGIFHRLIESGHSVDVPWNK
VTTLFNLARLLEQIHKTEAATFMYRLILFKYPGYIDAYLRLAASAKAQNNLPLAIELVNEALKVDDKNPNA
LSLLGELELKNDDWVKAKETFRAANDATDGKDSYAILSLGNWNYFAAMRNEKRNPKLEATHLEKAKELYTK
VLTQHNSNMYAANGSGIVLAEKGQFDIAKDVFTQVQEAASGSVFLQMPDVWVNLAHVYFAQGNFALTVKMV
CHFI

Figure 15, continued

Panel C: Amino Acid Sequence from predicted cDNA from AGI

MDLQANDSIGMRKGMDRMQQAFEIYPYCASALNYLANHFFFTGQHFLVEQLTETALAVTTHGPTKSHSFYN
LARSYHSKGDFEKAGMYYMAAIKETNNNPHEFVFPYFGLGQVQLKLGELKGSVFNFEKVLEVYPDNCETLK
ALGHLYTQLGQNEKALEYMRKATKLDPRDAQAFVGLGELLISSDTGAALDAFKMARTLMKKGGQEVPIEVL
NDIGALHFEREEFESALENFKEALGDGIWISFLDEKENLEQTGVSVLGYKDTGIFHRLIESGHSVDVPWNK
VTTLFNLARLLEQIHKTEAATFMYRLILFKYPGYIDAYLRLAASAKAQNNLPLAIELVNEALKVDDKNPNA
LSLLGELELKNDDWVKAKETFRAANDATDGKDSYAILSLGNWNYFAAMRNEKRNPKLEATHLEKAKELYTK
VLTQHNSNMYAANGSGIVLAEKGQFDIAKDVFTQVQEAASGSVFLQMPDVWVNLAHVYFAQGNFALTVKMV
CHFI

SEQUENCE LISTING

<160> NUMBER OF SEQ ID NOS: 39

<210> SEQ ID NO 1
<211> LENGTH: 2113
<212> TYPE: DNA
<213> ORGANISM: Arabidopsis thaliana

<400> SEQUENCE: 1

| gcccgtaaaa | ttcaaagacg | agagctaaaa | gcgatctcaa | tcgattaaaa | ttaaataaca | 60 |
| gagagaccac | gagagcagag | aagacgcaag | aagaagagtg | aagaaaggtg | tcgtagtcgg | 120 |
| atcactgaga | cgtggcggct | ccagagagta | cttctccgca | attagctgac | gacggcggga | 180 |
| gagtgaggaa | gaagatatta | atgggcctgt | tacgatatta | atgggccttt | agtagtaaac | 240 |
| aagaatacgg | aacgatgtta | aacactctat | tgtttccaac | tactaaaaac | gacgcgagtt | 300 |
| tctattttat | aactaaaaaa | cgagaatcaa | agtctctgtt | tcaaatttgg | gtcttttgct | 360 |
| tcttcttgct | cacttgagga | aacacagtaa | aaacctaaaa | agagaatgaa | actcgcaggt | 420 |
| ctgaaatcga | tcgagaacgc | tcacgaagat | tccgtttggg | cagcgacgtg | ggttccggcg | 480 |
| acggaagatc | gaccggcgtt | gcttctgact | ggatctcttg | acgagacggt | gaagttatgg | 540 |
| cgaccggacg | agctggatct | tgtgcggact | aatactggac | actctttggg | agtagcagct | 600 |
| ttggctgcgc | atccttctgg | gattattgca | gcatcttctt | cgattgatag | ctttgtccgt | 660 |
| gtgtttgatg | ttgatactaa | tgctacgatt | gctgttttgg | aagctcctcc | ttctgaggtt | 720 |
| tggggaatgc | aatttgaacc | taaggtaatt | gactcaatga | gattgcctcc | aattttaggg | 780 |
| ttttgaagga | ttttgggttg | ttttgtggtg | aaagaattcg | attgcttcat | tgaatttcac | 840 |
| ttcttagttg | cgagtaatgc | ttctcctgat | ctatataaca | atgcttgggt | actatatgga | 900 |
| attgctgagt | atcgtttgaa | tctgtagctc | tgatcagata | gggtcatcta | ctctgctcgg | 960 |
| aaaatagatc | tagatcatct | tctgattttt | cattgagtct | tatatagtag | attaagaaca | 1020 |
| atttattggt | gctttgatga | taaatcttga | tttggtatga | tagaattttg | acctggtgac | 1080 |
| tatcaagtat | cagtgcaatg | atctctcttt | tagtttgcag | tggagttttt | atttgcttct | 1140 |
| gagcttataa | tttcaacatt | actctttaga | atggtgctct | gctaacatag | tattttacat | 1200 |
| gttccaaggg | tacgatcctt | gctgttgcag | gtggaagtag | tgcctcagtc | aagctttggg | 1260 |
| acactgcaag | ctggagatta | atctcaactc | tatcaatccc | acgcccagat | gcaccaaaac | 1320 |
| cttccgataa | aaccagcagc | aagaaattcg | ttctctcggt | ggcttggtct | cctaatggga | 1380 |
| aacgacttgc | ttgtggttca | atggatggta | cgatctgtgt | ttttgatgtt | gaccgctcaa | 1440 |
| agctacttca | ccagctagaa | ggtcacaata | tgcctgtaag | gtcccttgtg | ttctcccctg | 1500 |
| tagacccgag | agtcctcttc | tctggatcag | atgatgggca | tgtgaacatg | cacgatgcag | 1560 |
| aagggaaaac | gctgttgggg | tccatgtcag | ggcacacgag | ttgggtgctg | agcgttgatg | 1620 |
| ctagcccaga | cggtggagcc | atagcaaccg | gctcaagcga | tagaactgtg | aggctatggg | 1680 |
| atcttaaaat | gagagctgcg | attcagacaa | tgagcaacca | caatgaccag | gtttggtctg | 1740 |
| tggcctttag | accaccaggt | ggaaccggtg | tccgggctgg | tcgacttgct | agtgtctctg | 1800 |
| atgacaagag | tgtatcgctc | tatgattact | catgaacaat | tcggtttttt | gacttttttc | 1860 |
| ttttatgcat | tctccaagac | gcatctagtt | gtaacaatat | aatctgcaac | aggttgattt | 1920 |
| tgaccggagt | ctttagattt | atcgcttaca | caaaaaacaa | agaagataaa | atgattcaaa | 1980 |
| ctttgcgata | gaactttatt | ggaaaactga | gaaacagata | aagatcacag | agagatgagt | 2040 |

```
tgaagagtaa cgcaaacaaa cgtctaaaag ttttcaaaaa acaaaacagc taaagattat    2100
ggtcttgtct ctt                                                       2113

<210> SEQ ID NO 2
<211> LENGTH: 5220
<212> TYPE: DNA
<213> ORGANISM: Arabidopsis thaliana

<400> SEQUENCE: 2
attggttttt ttttttttgg ccaggatacg aaactcatct tagtttcgga ttgttatttg      60
gggtttgaac aagaacactc cattgaacaa cttgcacgac gcggatgagc cattagatga     120
tggattgtag taaccccata ttttttttgga atttgtttta tatattgtca aaattttctt    180
aaaattctgg ttttttttttg tcgtcttctt aatgtaaaac caaattttac cttacgtttt    240
gtaataaaac agtgttacag atcttttgag atacataaga aaaataatga agagcttaag     300
gtaaatgtgt taattttaca taacgttatg tagaacagtg ttacaaaaaa attgggctac     360
atgactacat aataaattaa tcaagagatt aaaactaaat gtgtttactc tgtgacagtc     420
tgtttggtaa atttgtttgg gtcaacaagt ttacgttatt ttgaactatc tccatatcaa     480
attaccaatt attcattaca gttacagaag ggaaataaaa tccattatta catgaattta     540
aaaaaatcat gattctgtct ttattttgat taaaacgagt ctaattccag actacattat     600
aacaaatgga cgaaaggaga gtgaaagatt tgacgaacat gattaatctt cgtcactgtc     660
atcaatcacg gccttacgac gatgagtcgg agcttttcta ggcggagact cctcctcgtc     720
agactcaatc cctttccttt tccggccact tccacggtga tccttctctg ccctacctcc     780
ctgcataaac cacatttcac cacacattac aatctcaatg aacttcctca ttgacaacaa     840
taaaaatgga agaacattct aatttgcgta ccgcaaccte ttcctcttct tcatcttcat     900
ctgagtatct gttagatttt cctcgttcct cttcatcttc ttctgcatct tcctcatatt     960
catcttctga atccttgccc cttccacggg ccggtgactt ttcttcctct tcttcttccg    1020
tctcatattc tgattcctct ctctcactct cagaatactc catttgacgt cttgacggtc    1080
tggccgaagt cattgaagac ctccccggaa tgcctttgtg gctctggttt taccccagtg    1140
agaagcagtt gaatattagt tcaatttcta atgcttttt tgcattccga gatatatgag    1200
tttttgtttt gtttaccttc ttggcgttta gaatccggcg ttcccgttgc gcttcagctt    1260
cgagatcttc ctcatagcca cggtttgagc ggtaatcctc gtcatcctgg ttccaagaaa    1320
caatcagtcg ttactagtgc aatctttgct ttagaaaatg gaagaaccca atatacacaa    1380
actaatcaaa cagacctcat caagagcatc ttccaagtag ccagtggaaa gttgtctcct    1440
ttcaacagga agtggatact tgcgcttgat tttctccctc gcctgactca gctttgtact    1500
agccttgagg ttttggctttt ccgccttcag aatttgagat attaaatgag aaaagtctac    1560
aaacactgca ataaaactat tgttggattg tctgagctca attaagaggt aacctttttct    1620 ctcttctcct tctccctctc agggtcaatg tcagtgacac agttcttaac tttgaaggcc    1680
ttcttctgcc tcgattcaac aatggcagtc aagagcctat gggaatttga cgtcagcgat    1740 gatgggggtaa atctcatttt cttcaaaatt cttccttgtg attgaaggat ccctacacc    1800 aacatccaaa taagacaaca ctttgagata tagcagagtg gaatgcagg agacatttgg    1860 tttcctaatg agaagttttg tcatttagta tagagaatcg tatgggtgct ctaaaatgaa    1920
tcagtgtatc taggaggctg gagcaactac aaattgatcg ctaactaagg cagaaggaat    1980
```

-continued

```
gacgaagtaa caccttttca tgtttgataa agaggtgatt ctggtcttct tttgcatctt    2040
gttcagttat gttaagaact tcgtttccta tcaatagctg taagcttcca tctgaccacc    2100
ttacaaaccg agcattactt tcactctgca tacgaatata gagtgacttg agtttactac    2160
agcaaaagta acggaaaaag tagaagaaat gtgtgcaata agcaacaaaa ccaagaattc    2220
ttgtttatgg gcagatttct aatgaagcct aaagaataag aagaactgtt gaacagagat    2280
atcataaaat ttcatctcca actatatgaa cacatgtccg tagtgaaaag cacaaagtaa    2340
actaattcgg aatacataaa ttgcatcaaa agtatgtact tataatacat cattgcatca    2400
gaagtactag taataggcaa actacatagc ttcattgcag gtttgatgga aaatttaaaa    2460
gcagaaaagc tttgaagaag tgttcactta catatgtttt gccatctcga ctcttaacaa    2520
acctatggcg aacaatatta ttgtccaaac ggatacgatt ctttgctccg ggttcatctg    2580
tcatgaatgt gtcttcttca acgaatgttt tggcatcaaa aggctttgga tcaatcccca    2640
tgatattgga aactttttatc atgttcatct gaaaaagatc aaagagaaaa cggtatatga    2700
ggaagcgcaa ttttgctaca gaacatcttc actacagata gacaactaga aaatggggtt    2760
tcagatataa aacagaatag cacgctcatg tacaccaaat ggcccttcat gctaagtaaa    2820
tgtagaagca tgtttcagtg caatggttct ccacataaaa gacatcagat actcactctt    2880
cgaaccacaa tgatatgaga gattttggta acttggaaat accagaaagg aaactattga    2940
tttgaagcca tgtcagcgaa taatctttta gcaacataaa gcaggtatac cttaacgggg    3000
tcacctggag gagggcggaa aggaacctcc acttccaaag ggggaccaac tggcctctcc    3060
ctgtacctag cttcaacatg ttcagcttct gactcgtatt gaggatcttc ttcagggatt    3120
atatcatcaa gcaccatatc atcgggtctc agatccttct cagagccctc ttcatcttcg    3180
attggcgatc tctacaaaat tagacatctc atcatacata catgcaattt catatggttt    3240
ctaaaaggaa gcaaacactg gaaaggaaac agatattctg taaactgaaa tgtaatatta    3300
gatgcaagac tcacatgttc atcctgctca acgtcattcc gaacatattc ttctgcgtct    3360
tcatcatccg aagatccgaa aacattacga atatttacgt ctgactgtgc aacttgaacc    3420
tcttccttct cctcactagg tgatctaccc accacgccat atttccatgt acaaaagaca    3480
aagtgatcca taagaaattt gaaaatccaa ggaacctcag aggactagca agtattatta    3540
aatccagagc acagaaaaga tcaaaagaa gctatgaaac agctaggaaa aaaaagaatg    3600 gaaaagggg tacctggac tcctagtctg atcaacctct tcatcttcag actcataatg    3660
cttttcacca gacctctctg atccgctctc aacaacctcc tgtctcctct ttttggctac    3720 tctacccca tgttcttctt ctttgttatc actatcacta tctcttgctt cactttcctc    3780
ttgtggatca gcctcctgtg aactttgctc cctctcaccc tcactttctc caggatcaag    3840
ttctacatct ccctgttccc cgtcagactc agcttcagct tctccgtgaa cttcaacctc    3900
agcttcacct tctccttcag gctccacccc gccctcagcc tcatcctatc agtgtttaca    3960
ttggaaattt cagccacaat ttcactgata tcttagtcta gttgatatta agaagaactg    4020
aagctgaatt aggcctaata agttgcattg gttcctgcaa ttaacctaaa accctaaatt    4080
caagcgagaa gaactccaga aaccattcgt attccaaggt gtaattgaag aacagtggca    4140
gtgaaaaata cgaaaactga acaatcaat agtgacgaaa cgaaggagat aaagatggag    4200
agagttacgg aagcgtagtt aggctgacga cgattgcatt catgttcgga ttcgatctct    4260
tcttcctcgg aattatctcc gaacagatta agcatcatct cggatctctt ttctcctta    4320 accatcttcg cctcacttac tcaaaagtca ctgcctctta gctggtgacg gcggctcgtg    4380
```

```
atctgagctc cgacgaaggg ttcactgtta tcggcctttg ttgaagaagc tatttttttt    4440
tcatctctac ctcgcgattt tatggcatca gaattattat tattaaaaac aattgttaca    4500
acttacaaag aaaaggaaat tttcatcgat atatctttt  taacgcatta ccggattatt    4560
aaaaatcatt tttttacgt  gtaacgacga ctagagaggg aaaaaagatg ggattttatg    4620
ggcttttttg agattggaat tcaatatttt tggcccacaa attttgggtt atggatacca    4680
gtttctttgt gatagtgagc ttgtgtttgc cttggcccct atgtatatga atgatacaac    4740 atcctttta  ctgattcttt tggcccctat ttttttatat ttaatttatt ttaaaaacta    4800
attattaact tctttgatca ataaacttga gttgccaaaa taaatgttat gtcttcttct    4860
aaaacattgt tgttggttta tagattttat ctgctttaga aattaacaag agacaaagat    4920
taggtaaaag cataaccgac ttgtgttcta tgaaaactta agtgacaact aaacatcatg    4980
aatattcagg aaatcctgaa aatttaaaca gaattatagt aatttctgaa aaactcaaga    5040
aattatggaa taaaagaaa  aagaaaaaa  ctatggacac ttttaaatta ctcaaactag    5100
tttaaggctt ttggaaattt cacttttttgc ttttttttaa ctcgagaaaa ttacaattt    5160 atgtagacac attttgctca caaatgttta tttatatatt ttccataaat ttattttca    5220

<210> SEQ ID NO 3
<211> LENGTH: 1498
<212> TYPE: DNA
<213> ORGANISM: Arabidopsis thaliana

<400> SEQUENCE: 3
gtaaaaacct aaaagagaa  tgaaactcgc aggtctgaaa tcgatcgaga acgctcacga      60
agattccgtt tgggcagcga cgtgggtcc  ggcgacggaa gatcgaccgg cgttgcttct     120
gactggatct cttgacgaga cggtgaagtt atggcgaccg gacgagctgg atcttgtgcg     180
gactaatact ggacactctt tgggagtagc agctttggct gcgcatcctt ctgggattat     240
tgcagcatct tcttcgattg atagctttgt ccgtgtgttt gatgttgata ctaatgctac     300
gattgctgtt ttggaagctc ctccttctga ggtttgggga atgcaatttg aacctaaggt     360
aattgactca atgagattgc ctccaatttt agggttttga aggattttgg gttgttttgt     420
ggtgaaagaa ttcgattgct tcattgaatt tcacttctta gttgcgagta atgcttctcc     480
tgatctatat aacaatgctt gggtactata tggaattgct gagtatcgtt tgaatctgta     540
gctctgatca gatagggtca tctactctgc tcggaaaata gatctagatc atcttctgat     600
ttttcattga gtcttatata gtagattaag aacaatttat tggtgctttg atgataaatc     660
ttgatttggt atgatagaat tttgacctgg tgactatcaa gtatcagtgc aatgatctct     720
cttttagttt gcagtggagt ttttatttgc ttctgagctt ataatttcaa cattactctt     780
tagaatggtg ctctgctaac atagtatttt acatgttcca agggtacgat ccttgctgtt     840
gcaggtggaa gtagtgcctc agtcaagctt tgggacactg caagctggag attaatctca     900
actctatcaa tcccacgccc agatgcacca aaaccttccg ataaaccag  cagcaagaaa     960 ttcgttctct cggtggcttg gtctcctaat gggaaacgac ttgcttgtgg ttcaatggat    1020
ggtacgatct gtgtttttga tgttgaccgc tcaaagctac ttcaccagct agaaggtcac    1080
aatatgcctg taaggtccct tgtgttctcc cctgtagacc cgagagtcct cttctctgga    1140
tcagatgatg ggcatgtgaa catgcacgat gcagaaggga aaacgctgtt ggggtccatg    1200
tcagggcaca cgagttgggt gctgagcgtt gatgctagcc cagacggtgg agccatagca    1260
```

-continued

| | |
|---|---|
| accggctcaa gcgatagaac tgtgaggcta tgggatctta aaatgagagc tgcgattcag | 1320 |
| acaatgagca accacaatga ccaggtttgg tctgtggcct ttagaccacc aggtggaacc | 1380 |
| ggtgtccggg ctggtcgact tgctagtgtc tctgatgaca agagtgtatc gctctatgat | 1440 |
| tactcatgaa caattcggtt ttttgacttt tttcttttat gcattctcca agacgcat | 1498 |

<210> SEQ ID NO 4
<211> LENGTH: 4065
<212> TYPE: DNA
<213> ORGANISM: Arabidopsis thaliana

<400> SEQUENCE: 4

| | |
|---|---|
| attttgaact atctccatat caaattacca attattcatt acagttacag aagggaaata | 60 |
| aaatccatta ttcatgaat ttaaaaaaat catgattctg tctttatttt gattaaaacg | 120 |
| agtctaattc cagactacat tataacaaat ggacgaaagg agagtgaaag atttgacgaa | 180 |
| catgattaat cttcgtcact gtcatcaatc acggccttac gacgatgagt cggagctttt | 240 |
| ctaggcggag actcctcctc gtcagactca atccctttcc ttttccggcc acttccacgg | 300 |
| tgatccttct ctgccctacc tccctgcata aaccacattt caccacacat tacaatctca | 360 |
| atgaacttcc tcattgacaa caataaaaat ggaagaacat tctaatttgc gtaccgcaac | 420 |
| ctcttcctct tcttcatctt catctgagta tctgttagat tttcctcgtt cctcttcatc | 480 |
| ttcttctgca tcttcctcat attcatcttc tgaatccttg ccccttccac gggccggtga | 540 |
| cttttcttcc tcttcttctt ccgtctcata ttctgattcc tctctctcac tctcagaata | 600 |
| ctccatttga cgtcttgacg gtctggccga agtcattgaa gacctccccg gaatgccttt | 660 |
| gtggctctgg ttttacccca gtgagaagca gttgaatatt agttcaattt ctaatgcttt | 720 |
| ttttgcattc cgagatatat gagttttgt tttgtttacc ttcttggcgt ttagaatccg | 780 |
| gcgttcccgt tgcgcttcag cttcgagatc ttcctcatag ccacggtttg agcggtaatc | 840 |
| ctcgtcatcc tggttccaag aaacaatcag tcgttactag tgcaatcttt gctttagaaa | 900 |
| atggaagaac ccaatataca caaactaatc aaacagacct catcaagagc atcttccaag | 960 |
| tagccagtgg aaagttgtct cctttcaaca ggaagtggat acttgcgctt gattttctcc | 1020 |
| ctcgcctgac tcagctttgt actagccttg aggttttggc tttccgcctt cagaatttga | 1080 |
| gatattaaat gagaaaagtc tacaaacact gcaataaaac tattgttgga ttgtctgagc | 1140 |
| tcaattaaga ggtaaccttt tctctcttct ccttctccct ctcagggtca atgtcagtga | 1200 |
| cacagttctt aactttgaag gccttcttct gcctcgattc aacaatggca gtcaagagcc | 1260 |
| tatgggaatt tgacgtcagc gatgatgggg taaatctcat tttcttcaaa attcttcctt | 1320 |
| gtgattgaag ataccctac accaacatcc aaataagaca acactttgag atatagcaga | 1380 |
| gttggaatgc aggagacatt tggtttccta atgagaagtt ttgtcattta gtatagagaa | 1440 |
| tcgtatgggt gctctaaaat gaatcagtgt atctaggagg ctggagcaac tacaaattga | 1500 |
| tcgctaacta aggcagaagg aatgacgaag taacacccttt tcatgtttga taaagaggtg | 1560 |
| attctggtct tcttttgcat cttgttcagt tatgttaaga acttcgtttc ctatcaatag | 1620 |
| ctgtaagctt ccatctgacc accttacaaa ccgagcatta ctttcactct gcatacgaat | 1680 |
| atagagtgac ttgagtttac tacagcaaaa gtaacgaaaa aagtagaaga aatgtgtgca | 1740 |
| ataagcaaca aaaccaagaa ttcttgttta tgggcagatt tctaatgaag cctaaagaat | 1800 |
| aagaagaact gttgaacaga gatatcataa aatttcatct ccaactatat gaacacatgt | 1860 |
| ccgtagtgaa aagcacaaag taaactaatt cggaatacat aaaattgcatc aaaagtatgt | 1920 |

```
acttataata catcattgca tcagaagtac tagtaatagg caaactacat agcttcattg    1980
caggtttgat ggaaaattta aaagcagaaa agctttgaag aagtgttcac ttacatatgt    2040
tttgccatct cgactcttaa caaacctatg gcgaacaata ttattgtcca aacggatacg    2100
attctttgct ccgggttcat ctgtcatgaa tgtgtcttct tcaacgaatg ttttggcatc    2160
aaaaggcttt ggatcaatcc ccatgatatt ggaaactttt atcatgttca tctgaaaaag    2220
atcaaagaga aacggtata tgaggaagcg caattttgct acagaacatc ttcactacag     2280
atagacaact agaaaatggg gtttcagata taaaacagaa tagcacgctc atgtacacca    2340
aatggcccct catgctaagt aaatgtagaa gcatgtttca gtgcaatggt tctccacata    2400
aaagacatca gatactcact cttcgaacca caatgatatg agagattttg gtaacttgga    2460
aataccagaa aggaaactat tgatttgaag ccatgtcagc gaataatctt ttagcaacat    2520
aaagcaggta taccttaacg gggtcacctg gaggagggcg gaaaggaacc tccacttcca    2580 aaggggggacc aactggcctc tccctgtacc tagcttcaac atgttcagct tctgactcgt    2640
attgaggatc ttcttcaggg attatatcat caagcaccat atcatcgggt ctcagatcct    2700
tctcagagcc ctcttcatct tcgattggcg atctctacaa aattagacat ctcatcatac    2760
atacatgcaa tttcatatgg tttctaaaag gaagcaaaca ctggaaagga aacagatatt    2820
ctgtaaactg aaatgtaata ttagatgcaa gactcacatg ttcatcctgc tcaacgtcat    2880
tccgaacata ttcttctgcg tcttcatcat ccgaagatcc gaaaacatta cgaatattta    2940
cgtctgactg tgcaacttga acctcttcct tctcctcact aggtgatcta cccaccacgc    3000
catatttcca tgtacaaaag acaaagtgat ccataagaaa tttgaaaatc caaggaacct    3060
cagaggacta gcaagtatta ttaaatccag agcacgaaaa agatcaaaaa gaagctatga    3120
aacagctagg aaaaaaaaga atggaaaaag gggtaccttg gactcctagt ctgatcaacc    3180
tcttcatctt cagactcata atgctttttca ccagacctct ctgatccgct ctcaacaacc    3240
tcctgtctcc tcttttttggc tactctaccc ccatgttctt cttctttgtt atcactatca    3300
ctatctcttg cttcactttc ctcttgtgga tcagcctcct gtgaactttg ctccctctca    3360
ccctcacttt ctccaggatc aagttctaca tctccctgtt ccccgtcaga ctcagcttca    3420
gcttctccgt gaacttcaac ctcagcttca ccttctcctt caggctccac ccgccctca    3480 gcctcatcct atcagtgttt acattggaaa tttcagccac aatttcactg atatcttagt    3540
ctagttgata ttaagaagaa ctgaagctga attaggccta ataagttgca ttggttcctg    3600
caattaacct aaaaccctaa attcaagcga gaagaactcc agaaaccatt cgtattccaa    3660
ggtgtaattg aagaacagtg gcagtgaaaa atacgaaaac tgaaacaatc aatagtgacg    3720
aaacgaagga gataaagatg gagagagtta cggaagcgta gttaggctga cgacgattgc    3780
attcatgttc ggattcgatc tcttcttcct cggaattatc tccgaacaga ttaagcatca    3840
tctcggatct cttttctcct ttaaccatct tcgcctcact tactcaaaag tcactgcctc    3900
ttagctggtg acggcggctc gtgatctgag ctccgacgaa gggttcactg ttatcggcct    3960
ttgttgaaga agctatttt ttttcatctc tacctcgcga ttttatggca tcagaattat    4020
tattattaaa acaattgtt acaacttaca aagaaaagga aattt                     4065
```

<210> SEQ ID NO 5
<211> LENGTH: 321
<212> TYPE: PRT
<213> ORGANISM: Arabidopsis thaliana

```
<400> SEQUENCE: 5

Met Lys Leu Ala Gly Leu Lys Ser Ile Glu Asn Ala His Glu Asp Ser
1               5                   10                  15

Val Trp Ala Ala Thr Trp Val Pro Ala Thr Glu Asp Arg Pro Ala Leu
            20                  25                  30

Leu Leu Thr Gly Ser Leu Asp Glu Thr Val Lys Leu Trp Arg Pro Asp
        35                  40                  45

Glu Leu Asp Leu Val Arg Thr Asn Thr Gly His Ser Leu Gly Val Ala
50                  55                  60

Ala Leu Ala Ala His Pro Ser Gly Ile Ile Ala Ala Ser Ser Ser Ile
65                  70                  75                  80

Asp Ser Phe Val Arg Val Phe Asp Val Asp Thr Asn Ala Thr Ile Ala
                85                  90                  95

Val Leu Glu Ala Pro Pro Ser Glu Val Trp Gly Met Gln Phe Glu Pro
            100                 105                 110

Lys Gly Thr Ile Leu Ala Val Ala Gly Ser Ser Ala Ser Val Lys
        115                 120                 125

Leu Trp Asp Thr Ala Ser Trp Arg Leu Ile Ser Thr Leu Ser Ile Pro
130                 135                 140

Arg Pro Asp Ala Pro Lys Pro Ser Asp Lys Thr Ser Lys Lys Phe
145                 150                 155                 160

Val Leu Ser Val Ala Trp Ser Pro Asn Gly Lys Arg Leu Ala Cys Gly
                165                 170                 175

Ser Met Asp Gly Thr Ile Cys Val Phe Asp Val Asp Arg Ser Lys Leu
            180                 185                 190

Leu His Gln Leu Glu Gly His Asn Met Pro Val Arg Ser Leu Val Phe
        195                 200                 205

Ser Pro Val Asp Pro Arg Val Leu Phe Ser Gly Ser Asp Gly His
210                 215                 220

Val Asn Met His Asp Ala Glu Gly Lys Thr Leu Leu Gly Ser Met Ser
225                 230                 235                 240

Gly His Thr Ser Trp Val Leu Ser Val Asp Ala Ser Pro Asp Gly Gly
                245                 250                 255

Ala Ile Ala Thr Gly Ser Ser Asp Arg Thr Val Arg Leu Trp Asp Leu
            260                 265                 270

Lys Met Arg Ala Ala Ile Gln Thr Met Ser Asn His Asn Asp Gln Val
        275                 280                 285

Trp Ser Val Ala Phe Arg Pro Pro Gly Gly Thr Gly Val Arg Ala Gly
290                 295                 300

Arg Leu Ala Ser Val Ser Asp Asp Lys Ser Val Ser Leu Tyr Asp Tyr
305                 310                 315                 320

Ser

<210> SEQ ID NO 6
<211> LENGTH: 625
<212> TYPE: PRT
<213> ORGANISM: Arabidopsis thaliana

<400> SEQUENCE: 6

Met Val Lys Gly Glu Lys Arg Ser Glu Met Met Leu Asn Leu Phe Gly
1               5                   10                  15

Asp Asn Ser Glu Glu Glu Ile Glu Ser Glu His Glu Cys Asn Arg
            20                  25                  30

Arg Gln Pro Asn Tyr Ala Ser Asp Glu Ala Glu Gly Gly Val Glu Pro
```

-continued

```
                35                  40                  45
Glu Gly Glu Gly Glu Ala Glu Val Glu Val His Gly Glu Ala Glu Ala
         50                  55                  60
Glu Ser Asp Gly Glu Gln Gly Asp Val Glu Leu Asp Pro Gly Glu Ser
 65                  70                  75                  80
Glu Gly Glu Arg Glu Gln Ser Ser Gln Glu Ala Asp Pro Gln Glu Glu
                 85                  90                  95
Ser Glu Ala Arg Asp Ser Asp Ser Asp Asn Lys Glu Glu His Gly
                100                 105                 110
Gly Arg Val Ala Lys Lys Arg Gln Glu Val Val Glu Ser Gly Ser
            115                 120                 125
Glu Arg Ser Gly Glu Lys His Tyr Glu Ser Glu Asp Glu Val Asp
        130                 135                 140
Gln Thr Arg Ser Pro Arg Ser Pro Ser Glu Glu Lys Glu Val Gln
145                 150                 155                 160
Val Ala Gln Ser Asp Val Asn Ile Arg Asn Val Phe Gly Ser Ser Asp
                165                 170                 175
Asp Glu Asp Ala Glu Glu Tyr Val Arg Asn Asp Val Glu Gln Asp Glu
            180                 185                 190
His Arg Ser Pro Ile Glu Asp Glu Gly Ser Glu Lys Asp Leu Arg
        195                 200                 205
Pro Asp Asp Met Val Leu Asp Asp Ile Ile Pro Glu Glu Asp Pro Gln
        210                 215                 220
Tyr Glu Ser Glu Ala Glu His Val Glu Ala Arg Tyr Arg Glu Arg Pro
225                 230                 235                 240
Val Gly Pro Pro Leu Glu Val Glu Val Pro Phe Arg Pro Pro Gly
            245                 250                 255
Asp Pro Val Lys Met Asn Met Ile Lys Val Ser Asn Ile Met Gly Ile
            260                 265                 270
Asp Pro Lys Pro Phe Asp Ala Lys Thr Phe Val Glu Asp Thr Phe
        275                 280                 285
Met Thr Asp Glu Pro Gly Ala Lys Asn Arg Ile Arg Leu Asp Asn Asn
        290                 295                 300
Ile Val Arg His Arg Phe Val Lys Ser Arg Asp Gly Lys Thr Tyr Ser
305                 310                 315                 320
Glu Ser Asn Ala Arg Phe Val Arg Trp Ser Asp Gly Ser Leu Gln Leu
                325                 330                 335
Leu Ile Gly Asn Glu Val Leu Asn Ile Thr Glu Gln Asp Ala Lys Glu
            340                 345                 350
Asp Gln Asn His Leu Phe Ile Lys His Glu Lys Gly Ile Leu Gln Ser
        355                 360                 365
Gln Gly Arg Ile Leu Lys Lys Met Arg Phe Thr Pro Ser Ser Leu Thr
    370                 375                 380
Ser Asn Ser His Arg Leu Leu Thr Ala Ile Val Glu Ser Arg Gln Lys
385                 390                 395                 400
Lys Ala Phe Lys Val Lys Asn Cys Val Thr Asp Ile Asp Pro Glu Arg
                405                 410                 415
Glu Lys Glu Lys Arg Glu Lys Ala Glu Ser Gln Asn Leu Lys Ala Ser
            420                 425                 430
Thr Lys Leu Ser Gln Ala Arg Glu Lys Ile Lys Arg Lys Tyr Pro Leu
        435                 440                 445
Pro Val Glu Arg Arg Gln Leu Ser Thr Gly Tyr Leu Glu Asp Ala Leu
    450                 455                 460
```

```
Asp Glu Asp Asp Glu Asp Tyr Arg Ser Asn Arg Gly Tyr Glu Glu Asp
465                 470                 475                 480
Leu Glu Ala Glu Ala Gln Arg Glu Arg Arg Ile Leu Asn Ala Lys Lys
                485                 490                 495
Ser His Lys Gly Ile Pro Gly Arg Ser Ser Met Thr Ser Ala Arg Pro
            500                 505                 510
Ser Arg Arg Gln Met Glu Tyr Ser Glu Ser Arg Glu Glu Ser Glu
            515                 520                 525
Tyr Glu Thr Glu Glu Glu Glu Glu Lys Ser Pro Ala Arg Gly Arg
            530                 535                 540
Gly Lys Asp Ser Glu Asp Glu Tyr Glu Glu Asp Ala Glu Glu Asp Glu
545                 550                 555                 560
Glu Glu Arg Gly Lys Ser Asn Arg Tyr Ser Asp Glu Asp Glu Glu
                565                 570                 575
Glu Glu Val Ala Gly Gly Arg Ala Glu Lys Asp His Arg Gly Ser Gly
                580                 585                 590
Arg Lys Arg Lys Gly Ile Glu Ser Asp Glu Glu Glu Ser Pro Pro Arg
            595                 600                 605
Lys Ala Pro Thr His Arg Arg Lys Ala Val Ile Asp Asp Ser Asp Glu
    610                 615                 620
Asp
625

<210> SEQ ID NO 7
<211> LENGTH: 2736
<212> TYPE: DNA
<213> ORGANISM: Arabidopsis thaliana

<400> SEQUENCE: 7
cttaaaaaat aaaaagactt cagcatctgc ttcctctcga caatttcgac attactcttt        60 cgttttcac  cccttccttc ttctccttta gccgcccgtc gtcgatctct gcaacacttt       120
ccgacgattt ctccgtctga tctcaagtga gtctccttca acttttctct tcttttctat       180
acccttccct ctctctattt ccttttctcc gccacaaacg gcttctgcgt tccctgtttc       240
cgccgtcctt acctcttcca atcaaattga agatccatac cagaaatcga tccttctccg       300
tctccgaatt cgcttgatta acctcagaaa ctcgtattgg ttttcgcaaa accgcgattt       360
ggctttagac ttcaccgtta cctgattggg tgaaaagttt ccttaaccc  tattaatggc       420 ttatctaggg ttagaatcca aaggattgtt ttgctcttgt agttagctat ctactggttt       480
tttgtggtat acaccgtact tgaccaatgt ggtgaggtct tttgcttctc taactgtata       540
cttctcataa tttcaggtga cagtgaaaac catttaaatt cgttacttgt gagcctcctt       600
agaagattat gggtgattta gagaacttgc ttttggaagc tgctgggaga acaaattcag       660
cagggaggag tcgtcatcct ccatcatcga ggagacgtga gggttcttac tctgatggta       720
gtagcgattc aagggatgat tctgatgaag atcgtggcta tgctagtaga aaaccctctg       780
ggtctcaagt tcctttgaag aagagattgg aggcagagag agaagatcga gctgctcgag       840
ttgaaggtgg ttatggtgat ggaccatctg atcgtgaagg tgacagcagc gaggagtctg       900 atttggaga tgaccttta  aagatgagg  aagacaggca gaagcttgct ggaatgactg       960
agtttcagag agatgatt  ctctctgaac gtgctgataa gaaaggtgat aagaacttca      1020
ctgagaaact taggtccaag agagaaagtg agaaaccccc tgtttctaaa aaggagactc      1080
agcctcttcc ggcctctcgt ggtgtgcgtt catctgctag atctgcagac agagccgctg      1140
```

-continued

| | |
|---|---|
| ctaaggatga tgccctgaat gaattgaggg cgaagcgtat gaagcagcag gacccagcag | 1200 |
| ctctcaggaa actgagagat gcatcaaaag gtggttcagg tagtcgagat ttctcatcaa | 1260 |
| cgaagaggaa accgttagct tcctccaatt tgagtagttc cagccaaagt gacagtgata | 1320 |
| gtaggtctca gagtgatgat gaaggctcga atggaggaat gctagacagt gatgatgaca | 1380 |
| ggtcagatgt gcctacgttt gaggatgtta aggaagttac cattagacgg tctaagcttg | 1440 |
| ccaaatggct aatggagcct ttctttgaag agcttatagt tgggtgcttt gtgagggttg | 1500 |
| ggatcggaag gtcaaagagt ggtccaattt acagactctg ctgggtgaag aatgttgatg | 1560 |
| caaccgatcc tgacaagacc tacaagctag agaataaaac tacacacaag taccttaacg | 1620 |
| tcgtctgggg aaatgaaacc tcggcggctc gatggcaaat ggctatgatc tcagatggtc | 1680 |
| atccgctgga ggaagagtat aggcaatgga tcagagaggt tgagcgaaca aatggtcgca | 1740 |
| tgcccacaaa gcaagatata tcggagaaga agaagcgat acaaagaaca aacagttttg | 1800 |
| tttactctgc ggaaactgtt aaacagatgc tgcaggagaa aaaatctgcg tcagtcaggc | 1860 |
| caatgaatgt tgcggccgag aaagatcggc ttagaaaaga attggaaatt gcgcagagca | 1920 |
| aaaacgatga agcaggtgta gagaggatca agtcgaaaat caaacagctc gacgcttcac | 1980 |
| ggaacaagaa aggggtagat aaaaaagcgc ttaaacttgc tgagatgaac aagaagaaca | 2040 |
| gagccgagaa tttcaagaac gcatctgagg taaaatcaat aactgctagt ctcaaagccg | 2100 |
| gtgaagcagg gtatgatccg ttttcaagaa gatggacccg atcatcaaac tactacaacg | 2160 |
| ggaaaaacaa ggggaaagat ggagaagaga acgaggcagc ggttgcagca gcggttgaga | 2220 |
| ccaatggagc agatgcagga gcaggtgttg aagcgacaga agcagcttta gaagcagctg | 2280 |
| cagaggcagg aaagctaata gacacaagag ctccaatagg tcaaggagca gaacacaatc | 2340 |
| agcttcataa ctttgaattg tcgttatcgc taacggcttt acagaagtac ggaggacctc | 2400 |
| aaggagtaca gaaagcgttc atggcgagga agcaactgac cgaagcaact gtgggatgca | 2460 |
| gagtcgcaga gaacgatggc aagagacatg gccttacgtt aactgttagt gattacaaga | 2520 |
| gaaggagagg tcttctctga tttatttgca ttttttttcaa gtctcagtgt tcattatct | 2580 |
| tctgaaaact gcttcttggt tcttcttttc ttcatatctt tcttttgtac tccacaaaat | 2640 |
| atgtttagat cagtttgttt tttcttgaaa tattttgta ctcgtttttg tgtgaactct | 2700 |
| cctgattagt gtatgactgc atgaaattag aaaatc | 2736 |

<210> SEQ ID NO 8
<211> LENGTH: 6788
<212> TYPE: DNA
<213> ORGANISM: Arabidopsis thaliana

<400> SEQUENCE: 8

| | |
|---|---|
| gattcacttc atcgttggca cacacacata ctctctattc gaaaaattcg ccactgcaat | 60 |
| ttcttctagg gtttctggta atcctcactt agccgggcaa tggcgagtgt gtacataccg | 120 |
| gttcagaatt cagaagaaga agttaggggt gttcttgatc agctccctcg tgacgcttct | 180 |
| gatatacttg atattcttaa agccgaacaa gctcctctcg atctctggct catcatcgcg | 240 |
| gttcgttctt ttccactcta attaggttct atctggaatc gagttttgtt gagtttttct | 300 |
| tagttaatgg ctgatgggtt ttgattaaca cttcaaaagt tagttgcttt tgtggctgat | 360 |
| ttgcttaaag attgtttttt tttccaattc tgatttggt ttcatctatg gtgaagaggg | 420 |
| agtacttcaa acaaggaaaa attgaacagt ttcgacaaat attggaggaa gggtcaagtt | 480 |

```
ctggtaagca gttatacgat gatgctgctt caatttgttc tagaattggt tatttcgaaa    540
atataagtcc ttttttgttc ttttttggcaa gacattgacg agtactatgc cgatgttaag    600
tacgagagaa tagcgatttt gaatgctcta ggtgcgtatt atagctacct tggtaaaact    660
gagaccaaaa acagagagaa agaggagcaa tttatctctg ccacacgata ttataacaaa    720
gcatcgagaa tcgatatgca tgaaccttcc acttggggttg ggaaaggtac taccagattc    780
gtttcgactg ataagtttct gttgcaagca attcctataa caatctttct tttccggttc    840
tccctgtaca atgtacgctt taagaatttg aaggttgtga tgatgctcta tgtttactaa    900
gatacagaat cctgaaatgt aattgtctgc ttacaggtca gctcttactg gctaagggtg    960
aaatagataa tgctcttcag gcatttaaga ttgtgttaga cactgcccct gataatgttc    1020
ctgctcttct gggtcaggta taatgacttg tgatttcatt ttctgtcact tagctaataa    1080
tttgtaggta ggtagattct gtatactaga atttattggt ggtagtaaga atttgattct    1140
gacgctctct ttcttaccaa cctaggcctg acacagtatt agtctattgt ttactttttct    1200 gcaaattaat aacttgctct atcacgtata caggcttctg tagaatttaa tcgtggacga    1260
ttttctgagt cattacaact atacaaggta agcttttcct tataacctac tatatttctg    1320
tataccactt cttcattttg gctgtaaatc tcatggcttt gattgttcaa gtgaaccatc    1380
tagtctattt atggaacaaa ttggtagtat tttgatttgt ctatgttttg aattctttta    1440
gagggccttg caagtatttc ccggttgtcc tgcagctgtg agactgggaa ttggttttgt    1500
cgttataagt tgggggcaact agataaagca cggcaagcgt ttgatcgcgt tttgcaggca    1560
agtgggactg ggatgtttat ctcatcttct tatgacatag ctgactgtat gcgtcaacaa    1620
atagtgctaa ttaccataat tctatttctg cagctagatc ctgataatgt tgaggctctt    1680
gtggcacttg ggattatgga tttgcaagca aatgattgta agtataccto agttctaaat    1740 cttatgataa tgcgtgtggg ctggaaagat tctattaact ttacttctct ttggccttca    1800
ctgatgatat tacatatgta tagctatagg aatgaggaaa ggaatggaca gaatgcagca    1860
ggcattcgag atttatccct attgcgcatc agccttaaat tatttggcca atcactttt    1920 tttcaccggc cagcactttc ttgttgagca gctgactgaa acagcattag ccgtcacaac    1980
tcatgggcca acaaagtcac attctttta caatttagca cggtcatatc atagcaaggt    2040
ttgacatttt tgtcctccct tgtatattcc attcttatct accctctgag cttgccagtg    2100
gaggaaaaaa tacgagtaat aaataattta tttgggttgt gatatatttg aggcgttttt    2160
ttcattctat gggctgttat agaagaatgc atcttttttt gtttcctttg tgtaaccttc    2220
ctttctgatg tctgatgatg gtcttgtttt aggggggactt tgaaaaggct gggatgtact    2280
atatggcagc catcaaagaa actaataata acccacacga atttgtattt ccttactttg    2340 gtaactttc tccactcttc tgctgaattc cccttaattc ttcggatgtt accaatctga    2400
gtcattactc attagcaatg aagatactgc acctttgtca tttattttccc ttttagcagt    2460 agaatatatg aaatgagacc atcaataatt agttccagtc tgtaaaacgt atgattatga    2520
acaaatttgt gtataatatc tcgtgcttca atttctagta ttgctcagtt tggattgatg    2580
atcttatatg ttcatttagt ttgatttttt ttttgtgtt gcaggtttgg gtcaagtaca    2640
actaaagttg ggggagctta aggatctgt atttaatttt gagaaagtat tagaagttta    2700
tcctgacaac tgcgagactt tgaaggttaa atgactgcaa cctttttctt tattgatcgt    2760
tcattctgta tttcatcctt taaatataaa atgcttatg tgcacgtttc tttcttcct    2820 taggctctcg ggcacttata cacccagctt ggacaaaatg agaaggccct tgagtacatg    2880
```

```
cgaaaggcca caaaacttga tccacgtgat gcccaggtta gtttggttta acataattct   2940
taagcctgat ctttcaaaag gtgttgatac ttgcatgaat tctttggttg tagttgttat   3000
atagtttacc ttactgtgga tcactttcga gtgacacttc cacttttgtt acctaaattg   3060
taacaccagc acacttagtc caagtaagga agaaaaaaca tagtagcaag acatagttct   3120
gccatatatc ttgagaatac cttttgggtt tgtttccccc acagctcata tgtgtggttg   3180
aagatctaat agggatgata atcatctatt gactattgcg ataattttt ccttgattta    3240
tagttttggg ttttgtaggc atttgttggc cttggtgagc tgctgatatc atctgacacg   3300
ggagccgccc ttgacgcctt caaaatggta aagtgtgatc ttgataattg tatctcctct   3360
tcaagtacat gatggcatgt tgtacataaa gaaagacatt aattttctg agaaccatta    3420
atgaaaactc ccaggcacgg acgctcatga aaaaggagg gcaagaagtg cctatagaag    3480
tcctgaatga catcggtgct ttacattttg agagagaaga atttgaggtt tgtagtgagg   3540
ttgtttctgc ttcttagctt tgatattttg ctattggctt caatactctt tttccttgca   3600
gtctgcgctt gagaatttta aggaggctct gggtgatgga atatggatta gcttccttga   3660
tgaaaagaa aatttggaac agacaggtgt atctgttctc gggtacaagg acacgggcat    3720
tttccatagg ctgattgaaa gtggtcactc tgtcgatgta ccttggaata aagttacaac   3780
tttgtttaac ctggctagat tacttgaaca gatacacaaa acagaagcag cgactttat    3840
gtatcggttg atacttttca aggtctatat ttcctactta tttaatttga tattatttgc   3900
tgtttcactt tgtgatgagt tttctagtgg tagacttgag gagaaaagaa ggaaaaaaac   3960
ttgaggagcc gttttctgat tattcctgtc tgatagatga ttttgagtgg ttacttggtt   4020
tttacaaata tattttgtct aaaacccctt ctttcgcggt ttttaaata tctattcatg    4080
tactaaaagt ataaaaatgg gaacattgat tcggcataat gacttccttg gttataattg   4140
agtggcttct gctctcttgg gaagttcagc atcgtttcgt atatgtgcta tatagttttc   4200
tgctttatat ttcttctgtt tcttatagtt tttggataca cctaccatgt cttacattat   4260
ttgtttgaat gttcaccctg atataagctt gatcctttta tttctctttc aataatctga   4320
tgacgacttt tgatttctgt caacttaatc tgactgccta tccggtgcag tatcctggct   4380
acatagatgc ttatttgagg cttgctgcaa gtgcaaaagc tcagaacaat cttcctctgg   4440
ccattgaact ggtcggtcta ccaccgtttt caacattaat tttatttaat ctgtagcagc   4500
ttgttttctc tctctgaccg tcttttccta cttcccctat aggtgaatga agctctgaaa   4560
gtggacgata aaaatccaaa tgctttgtct ctacttggtg aattggagct taagaacgat   4620
gactgggtta aggcaaagga aacctttcga gctgctaatg atgcaactga tgggaaggac   4680
tcatatgcta ttctttctct ggtatatatt tttatttccg atttttttgc gtttcagaat   4740
aataagaatc atcatattaa gttccttttg ggttgttcaa agctcatcgc attatcatat   4800
caatgaatcg attttatgtg agcaccccac acccaaatat ttgtaccctg cctttttctat  4860
gggtccaatc taatcagcta ttactgcgat ctgggctctc ttgtaaaaca cttcagtcaa   4920
gataacgata gggttctttt caatacgtgt atggaagacc agccctcatt ctgtatggtt   4980
cctctaccag cagcctggtg agggctggtt gtctagcaga tatctaacta ccttggagtg   5040
aattctgtct tgattataaa tgattggaac aattattgta caagctattt tgtgtgtgt    5100
aatatttctt cctggaatgt tttagggaa ctggaactat tttgcagcaa tgcgcaatga    5160
gaaaagaaat ccaaaattag aagctacaca tctggagaag gccaaggaac tctatactaa   5220
```

```
agtatggtgt ttagtttttc tcctttctct cttctaatta ttagtaattt gggaatatgt    5280
atgtgcttct gggggggtgtt ttgggtggag gtttgcctgt agaaacctga acacgttgtt    5340 gaaattttg ctataccagt agcattgcat gcttaaattg gcgatgtcct ctttccatca    5400
acgctaatcg tctttctcat tgttgatcgt tgggattaac aggtcctgac tcaacataat    5460
tccaacatgt atgctgccaa cggttctggc attgtattag cagagaaagg ccaatttgat    5520
attgccaagg atgtttttac tcaggtcagc ttttatcatt tactgttcat agtataggct    5580
agctaaattc ttgaaatcat tggaattttg tgaatgtttt aggttcaaga agctgcgagc    5640
ggaagtgtat ttcttcagat gcctgatgta tgggtgaatc tggctcatgt ttactttgct    5700
caagggaatt ttgccttaac cgtgaaaatg gtttgtcatt ttatatagcg tttttttttt    5760
ttttaaattc ttttggttga tttcgatgtt ttgcttaagt actctgttca ttatctatgt    5820
tgttggcagt atcaaaactg cttgcgaaag ttcttttaca acacagactc ccaaatcctt    5880
ctttacttag cccgtaccca ttatgaggct gagcagtggc aagagtgcaa aaagacacta    5940
ttaagggcca ttcacttgac tccttcaaat tacacattca gatttgattt gggtgctgta    6000
atgcaaaaat catcgtcttc cacactgcaa agaaaaaaaa gaacagctga tgaggttaac    6060
taaagatttt cccttgcttc tttctgactc tagtcttgtg tcgtagaaga tagacagata    6120
ttaacatgca tcgattggga atttatcaga ctatgaactt gcttctacag cttgtgtatc    6180
tagaactttt caccatgacc ctagcatagt atgttagtca tccttgctaa gtaatggcta    6240
atctagaatg caatactagg attgtgttc ttgttttatt agaagatgtc tagacaatac    6300
taattcgtcc aatggggatt aattgatttc cacctgacaa ttacttgatg actctgcagg    6360
tgcgctcaac agttgcagaa gcagagaatg ctgttcgtgt attcactcaa ttgtctgctg    6420
cttcagacct ccatgttcat gggtttgata gcaagaaaat acaaacccat gttcagtatt    6480
gctcgcactt gctggaagca gcaaaagttc accgtgaagc tgctgagcag gaggagctgc    6540
agaaccgaca gagattagaa gttgctcgtc aggctgcttt ggcagaagaa gcacgccgta    6600
aagctgaaga acagaggaaa tatcaggtaa ctattgactt gcaagttaac catttgcagc    6660
aacaaattta ttttggtgat atatatggaa gcttttcaag tcagtgatat gcattttct    6720 cttgggcagt tggagaaaag aaaacaggag gaagagctga gacgcctaaa gcaagaagaa    6780
gaaaaatt                                                              6788
```

<210> SEQ ID NO 9
<211> LENGTH: 1931
<212> TYPE: DNA
<213> ORGANISM: Arabidopsis thaliana

<400> SEQUENCE: 9

```
atgggtgatt tagagaactt gcttttggaa gctgctggga gaacaaattc agcagggagg      60
agtcgtcatc ctccatcatc gaggagacgt gagggttctt actctgatgg tagtagcgat     120
tcaagggatg attctgatga agatcgtggc tatgctagta gaaaaccctc tgggtctcaa     180
gttcctttga agaagagatt ggaggcagag agagaagatc gagctgctcg agttgaaggt     240
ggttatggtg atggaccatc tgatcgtgaa ggtgacagca gcgaggagtc tgattttgga     300
gatgaccttt acaagaatga ggaagacagg cagaagcttg ctggaatgac tgagtttcag     360
agagagatga ttctctctga acgtgctgat aagaaaggtg ataagaactt cactgagaaa     420
cttaggtcca agagagaaag tgagaaaacc cctgtttcta aaaaggagac tcagcctctt     480
ccggcctctc gtggtgtgcg ttcatctgct agatctgcag acagagccgc tgctaaggat     540
```

```
gatgccctga atgaattgag ggcgaagcgt atgaagcagc aggacccagc agctctcagg      600
aaactgagag atgcatcaaa aggtggttca ggtagtcgag atttctcatc aacgaagagg      660
aaaccgttag cttcctccaa tttgagtagt tccagccaaa gtgacagtga tagtaggtct      720
cagagtgatg atgaaggctc gaatggagga atgctagaca gtgatgatga caggtcagat      780
gtgcctacgt ttgaggatgt taaggaagtt accattagac ggtctaagct tgccaaatgg      840
ctaatggagc ctttctttga gagcttata gttgggtgct tgtgagggt tgggatcgga       900 aggtcaaaga gtggtccaat ttacagactc tgctgggtga agaatgttga tgcaaccgat      960
cctgacaaga cctacaagct agagaataaa actacacaca agtaccttaa cgtcgtctgg     1020
ggaaatgaaa cctcggcggc tcgatggcaa atggctatga tctcagatgg tcatccgctg     1080
gaggaagagt ataggcaatg gatcagagag gttgagcgaa caaatggtcg catgcccaca     1140
aagcaagata tatcggagaa gaagaagcg atacaaagaa caaacagttt tgtttactct      1200
gcggaaactg ttaaacagat gctgcaggag aaaaaatctg cgtcagtcag ccaatgaat      1260 gttgcggccg agaaagatcg gcttagaaaa gaattggaaa ttgcgcagag caaaaacgat     1320
gaagcaggtg tagagaggat caagtcgaaa atcaaacagc tcgacgcttc acggaacaag     1380
aaaggggtag ataaaaaagc gcttaaactt gctgagatga acaagaagaa cagagccgag     1440
aatttcaaga acgcatctga ggtaaaatca ataactgcta gtctcaaagc cggtgaagca     1500
gggtatgatc cgttttcaag aagatggacc cgatcatcaa actactacaa cgggaaaaac     1560
aaggggaaaa atggagaaga gaacgaggca gcggttgcag cagcggttga gaccaatgga     1620
gcagatgcag gagcaggtgt tgaagcgaca gaagcagctt tagaagcagc tgcagaggca     1680
ggaaagctaa tagacacaag agctccaata ggtcaaggag cagaacacaa tcagcttcat     1740
aactttgaat tgtcgttatc gctaacggct ttacagaagt acggaggacc tcaaggagta     1800
cagaaagcgt tcatggcgag gaagcaactg accgaagcaa ctgtgggatg cagagtcgca     1860
gagaacgatg caagagaca tggccttacg ttaactgtta gtgattacaa gagaaggaga     1920
ggtctctctg a                                                        1931
```

<210> SEQ ID NO 10
<211> LENGTH: 3679
<212> TYPE: DNA
<213> ORGANISM: Arabidopsis thaliana

<400> SEQUENCE: 10

```
cgattcactt catcgttggc acacacacat actctctatt cgaaaaattc gccactgcaa       60
tttcttctag ggtttctggt aatcctcact tagcccggca atggcgagtg tgtacatacc      120
ggttcagaat tcagaagaag aagttagggt tgttcttgat cagctccctc gtgacgcttc      180
tgatatactt gatattctta aagccgaaca agctcctctc gatctctggc tcatcatcgc      240
gagggagtac ttcaaacaag gaaaaattga acagtttcga caaatattgg aggaagggtc      300
aagttctgac attgacgagt actatgccga tgttaagtac gagagaatag cgattttgaa      360
tgctctaggt gcgtattata gctaccttgg taaaactgag accaaaaaca gagagaaaga      420
ggagcaattt atctctgcca cacgatatta taacaaagca tcgagaatcg atatgcatga      480
accttccact tgggttggga aaggtcagct cttactggct aagggtgaaa tagataatgc      540
tcttcaggca tttaagattg tgttagacac tgccccctgat aatgttcctg ctcttctggg      600
tcaggcttct gtagaattta atcgtggacg attttctgag tcattacaac tatacaagag      660
```

-continued

```
ggccttgcaa gtatttcccg gttgtcctgc agctgtgaga ctgggaattg gttttgtcgt      720
tataagttgg ggcaactaga taaagcacgg caagcgtttg atcgcgtttt gcaggcaaat      780
cctgataatg ttgaggctct tgtggcactt gggattatgg atttgcaagc aaatgattct      840
ataggaatga ggaaaggaat ggacagaatg cagcaggcat tcgagattta tccctattgc      900
gcatcagcct taaattattt ggccaatcac ttttttttca ccggccagca ctttcttgtt      960
gagcagctga ctgaaacagc attagccgtc acaactcatg gccaacaaa gtcacattct     1020 ttttacaatt tagcacggtc atatcatagc aagggggact ttgaaaaggc tgggatgtac     1080
tatatggcag ccatcaaaga aactaataat aacccacacg aatttgtatt tccttacttt     1140
ggtttgggtc aagtacaact aaagttgggg gagcttaaag gatctgtatt taattttgag     1200
aaagtattag aagtttatcc tgacaactgc gagactttga aggctctcgg cacttatac     1260 acccagcttg acaaaatga aaggcccctt gagtacatgc gaaaggccac aaaacttgat     1320
ccacgtgatg cccaggcatt tgttggcctt ggtgagctgc tgatatcatc tgacacggga     1380
gccgcccttg acgccttcaa aatggcacgg acgctcatga aaaaggagg caagaagtg      1440 cctatagaag tcctgaatga catccggtgct ttacattttg agagagaaga atttgagtct    1500
gcgcttgaga attttaagga ggctctgggt gatggaatat ggattagctt ccttgatgaa     1560
aaagaaaatt tggaacagac aggtgtatct gttctcgggt acaaggacac gggcattttc     1620
cataggctga ttgaaagtgg tcactctgtc gatgtacctt ggaataaagt tacaactttg     1680
tttaacctgg ctagattact tgaacagata cacaaaacag aagcagcgac ttttatgtat     1740
cggttgatac ttttcaagta tcctggctac atagatgctt atttgaggct tgctgcaagt     1800
gcaaaagctc agaacaatct tcctctggcc attgaactgg tgaatgaagc tctgaaagtg     1860
gacgataaaa atccaaatgc tttgtctcta cttggtgaat tggagcttaa gaacgatgac     1920
tgggttaagg caaaggaaac ctttcgagct gctaatgatg caactgatgg gaaggactca     1980
tatgctattc tttctctggg gaactggaac tattttgcag caatgcgcaa tgagaaaaga     2040
aatccaaaat tagaagctac acatctggag aaggccaagg aactctatac taaagtcctg     2100
actcaacata attccaacat gtatgctgcc aacggttctg gcattgtatt agcagagaaa     2160
ggccaatttg atattgccaa ggatgttttt actcaggttc aagaagctgc gagcggaagt     2220
gtatttcttc agatgcctga tgtatgggtg aatctggctc atgtttactt tgctcaaggg     2280 aatttttgcct taaccgtgaa aatggttgt catttatat agcgttttt tttttttaa      2340 attcttttgg ttgatttcga tgttttgctt aagtactctg ttcattatct atgttgttgg     2400
cagtatcaaa actgcttgcg aaagttcttt tacaacacag actcccaaat ccttctttac     2460
ttagcccgta cccattatga ggctgagcag tggcaagagt gcaaaaagac actattaagg     2520
gccattcact tgactccttc aaattacaca ttcagatttg atttgggtgc tgtaatgcaa     2580
aaatcatcgt cttccacact gcaaaagaaa aaagaacag ctgatgaggt gcgctcaaca     2640
gttgcagaag cagagaatgc tgttcgtgta ttcactcaat tgtctgctgc ttcagacctc     2700
catgttcatg ggtttgatag caagaaaata caaacccatg ttcagtattg ctcgcacttg     2760
ctggaagcag caaaagttca ccgtgaagct gctgagcagg aggagctgca gaaccgacag     2820
agattagaag ttgctcgtca ggctgctttg gcagaagaag cacgccgtaa agctgaagaa     2880
cagaggaaat atcagttgga gaaagaaaa caggaggaag agctgagacg cctaaagcaa     2940
gaagaagaaa aatttcagcg tataaaggaa caatggaaga gctccacacc tggatctaat     3000
aagcggaagg atagagtgga agatgatgat ggggaaagta agcccagtga gcggagaaga     3060
```

```
aagaagggtg gaaagagaag aaagaaggac aaaagctcaa gggctcgaca ctacgaggac    3120
gatgaagaag aagctgccac tatggatgat cataatgaag tggaagatga agacgccaac    3180
actaattata acagggaaga tgagatgact actcaagaag ctgaggaacc tgtggatgat    3240
gatgctcatg atcttctcgc tgctgctggg ctcgaagatc ctgatgttga tgatgatgag    3300
gtacctactt cgggtgtaag gcgaagaagg gcgttatcgt catcagacga agaaggtgaa    3360
ttaatggagg agagtcatcc aaattcaagc ccccagaaag aaaaagaaga gagcaatggg    3420
gaagctggtc atcctaacat ggaggaagaa gaggaagagg aagaggccaa ttgagagata    3480
tttcatacat aacaacagat atctcttgtg tgtttgtaac tttagtgaca aagatttcat    3540
tgattcaatt tctctagtag tcagagtgtg aagacaattt acattcacag gccaaggatg    3600
atcagtttgt attttgggtt atttggattg agccttgttt ttatttgcta ttgttactaa    3660
tagaaaagct tttttctttt                                                3679

<210> SEQ ID NO 11
<211> LENGTH: 3582
<212> TYPE: DNA
<213> ORGANISM: Arabidopsis thaliana

<400> SEQUENCE: 11
cgattcactt catcgttggc acacacacat actctctatt cgaaaaattc gccactgcaa      60
tttcttctag ggtttctggt aatcctcact tagccgggca atggcgagtg tgtacatacc     120
ggttcagaat tcagaagaag aagttagggt tgttcttgat cagctccctc gtgacgcttc     180
tgatatactt gatattctta aagccgaaca agctcctctc gatctctggc tcatcatcgc     240
gagggagtac ttcaaacaag gaaaaattga acagtttcga caaatattgg aggaagggtc     300
aagttctgac attgacgagt actatgccga tgttaagtac gagagaatag cgattttgaa     360
tgctctaggt gcgtattata gctaccttgg taaaactgag accaaaaaca gagagaaaga     420
ggagcaattt atctctgcca cacgatatta taacaaagca tcgagaatcg atatgcatga     480
accttccact tgggttggga aaggtcagct cttactggct aagggtgaaa tagataatgc     540
tcttcaggca tttaagattg tgttagacac tgcccctgat aatgttcctg ctcttctggg     600
tcaggcttct gtagaattta atcgtggacg atttttctgag tcattacaac tatacaagag     660
ggccttgcaa gtatttcccg gttgtcctgc agctgtgaga ctgggaattg gttctttgtc     720
gttataagtt ggggcaacta gataaagcac ggcaagcgtt tgatcgcgtt ttgcaggcaa     780
atcctgataa tgttgaggct cttgtggcac ttgggattat ggatttgcaa gcaaatgatt     840
ctataggaat gaggaaagga atggacagaa tgcagcaggc attcgagatt tatccctatt     900
gcgcatcagc cttaaattat ttggccaatc acttttttt caccggccag cactttcttg     960
ttgagcagct gactgaaaca gcattagccg tcacaactca tgggccaaca aagtcacatt    1020 cttttttacaa tttagcacgg tcatatcata gcaagggga ctttgaaaag ctgggatgt    1080 actatatggc agccatcaaa gaaactaata ataacccaca cgaatttgta tttccttact    1140
ttggtttggg tcaagtacaa ctaaagttgg gggagcttaa aggatctgta tttaattttg    1200
agaaagtatt agaagtttat cctgacaact gcgagacttt gaaggctctc ggcacttat    1260 acacccagct tggacaaaat gagaaggccc ttgagtacat gcgaaaggcc acaaaacttg    1320
atccacgtga tgcccaggca tttgttggcc ttggtgagct gctgatatca tctgacacgg    1380
gagccgccct tgacgccttc aaaatggcac ggacgctcat gaaaaaagga gggcaagaag    1440
```

```
tgcctataga agtcctgaat gacatcggtg ctttacattt tgagagagaa gaatttgagt    1500
ctgcgcttga gaattttaag gaggctctgg gtgatggaat atggattagc ttccttgatg    1560
aaaaagaaaa tttggaacag acaggtgtat ctgttctcgg gtacaaggac acgggcattt    1620
tccataggct gattgaaagt ggtcactctg tcgatgtacc ttggaataaa gttacaactt    1680
tgtttaacct ggctagatta cttgaacaga tacacaaaac agaagcagcg acttttatgt    1740
atcggttgat acttttcaag tatcctggct acatagatgc ttatttgagg cttgctgcaa    1800
gtgcaaaagc tcagaacaat cttcctctgg ccattgaact ggtgaatgaa gctctgaaag    1860
tggacgataa aaatccaaat gctttgtctc tacttggtga attggagctt aagaacgatg    1920
actgggttaa ggcaaaggaa acctttcgag ctgctaatga tgcaactgat gggaaggact    1980
catatgctat tctttctctg ggaactggaa actattttgc agcaatgcgc aatgagaaaa    2040
gaaatccaaa attagaagct acacatctgg agaaggccaa ggaactctat actaaagtcc    2100
tgactcaaca taattccaac atgtatgctg ccaacggttc tggcattgta ttagcagaga    2160
aaggccaatt tgatattgcc aaggatgttt ttactcaggt tcaagaagct gcgagcggaa    2220
gtgtatttct tcagatgcct gatgtatggg tgaatctggc tcatgtttac tttgctcaag    2280
ggaattttgc cttaaccgtg aaaatgtatc aaaactgctt gcgaaagttc ttttacaaca    2340
cagactccca aatccttctt tacttagccc gtacccatta tgaggctgag cagtggcaag    2400
agtgcaaaaa gacactatta agggccattc acttgactcc ttcaaattac acattcagat    2460
ttgatttggg tgctgtaatg caaaaatcat cgtcttccac actgcaaaag aaaaaaagaa    2520
cagctgatga ggtgcgctca acagttgcag aagcagagaa tgctgttcgt gtattcactc    2580
aattgtctgc tgcttcagac ctccatgttc atgggtttga tagcaagaaa atacaaaccc    2640
atgttcagta ttgctcgcac ttgctggaag cagcaaaagt tcaccgtgaa gctgctgagc    2700
aggaggagct gcagaaccga cagagattag aagttgctcg tcaggctgct ttggcagaag    2760
aagcacgccg taaagctgaa gaacagagga aatatcagtt ggagaaaaga aaacaggagg    2820
aagagctgag acgcctaaag caagaagaag aaaaatttca gcgtataaag gaacaatgga    2880
agagctccac acctggatct aataagcgga aggatagagt ggaagatgat gatggggaaa    2940
gtaagcccag tgagcggaga agaaagaagg gtggaaagag aagaaagaag gacaaaagct    3000
caagggctcg acactacgag gacgatgaag aagaagctgc cactatggat gatcataatg    3060
aagtggaaga tgaagacgcc aacactaatt ataacaggga agatgagatg actactcaag    3120
aagctgagga acctgtggat gatgatgctc atgatcttct cgctgctgct gggctcgaag    3180
atcctgatgt tgatgatgat gaggtaccta cttcgggtgt aaggcgaaga agggcgttat    3240
cgtcatcaga cgaagaaggt gaattaatgg aggagagtca tccaaattca gcccccagaa    3300
aagaaaaaga agagagcaat ggggaagctg gtgatcctaa catggaggaa gaagaggaag    3360
aggaagaggc caattgagag atatttcata cataacaaca gatatctctt gtgtgtttgt    3420
aactttagtg acaaagattt cattgattca atttctctag tagtcagagt gtgaagacaa    3480
tttacattca caggccaagg atgatcagtt tgtatttggg gttatttgga ttgagccttg    3540
tttttatttg ctattgttac taatagaaaa gctttttttct tt                      3582
```

<210> SEQ ID NO 12
<211> LENGTH: 1506
<212> TYPE: DNA
<213> ORGANISM: Arabidopsis thaliana

<400> SEQUENCE: 12

```
atggatttgc aagcaaatga ttctatagga atgaggaaag gaatggacag aatgcagcag    60
gcattcgaga tttatcccta ttgcgcatca gccttaaatt atttggccaa tcactttttt   120
ttcaccggcc agcactttct tgttgagcag ctgactgaaa cagcattagc cgtcacaact   180
catgggccaa caaagtcaca ttcttttttac aatttagcac ggtcatatca tagcaagggg   240
gactttgaaa aggctgggat gtactatatg cagccatca aagaaactaa taataaccca    300
cacgaatttg tatttcctta ctttggtttg ggtcaagtac aactaaagtt ggggggagctt   360
aaaggatctg tatttaattt tgagaaagta ttagaagttt atcctgacaa ctgcgagact   420
ttgaaggctc tcgggcactt atacacccag cttggacaaa atgagaaggc ccttgagtac   480
atgcgaaagg ccacaaaact tgatccacgt gatgcccagg catttgttgg ccttggtgag   540
ctgctgatat catctgacac gggagccgcc cttgacgcct caaaatggc acggacgctc    600
atgaaaaaag gagggcaaga agtgcctata gaagtcctga tgacatcgg tgctttacat    660
tttgagagag aagaatttga gtctgcgctt gagaattta aggaggctct gggtgatgga    720
atatggatta gcttccttga tgaaaaagaa aatttggaac agacaggtgt atctgttctc   780
gggtacaagg acacgggcat tttccatagg ctgattgaaa gtggtcactc tgtcgatgta   840
ccttggaata aagttacaac tttgtttaac ctggctagat tacttgaaca gatacacaaa   900
acagaagcag cgacttttat gtatcggttg atactttca agtatcctgg ctacatagat   960
gcttatttga ggcttgctgc aagtgcaaaa gctcagaaca atcttcctct ggccattgaa  1020
ctggtgaatg aagctctgaa agtggacgat aaaaatccaa atgctttgtc tctacttggt  1080
gaattggagc ttaagaacga tgactgggtt aaggcaaagg aaacctttcg agctgctaat  1140
gatgcaactg atgggaagga ctcatatgct attctttctc tggggaactg gaactatttt  1200
gcagcaatgc gcaatgagaa aagaaatcca aaattagaag ctacacatct ggagaaggcc  1260
aaggaactct atactaaagt cctgactcaa cataattcca acatgtatgc tgccaacggt  1320
tctggcattg tattagcaga gaaaggccaa tttgatattg ccaaggatgt ttttactcag  1380
gttcaagaag ctgcgagcgg aagtgtattt cttcagatgc ctgatgtatg ggtgaatctg  1440
gctcatgttt actttgctca agggaatttt gccttaaccg tgaaaatggt ttgtcatttt  1500
atatag                                                              1506
```

<210> SEQ ID NO 13
<211> LENGTH: 643
<212> TYPE: PRT
<213> ORGANISM: Arabidopsis thaliana

<400> SEQUENCE: 13

```
Met Gly Asp Leu Glu Asn Leu Leu Leu Glu Ala Ala Gly Arg Thr Asn
1               5                   10                  15

Ser Ala Gly Arg Ser Arg His Pro Pro Ser Ser Arg Arg Arg Glu Gly
            20                  25                  30

Ser Tyr Ser Asp Gly Ser Ser Asp Ser Arg Asp Asp Ser Asp Glu Asp
        35                  40                  45

Arg Gly Tyr Ala Ser Arg Lys Pro Ser Gly Ser Gln Val Pro Leu Lys
    50                  55                  60

Lys Arg Leu Glu Ala Glu Arg Glu Asp Arg Ala Ala Arg Val Glu Gly
65                  70                  75                  80

Gly Tyr Gly Asp Gly Pro Ser Asp Arg Glu Gly Asp Ser Ser Glu Glu
                85                  90                  95
```

-continued

```
Ser Asp Phe Gly Asp Asp Leu Tyr Lys Asn Glu Glu Asp Arg Gln Lys
             100                 105                 110

Leu Ala Gly Met Thr Glu Phe Gln Arg Glu Met Ile Leu Ser Glu Arg
             115                 120                 125

Ala Asp Lys Lys Gly Asp Lys Asn Phe Thr Glu Lys Leu Arg Ser Lys
             130                 135                 140

Arg Glu Ser Glu Lys Thr Pro Val Ser Lys Glu Thr Gln Pro Leu
145                 150                 155                 160

Pro Ala Ser Arg Gly Val Arg Ser Ser Ala Arg Ser Ala Asp Arg Ala
                 165                 170                 175

Ala Ala Lys Asp Asp Ala Leu Asn Glu Leu Arg Ala Lys Arg Met Lys
             180                 185                 190

Gln Gln Asp Pro Ala Ala Leu Arg Lys Leu Arg Asp Ala Ser Lys Gly
             195                 200                 205

Gly Ser Gly Ser Arg Asp Phe Ser Ser Thr Lys Arg Lys Pro Leu Ala
             210                 215                 220

Ser Ser Asn Leu Ser Ser Ser Gln Ser Asp Ser Asp Ser Arg Ser
225                 230                 235                 240

Gln Ser Asp Asp Glu Gly Ser Asn Gly Gly Met Leu Asp Ser Asp
                 245                 250                 255

Asp Arg Ser Asp Val Pro Thr Phe Glu Asp Val Lys Glu Val Thr Ile
             260                 265                 270

Arg Arg Ser Lys Leu Ala Lys Trp Leu Met Glu Pro Phe Phe Glu Glu
             275                 280                 285

Leu Ile Val Gly Cys Phe Val Arg Val Gly Ile Gly Arg Ser Lys Ser
             290                 295                 300

Gly Pro Ile Tyr Arg Leu Cys Trp Val Lys Asn Val Asp Ala Thr Asp
305                 310                 315                 320

Pro Asp Lys Thr Tyr Lys Leu Glu Asn Lys Thr Thr His Lys Tyr Leu
             325                 330                 335

Asn Val Val Trp Gly Asn Glu Thr Ser Ala Ala Arg Trp Gln Met Ala
             340                 345                 350

Met Ile Ser Asp Gly His Pro Leu Glu Glu Tyr Arg Gln Trp Ile
             355                 360                 365

Arg Glu Val Glu Arg Thr Asn Gly Arg Met Pro Thr Lys Gln Asp Ile
             370                 375                 380

Ser Glu Lys Lys Glu Ala Ile Gln Arg Thr Asn Ser Phe Val Tyr Ser
385                 390                 395                 400

Ala Glu Thr Val Lys Gln Met Leu Gln Glu Lys Lys Ser Ala Ser Val
                 405                 410                 415

Arg Pro Met Asn Val Ala Ala Glu Lys Asp Arg Leu Lys Glu Leu
                 420                 425                 430

Glu Ile Ala Gln Ser Lys Asn Asp Glu Ala Gly Val Glu Arg Ile Lys
             435                 440                 445

Ser Lys Ile Lys Gln Leu Asp Ala Ser Arg Asn Lys Lys Gly Val Asp
             450                 455                 460

Lys Lys Ala Leu Lys Leu Ala Glu Met Asn Lys Lys Asn Arg Ala Glu
465                 470                 475                 480

Asn Phe Lys Asn Ala Ser Glu Val Lys Ser Ile Thr Ala Ser Leu Lys
                 485                 490                 495

Ala Gly Glu Ala Gly Tyr Asp Pro Phe Ser Arg Arg Trp Thr Arg Ser
             500                 505                 510

Ser Asn Tyr Tyr Asn Gly Lys Asn Lys Gly Lys Asp Gly Glu Glu Asn
```

-continued

```
                515                 520                 525
Glu Ala Ala Val Ala Ala Val Glu Thr Asn Gly Ala Asp Ala Gly
            530                 535                 540
Ala Gly Val Glu Ala Thr Glu Ala Ala Leu Glu Ala Ala Glu Ala
545                 550                 555                 560
Gly Lys Leu Ile Asp Thr Arg Ala Pro Ile Gly Gln Gly Ala Glu His
                565                 570                 575
Asn Gln Leu His Asn Phe Glu Leu Ser Leu Ser Thr Ala Leu Gln
            580                 585                 590
Lys Tyr Gly Gly Pro Gln Gly Val Gln Lys Ala Phe Met Ala Arg Lys
        595                 600                 605
Gln Leu Thr Glu Ala Thr Val Gly Cys Arg Val Ala Glu Asn Asp Gly
        610                 615                 620
Lys Arg His Gly Leu Thr Leu Thr Val Ser Asp Tyr Lys Arg Arg Arg
625                 630                 635                 640
Gly Leu Leu

<210> SEQ ID NO 14
<211> LENGTH: 852
<212> TYPE: PRT
<213> ORGANISM: Arabidopsis thaliana

<400> SEQUENCE: 14

Met Asp Leu Gln Ala Asn Asp Ser Ile Gly Met Arg Lys Gly Met Asp
1               5                   10                  15
Arg Met Gln Gln Ala Phe Glu Ile Tyr Pro Tyr Cys Ala Ser Ala Leu
            20                  25                  30
Asn Tyr Leu Ala Asn His Phe Phe Thr Gly Gln His Phe Leu Val
        35                  40                  45
Glu Gln Leu Thr Glu Thr Ala Leu Ala Val Thr Thr His Gly Pro Thr
    50                  55                  60
Lys Ser His Ser Phe Tyr Asn Leu Ala Arg Ser Tyr His Ser Lys Gly
65                  70                  75                  80
Asp Phe Glu Lys Ala Gly Met Tyr Tyr Met Ala Ala Ile Lys Glu Thr
                85                  90                  95
Asn Asn Asn Pro His Glu Phe Val Phe Pro Tyr Phe Gly Leu Gly Gln
            100                 105                 110
Val Gln Leu Lys Leu Gly Glu Leu Lys Gly Ser Val Phe Asn Phe Glu
        115                 120                 125
Lys Val Leu Glu Val Tyr Pro Asp Asn Cys Glu Thr Leu Lys Ala Leu
    130                 135                 140
Gly His Leu Tyr Thr Gln Leu Gly Gln Asn Glu Lys Ala Leu Glu Tyr
145                 150                 155                 160
Met Arg Lys Ala Thr Lys Leu Asp Pro Arg Asp Ala Gln Ala Phe Val
                165                 170                 175
Gly Leu Gly Glu Leu Leu Ile Ser Ser Asp Thr Gly Ala Ala Leu Asp
            180                 185                 190
Ala Phe Lys Met Ala Arg Thr Leu Met Lys Lys Gly Gln Glu Val
        195                 200                 205
Pro Ile Glu Val Leu Asn Asp Ile Gly Ala Leu His Phe Glu Arg Glu
    210                 215                 220
Glu Phe Glu Ser Ala Leu Glu Asn Phe Lys Glu Ala Leu Gly Asp Gly
225                 230                 235                 240
Ile Trp Ile Ser Phe Leu Asp Glu Lys Glu Asn Leu Glu Gln Thr Gly
```

-continued

```
                245                 250                 255
Val Ser Val Leu Gly Tyr Lys Asp Thr Gly Ile Phe His Arg Leu Ile
            260                 265                 270

Glu Ser Gly His Ser Val Asp Val Pro Trp Asn Lys Val Thr Thr Leu
            275                 280                 285

Phe Asn Leu Ala Arg Leu Leu Glu Gln Ile His Lys Thr Glu Ala Ala
            290                 295                 300

Thr Phe Met Tyr Arg Leu Ile Leu Phe Lys Tyr Pro Gly Tyr Ile Asp
305                 310                 315                 320

Ala Tyr Leu Arg Leu Ala Ala Ser Ala Lys Ala Gln Asn Asn Leu Pro
                325                 330                 335

Leu Ala Ile Glu Leu Val Asn Glu Ala Leu Lys Val Asp Asp Lys Asn
            340                 345                 350

Pro Asn Ala Leu Ser Leu Leu Gly Glu Leu Glu Leu Lys Asn Asp Asp
            355                 360                 365

Trp Val Lys Ala Lys Glu Thr Phe Arg Ala Ala Asn Asp Ala Thr Asp
            370                 375                 380

Gly Lys Asp Ser Tyr Ala Ile Leu Ser Leu Gly Asn Trp Asn Tyr Phe
385                 390                 395                 400

Ala Ala Met Arg Asn Glu Lys Arg Asn Pro Lys Leu Glu Ala Thr His
                405                 410                 415

Leu Glu Lys Ala Lys Glu Leu Tyr Thr Lys Val Leu Thr Gln His Asn
                420                 425                 430

Ser Asn Met Tyr Ala Ala Asn Gly Ser Gly Ile Val Leu Ala Glu Lys
            435                 440                 445

Gly Gln Phe Asp Ile Ala Lys Asp Val Phe Thr Gln Val Gln Glu Ala
            450                 455                 460

Ala Ser Gly Ser Val Phe Leu Gln Met Pro Asp Val Trp Asn Leu
465                 470                 475                 480

Ala His Val Tyr Phe Ala Gln Gly Asn Phe Ala Leu Thr Val Lys Met
                485                 490                 495

Tyr Gln Asn Cys Leu Arg Lys Phe Phe Tyr Asn Thr Asp Ser Gln Ile
            500                 505                 510

Leu Leu Tyr Leu Ala Arg Thr His Tyr Glu Ala Glu Gln Trp Gln Glu
            515                 520                 525

Cys Lys Lys Thr Leu Leu Arg Ala Ile His Leu Thr Pro Ser Asn Tyr
            530                 535                 540

Thr Phe Arg Phe Asp Leu Gly Ala Val Met Gln Lys Ser Ser Ser Ser
545                 550                 555                 560

Thr Leu Gln Lys Lys Lys Arg Thr Ala Asp Glu Val Arg Ser Thr Val
                565                 570                 575

Ala Glu Ala Glu Asn Ala Val Arg Val Phe Thr Gln Leu Ser Ala Ala
            580                 585                 590

Ser Asp Leu His Val His Gly Phe Asp Ser Lys Lys Ile Gln Thr His
            595                 600                 605

Val Gln Tyr Cys Ser His Leu Leu Glu Ala Ala Lys Val His Arg Glu
            610                 615                 620

Ala Ala Glu Gln Glu Glu Leu Gln Asn Arg Gln Arg Leu Glu Val Ala
625                 630                 635                 640

Arg Gln Ala Ala Leu Ala Glu Glu Ala Arg Lys Ala Glu Glu Gln
                645                 650                 655

Arg Lys Tyr Gln Leu Glu Lys Arg Lys Gln Glu Glu Leu Arg Arg
            660                 665                 670
```

```
Leu Lys Gln Glu Glu Lys Phe Gln Arg Ile Lys Glu Gln Trp Lys
        675                 680                 685

Ser Ser Thr Pro Gly Ser Asn Lys Arg Lys Asp Arg Val Glu Asp Asp
    690                 695                 700

Asp Gly Glu Ser Lys Pro Ser Glu Arg Arg Lys Lys Gly Gly Lys
705                 710                 715                 720

Arg Arg Lys Lys Asp Lys Ser Ser Arg Ala Arg His Tyr Glu Asp Asp
                725                 730                 735

Glu Glu Glu Ala Ala Thr Met Asp Asp His Asn Glu Val Glu Asp Glu
            740                 745                 750

Asp Ala Asn Thr Asn Tyr Asn Arg Glu Asp Glu Met Thr Thr Gln Glu
        755                 760                 765

Ala Glu Glu Pro Val Asp Asp Ala His Asp Leu Leu Ala Ala
    770                 775                 780

Gly Leu Glu Asp Pro Asp Val Asp Asp Asp Glu Val Pro Thr Ser Gly
785                 790                 795                 800

Val Arg Arg Arg Arg Ala Leu Ser Ser Ser Asp Glu Glu Gly Glu Leu
                805                 810                 815

Met Glu Glu Ser His Pro Asn Ser Ser Pro Gln Lys Glu Lys Glu Glu
            820                 825                 830

Ser Asn Gly Glu Ala Gly Asp Pro Asn Met Glu Glu Glu Glu
        835                 840                 845

Glu Glu Ala Asn
    850

<210> SEQ ID NO 15
<211> LENGTH: 501
<212> TYPE: PRT
<213> ORGANISM: Arabidopsis thaliana

<400> SEQUENCE: 15

Met Asp Leu Gln Ala Asn Asp Ser Ile Gly Met Arg Lys Gly Met Asp
1               5                   10                  15

Arg Met Gln Gln Ala Phe Glu Ile Tyr Pro Tyr Cys Ala Ser Ala Leu
            20                  25                  30

Asn Tyr Leu Ala Asn His Phe Phe Thr Gly Gln His Phe Leu Val
        35                  40                  45

Glu Gln Leu Thr Glu Thr Ala Leu Ala Val Thr Thr His Gly Pro Thr
    50                  55                  60

Lys Ser His Ser Phe Tyr Asn Leu Ala Arg Ser Tyr His Ser Lys Gly
65                  70                  75                  80

Asp Phe Glu Lys Ala Gly Met Tyr Tyr Met Ala Ala Ile Lys Glu Thr
                85                  90                  95

Asn Asn Asn Pro His Glu Phe Val Phe Pro Tyr Phe Gly Leu Gly Gln
            100                 105                 110

Val Gln Leu Lys Leu Gly Glu Leu Lys Gly Ser Val Phe Asn Phe Glu
        115                 120                 125

Lys Val Leu Glu Val Tyr Pro Asp Asn Cys Glu Thr Leu Lys Ala Leu
    130                 135                 140

Gly His Leu Tyr Thr Gln Leu Gly Gln Asn Glu Lys Ala Leu Glu Tyr
145                 150                 155                 160

Met Arg Lys Ala Thr Lys Leu Asp Pro Arg Asp Ala Gln Ala Phe Val
                165                 170                 175

Gly Leu Gly Glu Leu Leu Ile Ser Ser Asp Thr Gly Ala Ala Leu Asp
```

```
                180             185             190
Ala Phe Lys Met Ala Arg Thr Leu Met Lys Gly Gly Gln Glu Val
            195             200             205
Pro Ile Glu Val Leu Asn Asp Ile Gly Ala Leu His Phe Glu Arg Glu
210             215             220
Glu Phe Glu Ser Ala Leu Glu Asn Phe Lys Glu Ala Leu Gly Asp Gly
225             230             235             240
Ile Trp Ile Ser Phe Leu Asp Glu Lys Glu Asn Leu Glu Gln Thr Gly
                245             250             255
Val Ser Val Leu Gly Tyr Lys Asp Thr Gly Ile Phe His Arg Leu Ile
            260             265             270
Glu Ser Gly His Ser Val Asp Val Pro Trp Asn Lys Val Thr Thr Leu
            275             280             285
Phe Asn Leu Ala Arg Leu Leu Glu Gln Ile His Lys Thr Glu Ala Ala
        290             295             300
Thr Phe Met Tyr Arg Leu Ile Leu Phe Lys Tyr Pro Gly Tyr Ile Asp
305             310             315             320
Ala Tyr Leu Arg Leu Ala Ala Ser Ala Lys Ala Gln Asn Asn Leu Pro
                325             330             335
Leu Ala Ile Glu Leu Val Asn Glu Ala Leu Lys Val Asp Asp Lys Asn
            340             345             350
Pro Asn Ala Leu Ser Leu Leu Gly Glu Leu Glu Leu Lys Asn Asp Asp
            355             360             365
Trp Val Lys Ala Lys Glu Thr Phe Arg Ala Ala Asn Asp Ala Thr Asp
370             375             380
Gly Lys Asp Ser Tyr Ala Ile Leu Ser Leu Gly Asn Trp Asn Tyr Phe
385             390             395             400
Ala Ala Met Arg Asn Glu Lys Arg Asn Pro Lys Leu Glu Ala Thr His
                405             410             415
Leu Glu Lys Ala Lys Glu Leu Tyr Thr Lys Val Leu Thr Gln His Asn
            420             425             430
Ser Asn Met Tyr Ala Ala Asn Gly Ser Gly Ile Val Leu Ala Glu Lys
            435             440             445
Gly Gln Phe Asp Ile Ala Lys Asp Val Phe Thr Gln Val Gln Glu Ala
        450             455             460
Ala Ser Gly Ser Val Phe Leu Gln Met Pro Asp Val Trp Val Asn Leu
465             470             475             480
Ala His Val Tyr Phe Ala Gln Gly Asn Phe Ala Leu Thr Val Lys Met
                485             490             495
Val Cys His Phe Ile
            500

<210> SEQ ID NO 16
<211> LENGTH: 501
<212> TYPE: PRT
<213> ORGANISM: Arabidopsis thaliana

<400> SEQUENCE: 16

Met Asp Leu Gln Ala Asn Asp Ser Ile Gly Met Arg Lys Gly Met Asp
1               5               10              15
Arg Met Gln Gln Ala Phe Glu Ile Tyr Pro Tyr Cys Ala Ser Ala Leu
            20              25              30
Asn Tyr Leu Ala Asn His Phe Phe Thr Gly Gln His Phe Leu Val
        35              40              45
```

-continued

```
Glu Gln Leu Thr Glu Thr Ala Leu Ala Val Thr Thr His Gly Pro Thr
 50                  55                  60
Lys Ser His Ser Phe Tyr Asn Leu Ala Arg Ser Tyr His Ser Lys Gly
 65                      70                  75                  80
Asp Phe Glu Lys Ala Gly Met Tyr Tyr Met Ala Ile Lys Glu Thr
                 85                  90                  95
Asn Asn Asn Pro His Glu Phe Val Phe Pro Tyr Phe Gly Leu Gly Gln
            100                 105                 110
Val Gln Leu Lys Leu Gly Glu Leu Lys Gly Ser Val Phe Asn Phe Glu
            115                 120                 125
Lys Val Leu Glu Val Tyr Pro Asp Asn Cys Glu Thr Leu Lys Ala Leu
            130                 135                 140
Gly His Leu Tyr Thr Gln Leu Gly Gln Asn Glu Lys Ala Leu Glu Tyr
145                 150                 155                 160
Met Arg Lys Ala Thr Lys Leu Asp Pro Arg Asp Ala Gln Ala Phe Val
                165                 170                 175
Gly Leu Gly Glu Leu Leu Ile Ser Ser Asp Thr Gly Ala Ala Leu Asp
            180                 185                 190
Ala Phe Lys Met Ala Arg Thr Leu Met Lys Lys Gly Gly Gln Glu Val
            195                 200                 205
Pro Ile Glu Val Leu Asn Asp Ile Gly Ala Leu His Phe Glu Arg Glu
210                 215                 220
Glu Phe Glu Ser Ala Leu Glu Asn Phe Lys Glu Ala Leu Gly Asp Gly
225                 230                 235                 240
Ile Trp Ile Ser Phe Leu Asp Glu Lys Glu Asn Leu Glu Gln Thr Gly
                245                 250                 255
Val Ser Val Leu Gly Tyr Lys Asp Thr Gly Ile Phe His Arg Leu Ile
            260                 265                 270
Glu Ser Gly His Ser Val Asp Val Pro Trp Asn Lys Val Thr Thr Leu
            275                 280                 285
Phe Asn Leu Ala Arg Leu Leu Glu Gln Ile His Lys Thr Glu Ala Ala
290                 295                 300
Thr Phe Met Tyr Arg Leu Ile Leu Phe Lys Tyr Pro Gly Tyr Ile Asp
305                 310                 315                 320
Ala Tyr Leu Arg Leu Ala Ala Ser Ala Lys Ala Gln Asn Asn Leu Pro
                325                 330                 335
Leu Ala Ile Glu Leu Val Asn Glu Ala Leu Lys Val Asp Asp Lys Asn
            340                 345                 350
Pro Asn Ala Leu Ser Leu Leu Gly Glu Leu Glu Leu Lys Asn Asp Asp
            355                 360                 365
Trp Val Lys Ala Lys Glu Thr Phe Arg Ala Ala Asn Asp Ala Thr Asp
            370                 375                 380
Gly Lys Asp Ser Tyr Ala Ile Leu Ser Leu Gly Asn Trp Asn Tyr Phe
385                 390                 395                 400
Ala Ala Met Arg Asn Glu Lys Arg Asn Pro Lys Leu Glu Ala Thr His
                405                 410                 415
Leu Glu Lys Ala Lys Glu Leu Tyr Thr Lys Val Leu Thr Gln His Asn
            420                 425                 430
Ser Asn Met Tyr Ala Ala Asn Gly Ser Gly Ile Val Leu Ala Glu Lys
            435                 440                 445
Gly Gln Phe Asp Ile Ala Lys Asp Val Phe Thr Gln Val Gln Glu Ala
            450                 455                 460
Ala Ser Gly Ser Val Phe Leu Gln Met Pro Asp Val Trp Val Asn Leu
```

```
            465                 470                 475                 480
Ala His Val Tyr Phe Ala Gln Gly Asn Phe Ala Leu Thr Val Lys Met
                485                 490                 495

Val Cys His Phe Ile
        500
```

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
atggacgaaa ggagagtgaa ag                                        22

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
ggaatcagaa tatgagacgg aag                                       23

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
aggcaaacac aagctcacta tc                                        22

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
ttgcaggtgg aagtagtgcc tc                                        22

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
tgtcatcaga gacactagca agtcg                                     25

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
gccactgccg ccagttttat caag                                      24

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
tggtgttcct tcaaacttta gg                                              22

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gctcaatcag tcattgcact c                                               21

<210> SEQ ID NO 25
<211> LENGTH: 33
<212> TYPE: DNA
<213> ORGANISM: Artificial Sequence
<220> FEATURE:
<223> OTHER INFORMATION: Synthetic

<400> SEQUENCE: 25
aaaggatcca tgaaactcgc aggtctgaaa tcg                                   33

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
aaaggatccg aattgttcat gagtaatcat agagc                                35

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
ggatcatcag tccaaaagct ctg                                             23

<210> SEQ ID NO 28
<211> LENGTH: 24
<212> TYPE: DNA
<213> ORGANISM: Artificial Sequence
<220> FEATURE:
<223> OTHER INFORMATION: Synthetic

<400> SEQUENCE: 28
agtatcacac acaaagtctc ttgg                                            24

<210> SEQ ID NO 29
<211> LENGTH: 24
<212> TYPE: DNA
<213> ORGANISM: Artificial Sequence
<220> FEATURE:

```
<223> OTHER INFORMATION: Synthetic

<400> SEQUENCE: 29
cgcactcatc gtcttctcta gccg                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
tcactcccgg ccatttcctt cagc                                              24

<210> SEQ ID NO 31
<211> LENGTH: 33
<212> TYPE: DNA
<213> ORGANISM: Artificial Sequence
<220> FEATURE:
<223> OTHER INFORMATION: Synthetic

<400> SEQUENCE: 31
aaaggatcca atgccatccc tgacatggct tgc                                    33

<210> SEQ ID NO 32
<211> LENGTH: 57
<212> TYPE: PRT
<213> ORGANISM: Arabidopsis thaliana

<400> SEQUENCE: 32

Met Lys Leu Ala Gly Leu Lys Ser Ile Glu Asn Ala His Glu Asp Ser
1               5                   10                  15

Val Trp Ala Ala Thr Trp Val Pro Ala Thr Glu Asp Arg Pro Ala Leu
                20                  25                  30

Leu Leu Thr Gly Ser Leu Asp Glu Thr Val Lys Leu Trp Arg Pro Asp
            35                  40                  45

Glu Leu Asp Leu Val Arg Thr Asn Thr
    50                  55

<210> SEQ ID NO 33
<211> LENGTH: 42
<212> TYPE: PRT
<213> ORGANISM: Arabidopsis thaliana

<400> SEQUENCE: 33

Gly His Ser Leu Gly Val Ala Ala Leu Ala Ala His Pro Ser Gly Ile
1               5                   10                  15

Ile Ala Ala Ser Ser Ser Ile Asp Ser Phe Val Arg Val Phe Asp Val
                20                  25                  30

Asp Thr Asn Ala Thr Ile Ala Val Leu Glu
            35                  40

<210> SEQ ID NO 34
<211> LENGTH: 56
<212> TYPE: PRT
<213> ORGANISM: Arabidopsis thaliana

<400> SEQUENCE: 34

Ala Pro Pro Ser Glu Val Trp Gly Met Gln Phe Glu Pro Lys Gly Thr
1               5                   10                  15

Ile Leu Ala Val Ala Gly Gly Ser Ser Ala Ser Val Lys Leu Trp Asp
```

-continued

```
                    20                  25                  30
Thr Ala Ser Trp Arg Leu Ile Ser Thr Leu Ser Ile Pro Arg Pro Asp
            35                  40                  45
Ala Pro Lys Pro Ser Asp Lys Thr
        50                  55

<210> SEQ ID NO 35
<211> LENGTH: 42
<212> TYPE: PRT
<213> ORGANISM: Arabidopsis thaliana

<400> SEQUENCE: 35

Ser Ser Lys Lys Phe Val Leu Ser Val Ala Trp Ser Pro Asn Gly Lys
1               5                   10                  15
Arg Leu Ala Cys Gly Ser Met Asp Gly Thr Ile Cys Val Phe Asp Val
            20                  25                  30
Asp Arg Ser Lys Leu Leu His Gln Leu Glu
        35                  40

<210> SEQ ID NO 36
<211> LENGTH: 43
<212> TYPE: PRT
<213> ORGANISM: Arabidopsis thaliana

<400> SEQUENCE: 36

Gly His Asn Met Pro Val Arg Ser Leu Val Phe Ser Pro Val Asp Pro
1               5                   10                  15
Arg Val Leu Phe Ser Gly Ser Asp Asp Gly His Val Asn Met His Asp
            20                  25                  30
Ala Glu Gly Lys Thr Leu Leu Gly Ser Met Ser
        35                  40

<210> SEQ ID NO 37
<211> LENGTH: 42
<212> TYPE: PRT
<213> ORGANISM: Arabidopsis thaliana

<400> SEQUENCE: 37

Gly His Thr Ser Trp Val Leu Ser Val Asp Ala Ser Pro Asp Gly Gly
1               5                   10                  15
Ala Ile Ala Thr Gly Ser Ser Asp Arg Thr Val Arg Leu Trp Asp Leu
            20                  25                  30
Lys Met Arg Ala Ala Ile Gln Thr Met Ser
        35                  40

<210> SEQ ID NO 38
<211> LENGTH: 39
<212> TYPE: PRT
<213> ORGANISM: Arabidopsis thaliana

<400> SEQUENCE: 38

Asn His Asn Asp Gln Val Trp Ser Val Ala Phe Arg Pro Pro Gly Gly
1               5                   10                  15
Thr Gly Val Arg Ala Gly Arg Leu Ala Ser Val Ser Asp Asp Lys Ser
            20                  25                  30
Val Ser Leu Tyr Asp Tyr Ser
        35

<210> SEQ ID NO 39
<211> LENGTH: 30
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X can be Gly or Ala.
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: X can be Val or Ile.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: X can be Val, Leu, Ile, or Cys.
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X can be Phe, Trp, Leu, Ile, or Val.
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X can be Pro, Ser, or Asp.
<220> FEATURE:
<221> NAME/KEY: MISC_FEATURE
<222> LOCATION: (14)..(14)
<223> OTHER INFORMATION: X can be Asp, Asn, or Ser.
<220> FEATURE:
<221> NAME/KEY: MISC_FEATURE
<222> LOCATION: (15)..(15)
<223> OTHER INFORMATION: X can be Gly, Ser, or Pro.
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: X can be Leu, Ile, Val, or Phe.
<220> FEATURE:
<221> NAME/KEY: MISC_FEATURE
<222> LOCATION: (18)..(18)
<223> OTHER INFORMATION: X can be Ala, Val, Leu, or Ile.
<220> FEATURE:
<221> NAME/KEY: MISC_FEATURE
<222> LOCATION: (19)..(19)
<223> OTHER INFORMATION: X can be Ser or Thr.
<220> FEATURE:
<221> NAME/KEY: MISC_FEATURE
<222> LOCATION: (20)..(20)
<223> OTHER INFORMATION: X can be Gly, Ala, Ser, or Cys.
<220> FEATURE:
<221> NAME/KEY: MISC_FEATURE
<222> LOCATION: (21)..(21)
<223> OTHER INFORMATION: X can be Ser, Gly, or Ala.
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
```

```
<223> OTHER INFORMATION: Xaa can be any naturally occurring amino acid
<220> FEATURE:
<221> NAME/KEY: MISC_FEATURE
<222> LOCATION: (25)..(25)
<223> OTHER INFORMATION: X can be Thr or Ser.
<220> FEATURE:
<221> NAME/KEY: MISC_FEATURE
<222> LOCATION: (26)..(26)
<223> OTHER INFORMATION: X can be Ile, Val, Leu, or Ala.
<220> FEATURE:
<221> NAME/KEY: MISC_FEATURE
<222> LOCATION: (27)..(27)
<223> OTHER INFORMATION: X can be Lys or Arg.
<220> FEATURE:
<221> NAME/KEY: MISC_FEATURE
<222> LOCATION: (28)..(28)
<223> OTHER INFORMATION: X can be Val, Leu, or Ile.
<220> FEATURE:
<221> NAME/KEY: MISC_FEATURE
<222> LOCATION: (29)..(29)
<223> OTHER INFORMATION: X can be Trp, Phe, or Tyr.
<220> FEATURE:
<221> NAME/KEY: MISC_FEATURE
<222> LOCATION: (30)..(30)
<223> OTHER INFORMATION: X can be Asp or Asn.

<400> SEQUENCE: 39

Xaa His Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Asp Xaa Xaa Xaa Xaa Xaa Xaa Xaa
            20                  25                  30
```

PLANT *VERNALIZATION INDEPENDENCE* (VIP) GENES, PROTEINS, AND METHODS OF USE

The present application claims priority to U.S. patent application Ser. No. 60/376,765, filed May 1, 2002, which is hereby incorporated by reference in its entirety.

The present application was funded in part with government support under grant number 61-4229 from the United States Department of Agriculture National Research Initiative Competitive Grants Program. The government may have certain rights in this invention.

FIELD OF THE INVENTION

The present invention relates to plant genes involved in regulating flowering, and especially to genes involved in the induction of flowering in response to cold, or vernalization.

BACKGROUND OF THE INVENTION

Of the myriads of developmental processes that define plant form and function, flowering is of exceptional interest to horticulturalists. The vast majority of horticulturally important crops are in some way dependent upon flowering, whether the flower is the primary goal of production, or is simply required for a crop to be produced. Much effort is currently expended into regulating the timing of flowering. In floriculture crops, the interest is in abbreviating or extending the vegetative phase in order to create an aesthetically pleasing balance between leaves and flowers, or to conveniently induce or repress flowering to take advantage of market potential. In ornamental foliage plants, and agronomically important plants that are grown for their leaf tissue (such as lettuce, spinach, and other greens), it is highly desirable to suppress flowering as long as possible. In other agronomically important plants grown for their seed products (such as fruits and vegetables as diverse as beans, peas, corn, and tomatoes), decreasing or increasing the time to flowering might expand the range where these crops could be grown, and might allow more precise control of nutrient flow to the crop. Also, in woody plants, there is a great deal of interest in finding means to abbreviate the vegetative phase, which in most species can last ten or more years and is probably the single most limiting factor for germplasm improvement through traditional breeding techniques.

Most efforts at controlling flowering time have involved manipulation of environmental conditions or the application of synthetic growth regulators. However, these approaches can increase production costs and labor requirements. In addition, the use of many traditionally utilized chemical compounds is becoming restricted. Alternative approaches to manipulate flowering, including the use of biotechnology, will require a better understanding of the associated molecular mechanisms.

The physiology and phenomenology of the developmental transition from vegetative growth to reproductive growth, or flowering, has been studied for many years, but only in the last decade have the molecular mechanisms come under examination. Flowering is ultimately determined by genes that govern the identity of the meristem, promoting or repressing a floral fate as opposed to a shoot or vegetative fate. There is incredible diversity of flowering strategies employed in nature, and it is becoming apparent that flowering at the molecular level involves an extraordinarily complex web of interactive pathways.

Although many genes have been identified that are involved in the regulation of flowering, it is clear that many more remain to be identified. Moreover, few of the identified genes have been cloned, and even fewer have been characterized as to their role in regulating flowering. Therefore, it would be useful to identify genes involved in flowering, to clone such genes, and to characterize the role of the genes in flowering. These genes would be useful in further understanding the regulation of flowering, as well as in the control of flowering in horticulturally important plants.

SUMMARY OF THE INVENTION

It is an objective of the present invention to identify genes involved in flowering, and in particular to identify genes involved in vernalization, to clone such genes, and to characterize the role of the genes in vernalization and flowering.

These objectives and more are met by the present invention, which provides isolated genes (VIP genes) in which a mutation results in vernalization independence, or constitutive vernalization, in a genetic background where the wild type or non-mutant phenotype requires vernalization to induce flowering, and also exhibits decreased FLC RNA expression in the absence of cold. Vernalization independence, or constitutive vernalization, is a plant phenotype exhibited by mutants that flower early and without the requirement for vernalization, or exposure to a sufficient period of cold to induce flowering, in a genetic background where the wild type or non-mutant phenotype requires vernalization to induce flowering. In particular, the present invention provides the identification, cloning, characterization of genes involved in vernalization, or VERNALIZATION INDEPENDENCE (VIP) genes, as well as to the proteins encoded by these genes, and to methods of using VIP genes and proteins.

Thus, in some embodiments, the present invention provides an isolated nucleic acid sequence comprising a first nucleic acid sequence encoding a VIP polypeptide. In some further embodiments, the encoded VIP polypeptide is VIP3, VIP4, VIP5, or VIP6. In some further embodiments, the first nucleic acid sequence encoding a VIP polypeptide is SEQ ID NO: 1, 2, 3, 4, 7, 8, 9, 10, 11, or 12. In yet other embodiments, the present invention provides a nucleic acid sequence encoding a variant of a VIP polypeptide, wherein the variant has VIP activity; in some embodiments, the activity is increased or decreased relative to the non-variant VIP polypeptide activity. In other embodiments, the present invention provides an isolated nucleic acid sequence comprising a second nucleic acid sequence which is complementary to a first nucleic acid sequence encoding a VIP polypeptide. In yet other embodiments, the present invention provides an isolated nucleic acid sequence comprising a second nucleic acid sequence which hybridizes under conditions of high stringency to a first nucleic acid sequence encoding a VIP polypeptide, wherein the second nucleic acid sequence encodes a VIP polypeptide.

In still other embodiments, the present invention provides an isolated nucleic acid sequence comprising a second nucleic acid sequence which encodes a nucleic acid product which interferes with the expression of a first nucleic acid sequence encoding a VIP polypeptide, wherein the interference is based upon a coding sequence of the VIP polypeptide encoded by the first nucleic acid sequence. In some further embodiments, the second nucleic acid sequence encodes an antisense sequence of the first nucleic acid sequence encoding a VIP polypeptide. In some other further embodiments, the second nucleic acid sequence encodes an RNA product which interferes with expression of the first nucleic acid sequence encoding a VIP polypeptide.

In yet other embodiments, the present invention provides a composition comprising any of the nucleic acid sequences described above.

In other embodiments, the present invention provides a purified VIP polypeptide. In some embodiments, the purified VIP polypeptide is encoded by any of the nucleic acid sequences described above. In other embodiments, the purified VIP polypeptide is VIP3, VIP4, VIP5, or VIP6. In some further embodiments, the purified polypeptide comprises amino acid sequence SEQ ID NO:5, 6, 13, 14, 15, or 16. In yet other embodiments, the present invention provides a variant of a VIP polypeptide, wherein the variant has VIP activity; in some embodiments, the activity is increased or decreased relative to the activity of the non-variant VIP polypeptide. In yet other embodiments, the present invention provides a purified variant of a VIP polypeptide as described above. In other embodiments, the present invention provides a composition comprising any of the purified polypeptides described above The present invention also provides any of the isolated nucleic acid sequences described above operably linked to a promoter. In some embodiments, the promoter is a heterologous promoter. In other embodiments, the promoter is a plant promoter. The present invention also provides a vector comprising any of the nucleic acid sequences described above. In some embodiments, the vector is a cloning vector; in other embodiments, the vector is an expression vector. In some further embodiments, the nucleic acid sequence in the vector is linked to a promoter. In some further embodiments, the promoter is a heterologous promoter. In other further embodiments, the promoter is a plant promoter.

The present invention also provides a transgenic host cell comprising any of the nucleic acid sequences of the present invention described above, wherein the nucleic acid sequence is heterologous to the host cell. In some embodiments, the nucleic acid sequence is operably linked to any of the promoters described above. In other embodiments, the nucleic acid is present in any of the vectors described above.

The present invention also provides a transgenic organism comprising any of the nucleic acid sequences of the present invention described above, wherein the nucleic acid sequence is heterologous to the organism. In some embodiments, the nucleic acid sequence is operably linked to any of the promoters described above. In other embodiments, the nucleic acid is present in any of the vectors described above.

The present invention also provides a transgenic plant, a transgenic plant part, a transgenic plant cell, or a transgenic plant seed, comprising any of the nucleic acid sequences of the present invention described above, wherein the nucleic acid sequence is heterologous to the transgenic plant, a transgenic plant part, a transgenic plant cell, or a transgenic plant seed. In some embodiments, the nucleic acid sequence is operably linked to any of the promoters described above. In other embodiments, the nucleic acid is present in any of the vectors described above.

The present invention also provides a method for producing a VIP polypeptide, comprising culturing a transgenic host cell comprising a heterologous nucleic acid sequence, wherein the heterologous nucleic acid sequence is any of the nucleic acid sequences of the present invention described above which encode a VIP polypeptide or variant thereof, under conditions sufficient for expression of the encoded VIP polypeptide, and producing the VIP polypeptide in the transgenic host cell. In some embodiments, the nucleic acid sequence is operably linked to any of the promoters described above. In other embodiments, the nucleic acid is present in any of the vectors described above. The present invention also provides a method for producing a VIP polypeptide, comprising growing a transgenic host cell comprising a heterologous nucleic acid sequence, wherein the heterologous nucleic acid sequence is any of the nucleic acid sequences of the present invention described above encoding a VIP polypeptide or a variant thereof, under conditions sufficient for expression of the encoded VIP polypeptide, and producing the VIP polypeptide in the transgenic host cell.

The present invention also provides a method for altering the phenotype of a plant, comprising providing an expression vector comprising any of the nucleic acid sequences of the present invention described above, and plant tissue, and transfecting the plant tissue with the vector under conditions such that a plant is obtained from the transfected tissue and the nucleic acid sequence is expressed in the plant and the phenotype of the plant is altered. In some embodiments, the nucleic acid sequence encodes a VIP polypeptide or variant thereof. In other embodiments, the nucleic sequence encodes a nucleic acid product which interferes with the expression of a nucleic acid sequence encoding a VIP polypeptide or variant thereof, wherein the interference is based upon the coding sequence of the VIP protein or variant thereof. In some embodiments, the nucleic acid sequence is operably linked to any of the promoters described above. In other embodiments, the nucleic acid is present in any of the vectors described above.

The present invention also provides a method for altering the phenotype of a plant, comprising growing a transgenic plant comprising an expression vector comprising any of the nucleic acid sequences of the present invention described above under conditions such that the nucleic acid sequence is expressed and the phenotype of the plant is altered. In some embodiments, the nucleic acid sequence encodes a VIP polypeptide or variant thereof. In other embodiments, the nucleic sequence encodes a nucleic acid product which interferes with the expression of a nucleic acid sequence encoding a VIP polypeptide or variant thereof, wherein the interference is based upon the coding sequence of the VIP protein or variant thereof. In some embodiments, the nucleic acid sequence is operably linked to any of the promoters described above. In other embodiments, the nucleic acid is present in any of the vectors described above.

DESCRIPTION OF THE FIGURES

FIG. 3 shows the genomic nucleotide sequence of a VIP3 gene (SEQ ID NO:1). This sequence was obtained from the AGI (*Arabidopsis* Genome Initiative) entry, and modified. cDNA sequencing was utilized to determine the 5' and 3' ends of the gene, as well as to confirm the predicted intron/exon junctions. The capital letters represent the VIP3 cDNA sequence (SEQ ID NO:3), where the underlined regions (capital letters) represent the coding region, and the non-underlined regions (capital letters) represent introns.

FIG. 4 shows amino acid sequence of the VIP3 polypeptide (SEQ ID NO:5) encoded by the VIP3 gene shown in FIG. 3. This sequence was obtained from the AGI (*Arabidopsis* Genome Initiative) entry.

FIG. 5 shows nucleic acid sequence of a VIP4 gene (SEQ ID NO:2). This sequence was obtained from the AGI (*Arabidopsis* Genome Initiative) entry, and modified. cDNA sequencing was utilized to determine the 5' and 3' ends of the gene, as well as to confirm the predicted intron/exon junctions. The capital letters represent the VIP4 cDNA sequence (SEQ ID NO:4), where the underlined regions (capital letters) represent the coding region, and the non-underlined regions (capital letters) represent introns.

FIG. 6 shows amino acid sequence of the VIP4 polypeptide (SEQ ID NO:6) encoded by the VIP4 gene shown in FIG. 5. This sequence was obtained from the AGI (*Arabidopsis* Genome Initiative) entry.

FIG. 11 Panel A (SEQ ID NO:32-38) shows the amino acid sequences of the VIP3 (CVN3) protein with WD repeats aligned. The consensus sequence (SEQ ID NO:39) that defines the alignment of the repeats is shown enclosed in a box. This consensus sequence was defined by Smith et al. (1999) (Trends Biochem Sci 24, 181-185), and includes those residues that most frequently occur at a specific position. The letter x signifies that any amino acid can be found at that position. The asterisk represents any polar amino acid. The symbol ~ signifies that additional amino acids can be present at this position in some WD repeats. The position of four, antiparallel β strands, here labeled A, B, C, and D, is based on the structure determined for Gβ. Panel B shows depictions of the WD-motif configurations of the VIP3 (CVN3) protein and a human Gβ (SwissProt accession p04901). Placement of the WD motifs and extent of amino termini are approximately to scale. The degree of amino acid variations from the consensus sequence within the Gβ WD core region is indicated by shading (white, 0 or 1 amino acids; gray, 2 to 4 amino acids; black, 4 to 8 amino acids).

FIG. 12 Panel A shows the genomic nucleotide sequence of a VIP5 gene (SEQ ID NO:7). This sequence was obtained from the AGI (*Arabidopsis* Genome Initiative) entry. Panel B shows the cDNA sequence of the VIP5 gene shown in Panel A (SEQ ID NO:9); cDNA sequencing was utilized to determine the 5' and 3' ends of the gene, as well as to confirm the predicted intron/exon junctions from AGI.

FIG. 13 shows the amino acid sequence of the VIP5 polypeptide (SEQ ID NO:13) encoded by the VIP5 gene shown in FIG. 12. This sequence was obtained from the AGI (*Arabidopsis* Genome Initiative) entry, as well as separately cloned and sequenced.

FIG. 14 Panel A shows the genomic nucleotide sequence of a VIP6 gene (SEQ ID NO:8). This sequence was obtained from the AGI (*Arabidopsis* Genome Initiative) entry. Panel B shows a cloned cDNA sequence of a VIP5 gene which is a short form (SEQ ID NO:10). Panel C shows a cDNA sequence of the VIP5 gene shown in Panel A which is a long form (SEQ ID NO:11). Panel D shows a predicted cDNA sequence as annotated in the AGI database (SEQ ID NO:12). cDNA sequencing was utilized to determine the 5' and 3' ends of the gene, as well as to confirm the predicted intron/exon junctions.

FIG. 15 Panel A shows the amino acid sequence of the VIP6 polypeptide (SEQ ID NO:14) encoded by the short form cDNA of the VIP6 gene shown in FIG. 14, Panel B. Panel B shows the amino acid sequence of the VIP6 polypeptide (SEQ ID NO:15) encoded by the long form cDNA of the VIP6 gene shown in FIG. 14, Panel C. Panel C shows the amino acid sequence of the VIP6 polypeptide (SEQ ID NO:16) encoded by the predicted cDNA from the AGI (*Arabidopsis* Genome Initiative) shown in FIG. 14, Panel D.

DEFINITIONS

Figure 1:
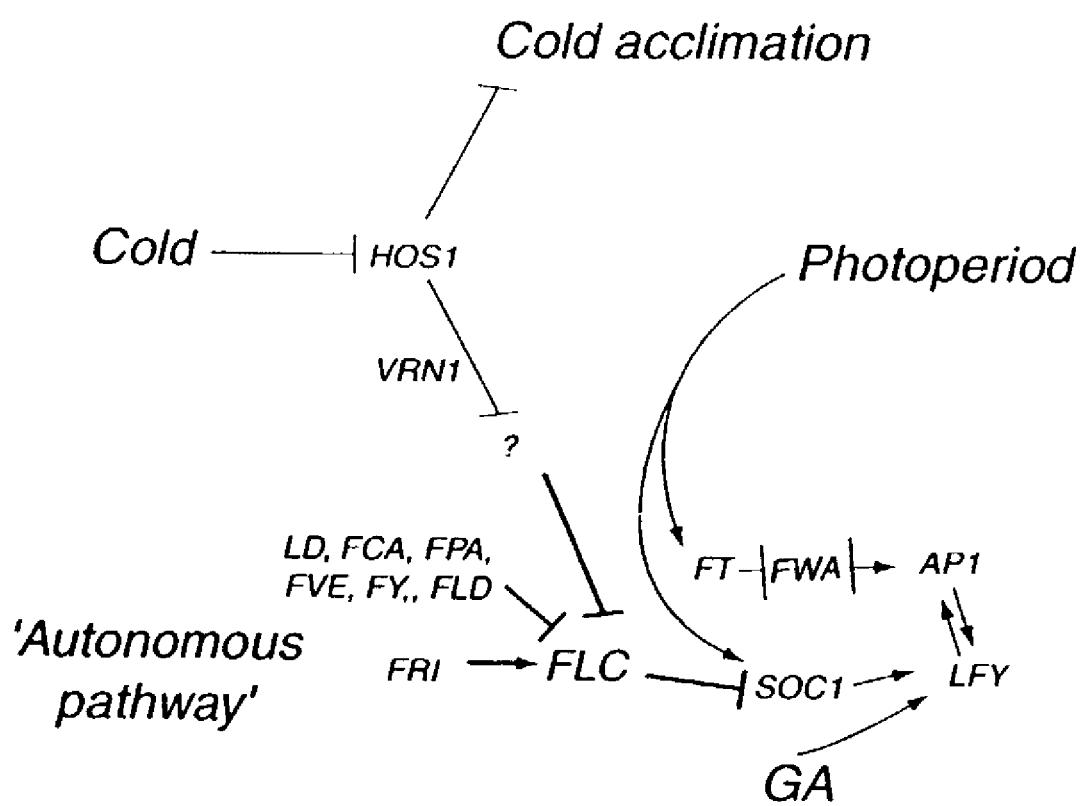
FIG. 1 shows a simplified diagram depicting pathways of cold signal transduction and flowering involving FLC.

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "vernalization" refers to the induction of flowering upon exposure of the plant to a sufficient period of cold.

The terms "vernalization independence" or "independent of vernalization" refer to a plant phenotype exhibited by mutants that flower early and without the requirement for vernalization or exposure to a sufficient period of cold to induce flowering in a genetic background where the wild type or non-mutant phenotype requires vernalization to induce flowering, and that also exhibit decreased FLC RNA expression in the absence of a sufficient period of cold normally required to induce flowering. The terms "constitutive vernalization" or "constitutively vernalized" may be used interchangeably with the terms "vernalization independence" or "independent of vernalization."

The terms "VIP gene" or "VIP" "VERNALIZATION INDEPENDENCE gene" refer to a plant gene in which a knock-out mutation results in vernalization independence, or constitutive vernalization, in a genetic background where the wild type or non-mutant phenotype requires vernalization to induce flowering; the decrease or absence of expression of at least one VIP gene also results in decreased FLC RNA expression in the absence of a sufficient period of cold to induce flowering or vernalization. A VIP gene is not an FLC (FLOWERING LOCUS) gene or an FRI (FRIGIDA) gene. The terms "VIP3 gene" "VIP3," "VIP4 gene" or "VIP4," and the like, refer to specific VIP genes. The present invention identifies seven VIP genes, which are referred to by number, for example, VIP3, VIP4, VIP5, and VIP6. The terms "CVN gene" or "CVN" "CONSTITUTIVE VERNALIZATION gene" or "CONSTITUTIVELY VERNAL-IZED gene" may be used interchangeably with the terms "VIP gene" or "VIP" or "VERNALIZATION INDEPENDENCE gene."

The term "VIP polypeptide" or "VIP" refers to the polypeptide encoded by a VIP gene. The terms "VIP3 polypeptide" or "VIP3" and "VIP4 polypeptide" or "VIP4" refer to the polypeptides encoded by VIP3 and VIP4, respectively. The present invention identifies seven VIP polypeptides encoded by seven VIP genes; these polypeptides are referred to by number, for example, VIP3, VIP4, VIP5, and VIP6. The terms "polypeptide," "protein," "peptide," "encoded product," "amino acid sequence," and the like are used interchangeably. Also, the terms "CVN polypeptide" or "CVN" may be used interchangeably with the terms "VIP polypeptide" or "VIP."

The terms "having VIP activity" or "VIP activity" refers to the activity of a VIP protein naturally occurring in a plant where the wild type or non-mutant phenotype requires vernalization to flower, and where the absence of the protein or the presence of a non-functional protein in the wild-type or non-mutant phenotype, as for example occurs in a mutant phenotype, results in the phenotype of vernalization independence, or constitutive vernalization, and also results in decreased FLC RNA expression in the absence of a sufficient period cold normally required to induce flowering or vernalization. The terms "having CVN activity" or "CVN activity" may be used interchangeably with the terms "having VIP activity" or "VIP activity."

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

The term "portion" when used in reference to a protein (as in "a portion of a given protein") refers to fragments of that protein. The fragments may range in size from four amino acid residues to the entire amino sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" or "homology" when used in reference to a polypeptide refers to a high degree of sequence identity between two polypeptides, or to a high degree of similarity between the three-dimensional structure or to a high degree of similarity between the active site and the mechanism of action. In some embodiments, a homolog has a greater than about 60% sequence identity, and more preferably greater than about 75% sequence identity, and still more preferably greater than about 90% or about 95% or about 98% sequence identity, with a reference sequence. Means of determining homology are described further below.

As applied to polypeptides, the term "substantial identity" means that two peptide sequences, when optimally aligned, as for example by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained.

The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "heterologous" when used in reference to a gene or nucleic acid refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art.

Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids or proteins refers to a degree of identity. There may be partial homology or complete homology. "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.).

A partially homologous nucleic acid sequence is one that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of identity (e.g., less than about 30% identity); in the absence of non-specific binding the probe will not hybridize to the second non-identical target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.*

(U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$□H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$□H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q βreplicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119-127 [1994]) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208, GV3101) are referred to as "nopaline-type" Agrobacteria; *Agrobacterium* strains which cause production of octopine (e.g., strain LBA4404, Ach5, B6) are referred to as "octopine-type" Agrobacteria; and *Agrobacterium* strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a plant or fruit or seed (i.e., a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector which is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementarity is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "posttranscriptional gene silencing" or "PTGS" refers to silencing of gene expression in plants after transcription, and appears to involve the specific degradation of mRNAs synthesized from gene repeats.

The term "cosuppression" refers to silencing of endogenous genes by heterologous genes that share sequence identity with endogenous genes.

The term "overexpression" generally refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "overexpression" and "overexpressing" and grammatical equivalents, are specifically used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, N.Y., pp 9.31-9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DESCRIPTION OF THE INVENTION

The present invention relates to plant genes involved in regulating flowering, and especially to genes involved in the induction of flowering in response to cold, or vernalization. In particular, the present invention provides methods of identifying, cloning, and characterizing genes involved in vernalization independence, or VIP genes. Thus, the presently claimed invention provides compositions comprising isolated VIP genes and coding sequences, and VIP polypeptides, and in particular to isolated VIP3, VIP4, VIP5, and VIP6 genes and coding sequences, and their encoded polypeptides. The present invention also provides methods for using VIP genes, and VIP polypeptides; such methods include but are not limited to use of these genes to promote early flowering, to remove requirements for vernalization in transgenic plants, and to isolate homologous genes in other plants for similar use.

The following description provides a general discussion of the pathways believed to be involved in regulating floral development, with an emphasis on vernalization. It then provides a description of methods for identifying genes involved in vernalization, and of genes discovered through use of these methods, the VIP genes; these genes have been identified, cloned, and characterized. The description also provides methods of using these genes and their encoded proteins. The description also provides specific, but not limiting, illustrative examples of embodiments of the present invention.

I. Regulation of Floral Development

It is now believed that at least four different but at least partially redundant pathways are involved in floral development. These pathways are photoperiodism, autonomous, gibberellin biosynthesis, and vernalization (see FIG. 1). Photoperiodism is the control of flowering based upon the quality and quantity of light. The autonomous pathway is the control of flowering in an environmentally autonomous manner that appears to act in parallel with the photoperiodic pathway to eventually initiate flowering even under unfavorable conditions. Giberellic acid also appears to induce flowering. Vernalization is the induction of flowering upon exposure of the plant to a sufficient period of cold. These pathways operate to different extents in different plants, and in some plants one or more of these pathways do not appear to operate at all.

These pathways have been best characterized in *Arabidopsis*, where numerous genes involved in the transition from vegetative growth to flowering have been identified (Simpson et al. (1999) Annu. Rev. Cell Dev. Biol; 99, 519-550). Almost all of these genes have been found through genetic screens for recessive mutations conferring delayed flowering; thus these genes presumably act to promote, rather than repress, flowering. These genes have traditionally been assigned into distinct groups based on the sensitivity of the mutant phenotype to environmental conditions, and these groups have formerly been considered to define three, partially redundant pathways (Martinez-Zapater et al. (1994) In *Arabidopsis*, ed. E. M. Meyerowitz and C. R. Sommerville. Cold Spring Harbor Laboratory Press, New York, pp. 403-434; and Coupland (1995) Trends Genet. 11, 393-397). Mutations in a subset of flowering-time genes predominately affect the photoperiodic control of flowering, such that the flowering habit of the corresponding mutant tends toward day-neutrality. Mutations in another subset of flowering-time genes result in delayed flowering without a significant loss of photopenodic sensitivity. In other words, these mutants flower later than wild-type plants under both photoperiodically inductive and noninductive conditions. Because mechanisms for sensing day length are evidently intact in the latter mutants, the corresponding genes are supposed to function in an environmentally 'autonomous' pathway that acts in parallel with the 'photoperiodic' pathway to eventually initiate flowering, even under unfavorable conditions (Martinez-Zapater et al. (1994) In *Arabidopsis*, ed. E. M. Meyerowitz and C. R. Sommerville. Cold Spring Harbor Laboratory Press, New York, pp. 403-434; Coupland (1995) Trends Genet. 11, 393-397; and Amasino (1996) Curr Opin Genet Dev. 1996 August; 6(4):480-7). Gibberellin (GA) biosynthesis defines a third pathway to flowering. Mutant plants defective in GA biosynthesis are unable to flower when grown in short days, and gibberellin-insensitive mutants flower extremely late under such conditions (Wilson et al. (1992) Plant Physiol. 100, 403-408). Another characteristic that has been used to distinguish among these groups is the promotive effect of cold (i.e. vernalization) in inductive photoperiods. The late flowering of mutants in the autonomous pathway and GA pathway can be annulled by cold, whereas cold is largely ineffective to accelerate flowering of the photoperiodic pathway mutants (Martinez-Zapater et al. (1994) In *Arabidopsis*, ed. E. M. Meyerowitz and C. R. Sommerville. Cold Spring Harbor Laboratory Press, New York, pp. 403-434).

In vernalization, flowering is not initiated until after an extended period of growth in the cold. In the natural environment, this mechanism allows flowering and seed production to occur only after winter. In the many ecotypes of *Arabidopsis thaliana* that exhibit this type of flowering habit, repression of flowering is mediated predominately through the activity of the FLOWERING LOCUS C (FLC) gene, which is a MADS-box gene (Koornneef et al. (1994) *Plant J.* 6, 911-919; Lee et al. (1994) *Plant J.* 6, 903-909); Michaels and Amasino (1999) *Plant Cell*, 11, 949-956; and Sheldon et al. (1999) *Plant Cell*, 11, 445-458). In current models of flowering, the repressive mechanism involving FLC acts antagonistically with promotive pathways associated with GA biosynthesis/sensitivity and perception of inductive photoperiods (Simpson et al. (1999) *Annu. Rev. Cell Dev. Biol.* 99, 519-550). The accelerated flowering of plants treated with Giberellic acids, or grown in inductive photoperiods, is not accompanied by greatly decreased FLC RNA expression (Sheldon et al. (1999) *Plant Cell*, 11, 445-458; and Michaels and Amasino (1999) *Plant Cell*, 11, 949-956), and FLC does not appear to be developmentally regulated (Sheldon et al. (1999) *Plant Cell*, 11, 445-458; and Rouse et al. (2002) *Plant J.* 29, 183-191), indicating that flowering pathways are integrated predominately 'downstream' of FLC (see FIG. 1). However, both genetic and molecular experiments have suggested that some 'crosstalk' occurs among pathways (Koornneef et al. (1998) *Genetics*, 148, 885-892); and Rouse et al. (2002) *Plant J.* 29, 183-191), and thus these flowering mechanisms cannot be proposed to act completely independently.

FLC is subject to both positive and negative regulation, and several flowering-time genes are known that act as strong, 'upstream' regulators of FLC. For example, genes in the so-called autonomous pathway, including LUMINIDEPENDENS (LD), FLOWERING LOCUS D (FLD), FPA, FVE, FY, and FCA, act to repress FLC (Koomneef et al (1991) *Mol. Gen. Genet.* 229, 57-66; and Koornneef et al. (1998) *Genetics*, 148, 885-892). This regulation occurs at least partly at the RNA level, as FLC RNA is expressed to high levels in autonomous-pathway mutants relative to wild-type plants (Michaels and Amasino (1999) *Plant Cell*, 11, 949-956; and Sheldon et al. (1999) *Plant Cell*, 11, 445-458). Several of the autonomous-pathway genes have now been characterized at the molecular level. LD encodes a nuclear protein containing a diverged homeodomain and an acidic carboxyl-terminal region enriched in glutamine residues (Lee et al. (1994) *Plant Cell* 6, 75-83; Aukerman and Amasino (1996) In *Seminars in Developmental Biology*, Vol. 7 (Amasino, R. M., ed). Cambridge: Academic Press, pp. 427-434; and van Nocker et al. (2000) *Plant Mol. Biol.* 44, 107-122) suggesting that it could act as a transcriptional regulator. Two other autonomous-pathway genes, FCA and FPA, encode proteins containing potential RNA-binding domains (Macknight et al. (1997) *Cell* 89, 737-745); and Schomburg et al. (2001) *Plant Cell*, 13, 1427-1436), suggesting that they function in posttranscriptional control of expression.

The FRIGIDA (FRI) gene also regulates FLC RNA expression, but, in contrast to the autonomous-pathway genes, acts in a promotive manner (Koornneef et al. (1998) *Plant Mol. Biol.* 49, 345-370; and Michaels and Amasino (1999) *Plant Cell*, 11, 949-956). The predicted FRI protein does not exhibit strong homology with any other protein of known function, but exhibits coiled-coil domains, suggesting that it interacts with protein partner(s) (Johanson et al. (2000) *Science*, 290, 344-347). Although it is now clear that other positive regulators of FLC exist (see below), only FRI has been characterized, because allelic variation at FRI is a major determinant of the flowering habit (i.e., annual vs. winter-annual) among natural *Arabidopsis* ecotypes (Lee et al. (1993) *Mol. Gen. Genet.* 237, 171-176; and Johanson et al. (2000) *Science*, 290, 344-347).

The mechanistic relationships among the autonomous-pathway genes, and between these genes and FRI, has not been well characterized. Evaluation of recent reports (Koornneef et al. (1998) *Genetics*, 148, 885-892; Rouse et al. (2002) *Plant J.* 29, 183-191; and Michaels and Amasino (2001) *Plant Cell*, 13, 935-941) suggests that FRI and autonomous-pathway genes likely act in flowering solely through mediation of FLC activity (see FIG. 1). The activation of FLC by FRI is epistatic to repression of FLC by autonomous-pathway genes (Michaels and Amasino (2000) *Plant Cell Environ.* 23, 1145-1153). This is consistent with a mechanism whereby FRI limits the activity of the autonomous pathway, possibly through the negative regulation of one or more components.

The flowering-promotive effect of cold, termed vernalization, is mediated largely through repression of inhibitory FLC activity. This also occurs at the RNA level (Michaels and Amasino (1999) *Plant Cell*, 11, 949-956; and Sheldon et al. (1999) *Plant Cell*, 11, 445-458), and probably at the transcriptional level, as cold is not sufficient to overcome the repression of flowering associated with constitutive expression of FLC in transgenic plants (Michaels and Amasino (1999) *Plant Cell*, 11, 949-956; and Sheldon et al. (1999) *Plant Cell*, 11, 445-458). The molecular process(es) involved in vernalization-associated downregulation of FLC is completely unknown. However, it is not likely to directly involve FRI or the autonomous-pathway genes; the evidence for this is that a long period of cold is fully effective to abrogate the late flowering phenotype of mutants lacking activities of both FRI and any of the known autonomous-pathway genes (Michaels and Amasino (2000) *Plant Cell Environ.* 23, 1145-1153). Although vernalization by nature should involve a temperature-sensitive mechanism, no molecular components of such a mechanism have been definitively identified. Moreover, although pathways of cold signaling in *Arabidopsis* are becoming increasingly well characterized, the involvement of known cold-signaling components in vernalization has generally not been explored. This is at least in part because most studies of cold signaling have been carried out in 'lab strains' of *Arabidopsis* [e.g., Columbia (Col), Landsberg erecta (Ler)]. These strains lack effective FRI and/or FLC alleles, and therefore do not exhibit strong FLC activity and typically flower soon after germination irrespective of cold (Koornneef et al. (1994) *Plant J.* 6, 911-919; Lee et al. (1994) *Plant J.* 6, 903-909; and Johanson et al. (2000) *Science*, 290, 344-347). The well-known CBF family of transcription factors, which act as molecular 'switches' to induce many elements of the cold acclimation response (Gilmour et al. (2000) *Plant Physiol.*, 124, 1845-1865), do not seem to be involved in vernalization. Constitutive expression of CBF1 or CBF3 in a late-flowering genetic background containing active FRI and FLC alleles, although sufficient to activate cold-responsive genes, did not greatly affect flowering time or FLC expression (Liu et al. (2002) *Physiol. Plant.* 114, 125-134); and observations of the inventors).

Once FLC is downregulated in vernalized plants, repression is maintained through an epigenetic mechanism involving the VERNALIZATION2 (VRN2) gene (Gendall et al. (2001) *Cell*, 107, 525-535). The cold-associated downregulation of FLC is not greatly affected by loss of VRN2 function, indicating that this gene probably is not important for initial suppression of FLC. VRN2 encodes a protein with sequence similarity to a member of the Polycomb-group protein class, which has been best characterized in *Drosophila*. These proteins are components of large complexes that reinforce the transcriptionally suppressed state of homeotic genes, potentially by packaging and/or maintaining chromatin in states less accessible to transcriptional machinery (Pirrotta (1997) *Curr. Opin. Genet. Dev.* 7, 249-258). Similarly, it is likely that VRN2 functions in some way to reduce accessibility of the FLC gene, as FLC chromatin in VRN2 mutants exhibits increased DNase sensitivity relative to that of wild-type plants, following cold treatment (Gendall et al. (2001) *Cell*, 107, 525-535). That chromatin structure is intimately involved in flowering and vernalization was previously shown by the strong effect on flowering conferred by disruption of processes tied to chromatin dynamics, including DNA methylation (Ronemus et al. (1996) *Science*, 273, 654-657; Finnegan et al (1996) *Proc. Natl Acad. Sci. USA*, 93, 8449-8454); and Finnegan (1998) *Proc. Natl Acad. Sci. USA*, 95, 5824-5829) and histone deacetylation (Tian and Chen (2001) *Proc. Natl Acad. Sci. USA*, 98, 200-205, especially in genotypes with a winter-annual flowering habit (Bum et al. (1993) *Proc. Natl Acad. Sci. USA*, 90, 287-291). Transgenic plants in which endogenous DNA methylation was disrupted exhibited decreased FLC expression in the absence of a vernalizing cold treatment (Sheldon et al. (1999) *Plant Cell*, 11, 445-458), indicating that appropriate chromatin structure is crucial for the maintenance of FLC expression in nonvernalized plants, as well as its suppression in vernalized plants.

II. Methods for Identifying Genes Involved in Vernalization

The present invention provides methods for identifying genes involved in vernalization. These methods include first screening a mutagenized population of plants (for example, *Arabidopsis* plants) for recessive mutants that exhibit a constitutively vernalized phenotype, or in other words mutants that flower early and independently of a cold treatment (in yet other words, without the requirement for vernalization), and that also exhibit decreased FLC RNA expression in the absence of cold. The plant population source of the mutants must possess an appropriate genetic background, in that wild type plants must require vernalization. Next, the expression of FLC in the mutants is evaluated, in order to screen out those early-flowering mutants identified in the first screen which are mutants of genes that are not involved in the regulation of FLC, such as genes that regulate flowering through photoperiodic and gibberellic acid (GA) pathways. Then genetic complementation analysis is performed in fri or flc mutants, to ensure that the remaining mutants are not mutants of the FRI or FLC genes. The mutants are grouped into loci based upon complementation analysis, and the loci mapped; preferably, mapping is based upon segregating F2 populations derived from a cross of the mutants to a winter-annual-habit parent. Identification of the genes is confirmed by expressing a wild-type gene in the mutant background, and restoring the requirement for vernalization. Additional evidence can be obtained by disrupting the identified gene by antisense technology, and/or by co-suppression technology.

A genetic screen was designed to identify positive regulators, or activators, of FLC (and thus negative regulators of vernalization) as a first step in the characterization of the mechanism of flowering repression involving FLC, and how this mechanism is negatively regulated by cold. The method included screening for recessive mutants that exhibit a vernalization independence, or constitutively vernalized, phenotype, or in other words mutants that flower early and independently of a cold treatment, and that also exhibit decreased FLC RNA expression in the absence of cold. Such mutants were presumed to represent genes that could regulate FLC either within or outside of the vernalization pathway.

As described above, ecotypes of *Arabidopsis* commonly studied in laboratories exhibit an annual, rather than winter-annual, flowering habit, and so are not an appropriate genetic background for this work. Instead, a synthetic "winter-annual" flowering *Arabidopsis* strain was utilized. This strain was developed by Lee and Amasino (1995) *Mol. Gen. Genet.* 237, 171-176), who synthesized a winter-annual-habit 'lab strain' by extensively introgressing the dominant, 'late' FRI allele from the winter-annual ecotype San Feliu-2 into the Columbia genetic background, which contains a 'late' allele of FLC. In this genotype (designated Col:FRI$^S$), a cold treatment of 30-40 days at 4 C. is able to fully eliminate the late-flowering phenotype. The use of the synthetic genetic background, containing an active FRI locus from a natural, winter-annual ecotype, introgressed into the Col genotype (Lee et al. (1994) *Plant J.* 6, 903-909), permits rigorous genetic analysis of FLC-associated repressive mechanism(s), while simultaneously permitting full utilization of currently available *Arabidopsis* genomics tools.

Two populations of mutagenized Col:FRI$^S$ plants were screened. The first population was mutagenized by fast-neutron radiation, using the fast-neutron beam at the MSU Cyclotron Laboratory. Fast neutron radiation is a highly desirable means of mutagenesis, as it typically induces small genomic deletions or rearrangements. These often result in strong alleles, and can greatly simplify and accelerate map-based cloning in genomic regions of known sequence. The fast-neutron mutagenized population comprised about 50,000 M1 individuals. The second population was mutagenized by T-DNA insertion ('T-DNA tagging'). Although a less efficient means of mutagenesis, T-DNA mutagenesis has the potential to greatly accelerate gene cloning by bypassing map-based cloning. A population of ~30,000 tagged lines in the Col:FRI$^S$ genetic background was generated using *Agrobacterium* infiltration. For this experiment, a T-DNA tagging vector constructed on a commonly used binary plasmid, pPZP200 (Hajdukiewicz et al. (1994) *Plant Mol. Biol.* 25, 989-994), and containing a BAR gene cassette conferring resistance to the herbicide glufosinate, was used. From combined screening of the fast-neutron and T-DNA mutagenized populations, 74 early-flowering mutants were identified.

The initial screen was expected to identify other classes of genes in addition to those specifically involved in regulation of FLC; such other classes of genes include those that regulate flowering through the photoperiodic and GA pathways. For example, because gibberellic acids can accelerate flowering of winter-annual *Arabidopsis*, mutations that disrupt gibberellic acid signaling would be expected to be identified in the screen (e.g., loss of function mutations in SPY, which normally acts to limit gibberellic acid signaling). In addition, early flowering conferred by ectopic expression of the CONSTANS gene, which is a predominate positive mediator of the photoperiod pathway, is largely epistatic to the winter-annual habit conferred by a mutation in FCA (Onouchi et al. (2000) *Plant Cell* 12, 885-900), suggesting that genes affecting photoperiodic flowering might also be identified in the screen. In order to distinguish among these classes of mutants, FLC expression was evaluated in the respective mutants. This was accomplished by measuring FLC RNA levels in wild-type Col:FRI plants and in the mutants. RNA was extracted from seedlings containing 2-3 primary leaves, and grown in either inductive or non-inductive photoperiods. For those plants grown under photoperiodically inductive conditions, vip mutants resulted in decreased to no expression of FLC RNA. This step eliminated most of the identified mutants from further consideration. Finally, to ensure that the lesions in the remaining mutants were not simply in the FRI or FLC genes, genetic complementation analysis was performed withfri or flc mutants. This further decreased the candidate mutant pool size to 14 mutants. Based on complementation analysis, these 14 mutants define at least seven loci. These loci were designated vernalization independence (vip) mutants.

For mapping, segregating F2 populations derived from a cross of the candidate mutants to a winter-annual-habit, recombinant-inbred line constructed in the Ler ecotype (obtained from R. Amasino) were used. This line, here designated Ler:FRI$^S$:FLC$^S$, consists of FRI$^S$ and the 'late' FLC locus from ecotype San Feliu-2 both introgressed into Ler through several successive backcrosses (Lee et al. (1994) *Plant J.* 6, 903-909). Mapping in a Col-Ler recombinant background is highly desirable, as most markers used for mapping in *Arabidopsis*, including the >50,000 polymorphisms identified by Cereon Genomics, are characterized in terms of Col and Ler alleles.

III. Vernalization Genes; Regulators of FLC

Several mutants have been identified by the methods described above for identifying genes involved in vernalization. This group of mutants is designated vernalization independence, as they exhibit a phenotype of flowering early and without the requirement for vernalization, or exposure to a sufficient period of cold, in a genetic background where the wild type phenotype requires vernalization to induce flowering. Several of these mutants have been further characterized. For example, two of these mutants, vip3 and vip4, the mutations are completely recessive, and both mutants exhibit a flowering time similar to vernalized wild-type plants in both inductive and noninductive photoperiods, and do not express FLC to detectable levels.

The genes identified by the vip mutants are designated VIP1-7, and are described in more detail below. The VIP3 nucleic acid sequences and encoded amino acid sequence are shown in FIGS. 3 and 4, respectively; the VIP4 nucleic acid sequences and encoded amino acid sequence are shown in FIGS. 5 and 6, respectively; the VIP5 nucleic acid sequences and encoded amino acid sequence are shown in FIGS. 12 and 13, respectively; and the VIP6 nucleic acid sequences and encoded amino acid sequences are shown in FIGS. 14 and 15, respectively.

VIP4

The VIP4 locus is represented in the screened populations by two T-DNA alleles and one fast neutron allele. FLC expression was not detectable in plants carrying the T-DNA allele vip4-1, indicating that VIP4 is a strong activator of FLC. However, VIP4 may also repress flowering outside of its positive regulation of FLC, as indicated by observations that vip4-1 plants flowered even earlier than flc plants when grown under noninductive (short day) photoperiods in the absence of cold.

Only slight defects in floral morphology are observed in growth or development of this mutant aside from flowering time. Among these is a widening of medial sepals, such that sepals typically fail to enclose the remainder of the floral bud in the latest stages of floral development. Petals are narrower than in wild-type flowers, and occasionally are greatly reduced in size. Stamens are often reduced in number to four or five. No defect in carpel morphology is apparent, and flowers are typically fully fertile.

Analysis of a segregating population derived from a cross between vip4-1 and wild-type Col:FRI$^S$ indicated that the T-DNA was both present at a single locus and linked to the early flowering phenotype. Genomic DNA adjacent to T-DNA was recovered through inverse PCR and identified by sequencing. Further analysis of the segregating population by PCR using both T-DNA-specific and gene-specific primers showed that the early-flowering phenotype segregated with homozygosity of the T-DNA in all of the 78 plants analyzed, indicating that the T-DNA tag was very closely linked to the mutation.

Based on current annotation of the genome, the T-DNA in vip4-1 has interrupted a gene near the bottom of chromosome V, which is in the transcribed region of a predicted gene At5g61150. The VIP4 gene (shown in FIG. 5) encodes a 633-residue, 72-kDa protein (shown in FIG. 6) with a predicted pI of 4.4. Almost one-half of the residues are charged (Glu, Asp, His, Lys, Arg) and thus the VIP4 protein is highly hydrophilic; this hydrophilicity is most apparent in extensive amino-terminal and carboxyl-terminal regions. The VIP4 protein does not exhibit any motif currently defined in the PROSITE Dictionary of Protein Sites and Patterns. However, predominately within its less hydrophilic central domain, VIP4 exhibits sequence homology with the Leo 1 protein from *S. cerevisiae*, and other hydrophilic proteins of unknown function from *S. pombe, C. elegans*, and *Drosophila* (23-29% identity over 239-311-amino acid segments).

Interestingly, preliminary results indicated that the abundance of VIP4 RNA decreases rapidly in response to cold exposure. In these experiments, RNA was isolated from wild-type seedlings that were 10 days old at the start of the cold treatment and analyzed by gel blotting; RNA was measured from CDR70, FLC, COR47, and 18S rDNA. These kinetics are in marked contrast to the very slow and gradual decrease in RNA expression of the FLC gene under the same conditions (see also Michaels and Amasino (1999) *Plant Cell* 11, 949-956). However, the levels of VIP4 RNA apparently increase upon return of cold-treated plants to warmer temperatures, as subsequent experiments in which VIP4 RNA expression in vernalized and nonvernalized seedlings was evaluated. In these experiments, VIP4 and FLC RNA expression was analyzed in various organs and tissues of wild-type plants, in nonvernalized and vernalized wild-type plants, and in various genetic backgrounds. RNAs were analyzed by gel blotting using CVN4 and FLC probes. Blots were subsequently stripped and reprobed with an 18S rDNA probe to indicate the integrity and relative quantity of total RNA in each lane. The results from analysis of expression in aerial portions of 14 d-old Columbia (Col), wild-type (Col:FRI$^{SF2}$), and ld-1 (Col:ld-1) seedlings grown without a cold treatment under short-day (SD) photoperiods, demonstrated that VIP4 RNA was expressed to similar levels irrespective of the vernalization status. The results also indicated that the effectiveness of the cold treatment given to these plants was evident by the decrease of FLC RNA to nondetectable levels. This suggests that VIP4 is necessary but not sufficient to activate FLC in vernalized plants, and that modulation of VIP4 RNA expression is unlikely to be involved in the vernalization response.

VIP3

Figure 2:
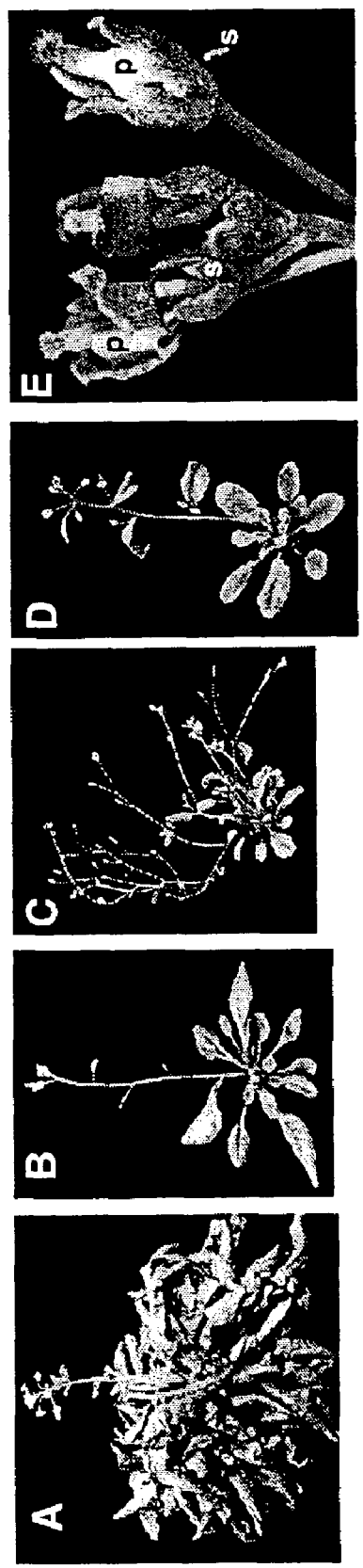
FIG. 2 shows Col:FRI genetic background and vip mutants. Panel A shows Col:FRI (vernalized, flowering after approximately 3 months); panel B shows Col:FRI (vernalized, flowering after approximately 3 weeks); panel C shows vip3 (not vernalized); panel C shows vip4 (not vernalized); and panel E shows a vip3 mutant inflorescence, with flowers showing reduced or filamentous sepals (s) and petals (p).

The VIP3 locus is represented in the screened populations by a single fast neutron allele. In addition to the defect in flowering time, vip3 plants exhibit several other defects in growth and development. These phenotypes cosegregated with early flowering in a mapping population of ~2000 recombinants, suggesting that they are all caused by the vip3 mutation. Specifically, vip3 plants are somewhat smaller than wild-type plants, and have reduced apical dominance (FIG. 2). In addition, flowers of vip3 plants exhibit abnormalities of organs in whorls 1-3 (FIG. 2). Lateral sepals are always reduced in size, and are often replaced by filamentous structures. Sepals typically have irregular, translucent margins. Petals and stamens are also reduced in size. Stamens are decreased in number to 4-5, and often are apparently replaced by filamentous structures. Flowers are usually completely male-sterile, but female-fertile.

Bulked segregant analysis was used to localize the vip3 mutation to a region of chromosome IV where no previous mutation affecting flowering time had been identified. VIP3 maps near EBS; based on the reported map position for EBS, the recombination data obtained in the study described here, and the current *Arabidopsis* Genome Initiative (AGI) genomic sequence, the distance separating vip3 from EBS is between about 1.5 mb and about 7 mb. Map-based cloning was then used with 480 early-flowering individuals from the mapping population to localize the mutation within a about 0.25 mb region represented by three BAC (bacterial artificial chromosome) clones. Subsequently, vip3 DNA was compared to wild-type genomic DNA using gel-blot analysis and these three BACs as probes. This approach resulted in the indication of a deletion of about 2 kb within BAC F27B13, and this was confirmed by sequencing PCR products amplified from the region. Based upon current annotation of the genome provided by the AGI, this deletion would span a major portion of the transcribed region of a gene designated F27B13.70, and extend to within about 1 kb of the transcriptional start site of a gene designated F27B13.80. Wild-type plants and vip3 mutants were analyzed by RNA gel-blots. RNA was isolated from approximately 10 day old seedlings. Blots were probed with PCR products encompassing the entire transcribed regions of gene F27B13.70 or F27B13.80 as predicted by current genomic annotation. The results indicated that RNA expression of F27B13.70 was abolished in vip3, and also that there was no apparent effect on expression of F27B13.80. To confirm that F27B13.70 was VIP3, transgenic plants in which F27B13.70 was suppressed by antisense RNA expression were engineered. In a number of these transgenic plants, the multiple vip3 phenotypes were recreated.

Based upon AGI annotation, VIP3 gene (as shown in FIG. 4) encodes a 321-amino acid protein (as shown in FIG. 5) that is composed almost entirely of seven repeats of a motif designated the Trp-Asp (WD) motif (also known as the WD-40 repeat; Neer et al. (1994) *Nature* 371, 297-300; and Smith et al. (1999) Trends Biochem Sci 24, 181-185). The predicted VIP3 protein does not show extensive sequence homology with any protein cataloged in current protein databases. However, several known and predicted proteins exhibit an overall structure similar to VIP3, with seven tandem WD repeats and no extensive amino-terminal or carboxyl-terminal extensions. These include the Gβ subunit of heterotrimeric GTP-binding proteins. VIP3 cDNAs from a vegetative-apex cDNA library were isolated and sequenced to confirm the intron-exon structure predicted by the AGI. Recombinant VIP3 protein has been expressed in *E. coli*, and the purified the recombinant protein has been purified to apparent homogeneity in preparation for antisera production.

Other VIP Genes

In addition to VIP4 and VIP3, mutations at five other loci result in phenotypes that are superficially indistinguishable from vip4 and vip3. Although two of the VIP loci, VIP2 and VIP5, map roughly to the previously identified flowering-time gene EFS, the vip2 and vip5 mutants do not exhibit specific pleiotropic phenotypes described for efs mutants. In addition, the specific floral defects seen in the vip mutants were not reported in efs mutants (Soppe et al. (1999) Development 126: 4763-4770). Thus, the VIP loci define a previously unreported group of flowering repressors.

Additional VIP genes have been identified, using the methods described above, and in particular in the Examples. For example, genes VIP5 and VIP6 have also been cloned. Because the mapped position of VIP5 corresponded to the location of the Rtf1 homolog At1g61040, this gene was sequenced from the vip5 mutant and found to have an insertion-deletion mutation that would terminate the reading frame after amino acid 319 of the predicted 643-amino acid protein. The entire VIP5 gene was cloned; the genomic nucleotide sequence of a VIP5 gene obtained from the AGI database is shown in FIG. 12A (SEQ ID NO:7). The cDNA was also cloned and sequenced; this sequence, shown in FIG. 12B (SEQ ID NO:9), agrees with the sequence predicted in the AGI database. The VIP5 amino acid sequence predicted from the cloned cDNA sequence is shown in FIG. 13 (SEQ ID NO:13).

Likewise, VIP6 was mapped to a <1 mb region containing the Ctr9 homolog At2g06210. Using PCR and sequencing, the presence of a T-DNA within the 5' UTR for this gene in vip6-3 was confirmed, and the entire gene region was determined to deleted in vip6-1. The entire VIP6 gene was also cloned; the genomic nucleotide sequence of a VIP5 gene obtained from the AGI database is shown in FIG. 12A (SEQ ID NO:7). However, the intron/exon structure for At2g06210 (VIP6) as depicted by the *Arabidopsis* Genome Initiative (AGI) is incorrect (cDNA sequence shown in FIG. 14D, SEQ ID NO:12), as is the prediction by NCBI; the protein predicted by NCBI is longer than the protein predicted by the cloned cDNA. This was determined by isolating and sequencing VIP6 cDNA. Two forms of cDNA are expressed: a short form, and a long form, as shown in FIG. 14, Panels B and C (SEQ ID NOs: 10 and 11, respectively). The VIP6 gene also produces at least two distinct proteins, as predicted from the two different cDNA sequences; these amino acid sequences are shown in FIG. 15, Panels A and B (SEQ ID NOs: 14 and 15); the amino acid sequence predicted by the AGI database is shown in FIG. 15C (SEQ ID NO:16). The short form and long form cDNA sequences differ by only about 50 base pairs; however, the protein encoded by the short form cDNA is longer than the protein encoded by the long form cDNA, due to the presence of an intron in the long form cDNA resulting the appearance of a stop codon which results in a shorter protein.

The cloning of VIP5 and VIP6 is confirmed through molecular complementation, as for example is described in the Examples. Moreover, the discovery of additional alleles for vip5 and vip6, provides additional confirmation that the VIP5 and VIP6 genes have been correctly identified and cloned.

As in the mutants vip3 and vip4, the flower morphology in mutants vip5 and vip6 is disrupted, and the flowers tend to be male sterile. Thus, the vip mutants result in early-flowering phenotype, and display similar defects in floral development.

Roles of VIP Genes.

The genetic and molecular analyses of the VIP genes demonstrate that these genes affect both floral timing and floral development. Both VIP4 and VIP3 appear to act as a repressor of flowering at least partly through their ability to strongly activate FLC. Current knowledge of flowering is consistent with FLC being regulated predominately through at least two mechanisms or pathways (Michaels and Amasino (1999) *Plant Cell* 11, 949-956). One mechanism involves the autonomous-pathway genes, which repress FLC expression, and FRI, which acts antagonistically to the autonomous pathway (Simpson et al. (1999) *Annu. Rev. Cell Dev. Biol.* 99, 519-550), possibly by limiting the activity of one or more components. At least a second mechanism must be proposed to promote FLC expression, based on the observation that, in plants lacking activity of the autonomous pathway, FLC is strongly expressed even in the absence of FRI. Because FLC expression is repressed by cold even in the absence of FRI and/or autonomous pathway function, vernalization is postulated to limit the activity of this second mechanism.

Although it is not necessary to understand the underlying mechanism to practice the invention, and it is not intended that the invention be limited to any particular hypothesis or theory, VIP4 is contemplated to occupy any of a number of positions and functions with respect to these pathways. VIP4 RNA levels were not affected by loss of function of FRI or LD, indicating that, if VIP4 mediates activation of FLC by FRI and/or derepression of FLC by loss of autonomous pathway activity, such a mechanism would have to involve changes in CVN4 protein activity, or changes in RNA levels within restricted tissues. The observation that vip4 mutants flower much earlier than fri null mutants also suggests that VIP4 does not act in flowering exclusively with FRI as a co-activator of FLC. Thus, it is thought that VIP4 acts independently of these genes in a distinct mechanism required for FLC expression in the absence of cold. It was observed that increasing VIP4 RNA expression was not sufficient to further activate FLC, even in nonvernalized plants where other elements necessary for FLC expression are active.

Also vip4 mutations appear to be completely recessive. The lack of gene dosage effect is consistent with VIP4 acting as one, nonlimiting component of a more extensive mechanism. Obvious candidates for other potential components are represented by the several allelic groups of vip mutations identified through the genetic screening methods described above.

A flowering-repressive mechanism involving VIP4 could function in several possible capacities. For example, because the 'vernalized state' is not maintained through meiosis (i.e., the requirement for cold is re-set in each generation; Lang (1965) In *Encyclopedia of Plant Physiology*, (Ruhland, W., ed). Berlin: Springer-Verlag, pp. 1371-1536), this mechanism could act to re-establish FLC expression in the developing embryo, possibly by disrupting the epigenetic repressive mechanism involving VRN2. Another possibility is that VIP4 acts in a hypothetical pathway of vernalization cold signaling, maintaining it in an 'off' state. However, if this is the case, then VIP4 is unlikely to act as a general suppressor of cold-signaling pathways, a role hypothesized for the HOS1 gene (Lee et al. (2001) *Genes Dev.* 15, 912-924), because unlike hos1 mutants, vip4 plants exhibited neither ectopic expression of a representative cold-responsive gene, COR78, nor enhanced freezing tolerance as measured by electrolyte leakage assays.

Irrespective of its nature, the flowering-repressive mechanism involving VIP4 could be deactivated by cold through the negative regulation of one or more components. The observation that VIP4 RNA is expressed to equivalent levels in both nonvernalized and vernalized plants suggests that if VIP4 itself were a cold-regulated component, regulation would either be mediated at the level of VIP4 protein activity, or at the RNA level within a restricted subset of tissues. However, in this respect, it is noteworthy that the subtle floral defects seen in plants lacking VIP4 activity are not observed in vernalized, wild-type plants, suggesting that VIP4 maintains activity in vernalized plants, at least in floral tissues.

The VIP4 protein exhibits sequence homology with yeast Leo1 and proteins from *Drosophila* and *C. elegans*; in addition, the highly hydrophilic nature of these proteins is conserved. These observations suggest that these proteins could function in analogous molecular mechanisms. Of these proteins, only Leo 1 has been characterized. This protein has been shown to exhibit an ATP-sensitive interaction with the 19S 'cap' of the proteasome (Verma et al. (2001) *Mol. Biol. Cell*, 11, 3425-3439), and high-throughput, proteomic analyses suggest that Leo 1 physically interacts with multiple protein partners in several cellular contexts, including transcription (Ito et al. (2001) *Proc. Natl. Acad. Sci. USA*, 98, 4569-4574; and Gavin et al. (2002) *Nature*, 415, 141-147). It is noteworthy that the defects in floral morphology seen in vip4 mutants are not observed in mutants or natural ecotypes lacking FLC activity (Michaels and Amasino (1999) *Plant Cell*, 11, 949-956), suggesting that the role of VIP4 in floral development is mediated outside of its relationship with FLC. Thus, it is contemplated that VIP4 acts as a common component of distinct developmental mechanisms, possibly through interactions with multiple protein partners.

The observation that vip4 mutants flower earlier than fc null mutants indicates that VIP4 regulates flowering-time genes in addition to FLC. These hypothetical target(s) could have a role in GA biosynthesis or sensitivity, or in the perception of photoperiod, as current models of flowering predict that such mechanisms would influence flowering outside of pathway(s) involving FLC (Simpson et al. (1999) *Annu. Rev. Cell Dev. Biol.* 99, 519-550). An especially attractive candidate is FLM (also known as AGL27 (Alvarez-Buylla et al. (2000) *Plant J.* 24, 457-466) or MAF1 (Ratcliffe et al. (2001) *Plant Physiol.* 126, 122-132), which encodes a MADS-box protein highly related to FLC, and which acts as a floral repressor through a mechanism that is likely independent of FLC (Scortecci et al. (2001) *Plant J.* 26, 229-236; and Ratcliffe et al. (2001) *Plant Physiol.* 126, 122-132). Other possibilities include AGL31, a tandemly repeated cluster of four genes which also encode proteins highly related to FLC (Alvarez-Buylla et al. (2000) *Plant J.* 24, 457-466; and Scortecci et al. (2001) *Plant J.* 26, 229-236).

The VIP3 gene also encodes a regulator of the vernalization response acting primarily through activation of the floral repressor FLC. In addition to its early-flowering phenotype, the vip3 mutant displays defects in floral development. Because plants lacking FLC do not display floral defects, the role of VIP3 in floral development is mediated outside of its regulation of FLC. The overall whorl structure of vip3 mutant flowers does not seem to be disrupted, indicating that the basic defect of vip3 flowers is not in patterning, but in floral organ identity and/or development. Of the many mutants conferring defects in floral organ identity or development that have been described, vip3 most closely resembles mutants with a defect in the CLF, EBS, or ICU2 genes. In clf-2 mutants, for example, sepals fail to enclose floral buds, petals are small and narrow, and homeotic transformation of sepals to carpels, and of petals to stamens, are sometimes observed (Goodrich et al., (1997) *Nature* 386, 44-51). The phenotype of ebs and icu2 flowers is similar to that of clf-2, but homeosis is not seen (Gómez-Mena et al., (2001) *Plant Cell* 13, 1011-1024; Serrano-Cartagena et al., (2000) *Genetics* 156, 1363-1377). CLF, EBS, ICU2, and VIP3 map to different genomic positions, and therefore are not the same gene. Rather, it is contemplated that they represent a class of gene with related function. This is supported by the expression of AG RNA in vip3 flowers, which was elevated approximately 50% over wild-type flowers; however, it was not clear whether this effect was a direct result of lack of VIP3 activity, or rather, an indirect effect of the relative overabundance of carpet tissues in vip3 flowers, where AG is normally expressed. AG is not expressed to detectable levels in the leaves of vip3, indicating that any regulation of AG by vip3 is probably restricted to the flower. This is consistent with the observation that leaves of vip3 mutants do not display the curly phenotype seen in clf and icu2 mutants, which is associated with ectopic expression of AG in the leaves.

VIP3 encodes a protein containing WD motifs. The WD motif is found in a large variety of proteins that do not share any obvious function (Neer et al., (1994) *Nature* 371, 297-300). However, where characterized in other proteins, WD motifs participate in protein-protein interactions (e.g., *Arabidopsis* COP1-HY5; Torii et al., (1998) *EMBO J.* 17, 5577-5587). A query of proteins presently cataloged in databases indicates that the amino acid sequence of VIP3 is most closely related to that of the Gβ WD-repeat proteins; however, the sequence homology is low (30-35% identity) and is confined to the most conserved elements of the WD repeats. The crystal structure of Gβ shows that in this protein, each WD motif unit takes the form of four, antiparallel β strands, with the seven repeated WD motifs forming a symmetrical structure termed a β propeller. A distinctive feature of the VIP3 protein is a 13-residue extension between predicted strands D and A of repeat IV. The analogous region of Gβ takes the form of a loop comprising the top surface of the of the propeller structure, and additional amino acids may comprise an independently folded domain that would protrude from the top of the structure. VIP3 appears to lack extensive amino- or carboxyl-terminal domains outside of the β propeller, suggesting that it acts exclusively in the context of a molecular scaffold. Although it is not necessary to understand the underlying mechanism to practice the invention, and it is not intended that the invention be limited to any particular hypothesis or theory, VIP3 is contemplated to be a component of a multisubunit protein. Consistent with this, mutations at five other loci create phenotypes that are essentially indistinguishable from that of vip3, and these define functionally similar genes that could be additional members of such a complex.

Vernalization has been described as an epigenetic phenomenon, possible involving the cold-associated modification of chromatin structure associated with changes in DNA methylation. Thus, VIP3 and other activators of FLC might function as components of chromatin remodeling complexes, functioning specifically to maintain the FLC genomic region in a configuration accessible to transcriptional machinery. Cold might act to repress the activity of one or more of these components. VIP3 RNA expression is not modulated by cold or in response to vernalization, suggesting that other components carry out this role.

Although it is not necessary to understand the underlying mechanism to practice the invention, and it is not intended that the invention be limited to any particular hypothesis or theory, it is contemplated that the VIP genes define components of a protein complex, potentially analogous to the yeast Paf1 transcriptional complex. As noted above, VIP4 encodes a highly hydrophilic protein with similarity to the Leo1 protein. Leo1 is involved in the expression of a small subset of yeast genes, as a component of the Paf1 transcriptional regulator, which may represent a transcriptional endpoint of protein kinase C-mitogen-activated protein kinase signaling (Mueller and Jaehning (2002) Mol Cell. Biol. 22: 1971-1980). The cloning of VIP5 and VIP6 indicate that the encoded proteins are *Arabidopsis* homologs of additional subunits of the yeast Paf1 protein. The yeast counterpart of VIP4, Leo1, specifically interacts with Paf1 subunits Rtf1 and Ctr9 (Gavin et al. 2002; Mueller and Jaehning, 2002). However, at least VIP3 does not exhibit strong homology with known Paf1 components or any other yeast proteins. It is further contemplated that the VIP gene class defines a mechanism involved in multiple developmental processes, including flowering (through the activation of FLC) and floral development (through interaction with other factors).

IV. Vernalization Genes, Coding Sequences and Polypeptides

A. Nucleic Acid Sequences

1. *Arabidopsis* VIP Genes.

The present invention provides plant VIP genes and encoded proteins. The designation "VIP" refers to the phenotype exhibited by plants with a mutation in a VIP gene, where the mutant is vernalization independence (also referred to as constitutively vernalized; these two terms may be used interchangeably. Thus, a CVN gene refers to a constitutively vernalized gene, which is a VIP gene.) A vernalization independence (or constitutively vernalized) phenotype is flowering early without the requirement for vernalization, or exposure to a sufficient period of cold, in a genetic background where the wild type phenotype requires vernalization to induce flowering, and exhibiting decreased FLC RNA expression in the absence of cold. A VIP gene is not an FLC (FLOWERING LOCUS) gene or an FRI (FRIGIDA) gene. It is contemplated that the function of a VIP gene is carried out by the encoded protein product of the VIP gene.

In some embodiments of the present invention, isolated nucleic acid sequences comprising VIP genes are provided; mutations in these genes, which disrupt expression of the genes, result in a vernalization independence (or constitutively vernalized) phenotype. In particular embodiments, isolated nucleic acid sequences comprising VIP3, VIP4, VIP5, or VIP6 are provided. These sequences include sequences comprising VIP genomic sequences (for example, as shown in FIGS. 3, 5, 12A or 14A, respectively; SEQ ID NOs: 1, 2,7, or 8, respectively) and VIP cDNA sequences (for example, as shown in FIGS. 3, 5, 12B, or 14B-C, respectively, as the underlined portions SEQ ID NOs: 3 or 4 for VIP3 or VIP4, or SEQ ID NOs: 9 and 10-12 for VIP5 and VIP6).

2. Additional VIP Genes.

The present invention provides nucleic acid sequences comprising additional CVN genes. For example, some embodiments of the present invention provide polynucleotide sequences that are homologous to at least one of SEQ ID NOs: 1-4 and 7-12 identified by searching available plant genomic databases. Other embodiments of the present invention provide sequences capable of hybridizing to at least one of SEQ ID NOs: 1-4 and 7-12 under conditions of low to high stringency, as long as the polynucleotide sequence capable of hybridizing to at least one of SEQ ID NOs:1-4 and 7-12 encodes a protein that retains a desired biological activity of a VIP protein; in some preferred embodiments, the hybridization conditions are high stringency. In preferred embodiments, hybridization conditions are based on the melting temperature ($T_m$) of the nucleic acid binding complex and confer a defined "stringency" as explained above (See e.g., Wahl et al., Meth. Enzymol., 152:399-407 [1987], incorporated herein by reference).

In other embodiments of the present invention, alleles of VIP genes, and in particular of VIP3, VIP4, VIP5, and VIP6 genes, are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions, or substitutions of nucleic acids. Each of these types of changes may occur alone, or in combination with the others, and at the rate of one or more times in a given sequence.

In other embodiments of the present invention, the polynucleotide sequence encoding a VIP gene is extended utilizing the nucleotide sequences (e.g., SEQ ID NOs:1 or 2 or 7 or 8) in various methods known in the art to detect upstream sequences such as promoters and regulatory elements. For example, it is contemplated that for VIP3, VIP4, VIP5, or VIP6, the sequences upstream are identified from the *Arabidopsis* genomic database. For other VIP genes for which a database is available, the sequences upstream of the identified VIP genes can also be identified. For other VIP genes for which a public genomic database is not available, or not complete, it is contemplated that polymerase chain reaction (PCR) finds use in the present invention.

In another embodiment, inverse PCR is used to amplify or extend sequences using divergent primers based on a known region (Triglia et al., Nucleic Acids Res., 16:8186 [1988]). In yet another embodiment of the present invention, capture PCR (Lagerstrom et al., PCR Methods Applic., 1:111-19 [1991]) is used. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, [1995]; Lui et al., [1995])

Preferred libraries for screening for full length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

3. Variant VIP Genes.

In some embodiments, the present invention provides isolated variants of the disclosed nucleic acid sequence encoding CVN genes, and in particular of VIP3, VIP4, VIP5, or VIP6 genes, and the polypeptides encoded thereby; these variants include mutants, fragments, fusion proteins or functional equivalents of VIP gene protein products. Thus, nucleotide sequences of the present invention are engineered in order to alter a VIP coding sequence for a variety of reasons, including but not limited to alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability).

a. Mutants. Some embodiments of the present invention provide nucleic acid sequences encoding mutant forms of VIP proteins, and in particular of VIP3, VIP4, VIP5, or VIP6 proteins, (i.e., muteins), and the polypeptides encoded thereby. In preferred embodiments, muteins result from mutation of the coding sequence, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

Mutants of VIP genes can be generated by any suitable method well known in the art, including but not limited to site-directed mutagenesis, randomized "point" mutagenesis, and domain-swap mutagenesis in which portions of the VIP cDNA are "swapped" with the analogous portion of other VIP-encoding cDNAs (Back and Chappell, PNAS 93: 6841-6845, [1996]).

It is contemplated that is possible to modify the structure of a peptide having an activity (e.g., such as a VIP activity, which is the absence of the naturally occurring protein in a plant which results in the phenotype of constitutive vernalization, where the wild type phenotype requires vernalization to flower), for such purposes as increasing synthetic activity or altering the affinity of the VIP protein for a binding partner or a kinetic activity. Such modified peptides are considered functional equivalents of peptides having an activity of a VIP activity as defined herein. A modified peptide can be produced in which the nucleotide sequence encoding the polypeptide has been altered, such as by substitution, deletion, or addition. In some preferred embodiments of the present invention, the alteration increases or decreases the effectiveness of the VIP gene product to exhibit a vernalized phenotype in a plant where the wild type requires vernalization to flower. In other words, construct "X" can be evaluated in order to determine whether it is a member of the genus of modified or variant VIP genes of the present invention as defined functionally, rather than structurally. Accordingly, in some embodiments the present invention provides nucleic acids comprising a VIP sequence that complement the coding regions of any of SEQ ID NOs: 1-4, as well as the proteins encoded by such nucleic acids.

Moreover, as described above, mutant forms of VIP proteins are also contemplated as being equivalent to those peptides that are modified as set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide nucleic acids comprising sequences encoding variants of VIP gene products disclosed herein containing conservative replacements, as well as the proteins encoded by such nucleic acids. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a mutant includes "nonconservative" changes (e.g., replacement of a glycine with a tryptophan).

Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.). Accordingly, other embodiments of the present invention provide nucleic acids comprising sequences encoding variants of VIP gene products disclosed herein containing non-conservative replacements where the biological activity of the encoded protein is retained, as well as the proteins encoded by such nucleic acids.

b. Directed Evolution. Variants of VIP genes or coding sequences may be produced by methods such as directed evolution or other techniques for producing combinatorial libraries of variants. Thus, the present invention further contemplates a method of generating sets of nucleic acids which encode combinatorial mutants of the VIP proteins, as well as truncation mutants, and is especially useful for identifying potential variant sequences (i.e., homologs) that possess the biological activity of the encoded VIP proteins. In addition, screening such combinatorial libraries is used to generate, for example, novel encoded VIP gene product homologs that possess novel binding or other kinetic specificities or other biological activities all together. The invention further provides sets of nucleic acids generated as described above, where a set of nucleic acids encodes combinatorial mutants of the VIP proteins, or truncation mutants, as well as sets of the encoded proteins. The invention further provides any subset of such nucleic acids or proteins, where the subsets comprise at least two nucleic acids or at least two proteins.

It is contemplated that the VIP, and in particular VIP3, VIP4, VIP5, or VIP6, genes and coding sequences (e.g., any one or more of SEQ ID NOs: 1-4, and 7-8 and fragments and variants thereof) can be utilized as starting nucleic acids for directed evolution. These techniques can be utilized to develop encoded VIP product variants having desirable properties such as increased kinetic activity or altered binding affinity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., screened for restoring vernalization in a constitutively vernalized mutant, in a wild type background where vernalization is required, as described above and below). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324-25 [1994]; U.S. Pat. Nos. 5,837,458; 5,830,721; 5,811, 238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination.

c. Homologs. Still other embodiments of the present invention provide isolated nucleic acid sequences encoding VIP genes, and in particular at least one of VIP3, VIP4, VIP5, or VIP6 genes, homologs, and the polypeptides encoded thereby. Some homologs of encoded VIP products have intracellular half-lives dramatically different than the corresponding wild-type protein. For example, the altered protein is rendered either more stable or less stable to proteolytic degradation or other cellular process that result in destruction of, or otherwise inactivate the encoded VIP product. Such homologs, and the genes that encode them, can be utilized to alter the activity of the encoded VIP products by modulating the half-life of the protein. For instance, a short half-life can give rise to more transient VIP biological effects. Other homologs have characteristics which are either similar to wild-type VIP, or which differ in one or more respects from wild-type VIP.

In some embodiments of the combinatorial mutagenesis approach of the present invention, the amino acid sequences for a population of VIP gene product homologs are aligned, preferably to promote the highest homology possible. Such a population of variants can include, for example, VIP gene homologs from one or more species, or VIP gene homologs from the same species but which differ due to mutation. Amino acids that appear at each position of the aligned sequences are selected to create a degenerate set of combinatorial sequences.

In a preferred embodiment of the present invention, the combinatorial VIP gene library is produced by way of a degenerate library of genes encoding a library of polypeptides that each include at least a portion of candidate encoded VIP-protein sequences. For example, a mixture of synthetic oligonucleotides is enzymatically ligated into gene sequences such that the degenerate set of candidate VIP sequences are expressible as individual polypeptides, or alternatively, as a set of larger fusion proteins (e.g., for phage display) containing the set of VIP sequences therein.

There are many ways by which the library of potential VIP homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential VIP sequences. The synthesis of degenerate oligonucleotides is well known in the art (See e.g., Narang, Tetrahedron 39:3-22 [1983]; Itakura et al., Recombinant DNA, in Walton (ed.), Proceedings of the 3rd Cleveland Symposium on Macromolecules, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science, 249:386-390 [1980]; Roberts et al., Proc. Nati. Acad. Sci. USA, 89:2429-2433 [1992]; Devlin et al., Science, 249: 404-406 [1990]; Cwirla et al., Proc. Natl. Acad. Sci. USA, 87: 6378-63 82 [1990]; as well as U.S. Pat. Nos. 5,223,409, 5,198,346, and 5,096,815; all of which are incorporated herein by reference).

d. Screening Gene Products. A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of VIP homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in some embodiments of the present invention, the gene library is cloned into the gene for a surface membrane protein of a bacterial cell, and the resulting fusion protein detected by panning (WO 88/06630, herein incorporated by reference; Fuchs et al., BioTechnol., 9:1369-72 [1991]; and Goward et al., TIBS 18:136-140 [1992]). In other embodiments of the present invention, fluorescently labeled molecules that bind encoded VIP products can be used to score for potentially functional VIP homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007-16010 [1992]; Griffths et al., EMBO J., 12:725-734 [1993]; Clackson et al., Nature, 352:624-628 [1991]; and Barbas et al., Proc. Natl. Acad. Sci., 89:4457-4461 [1992]).

In another embodiment of the present invention, the recombinant phage antibody system (e.g., RPAS, Pharmacia Catalog number 27-9400-01) is modified for use in expressing and screening of encoded VIP product combinatorial libraries. The pCANTAB 5 phagemid of the RPAS kit contains the gene that encodes the phage gIII coat protein. In some embodiments of the present invention, the VIP combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate VIP gene insert. The resulting recombinant phage contain phagemid DNA encoding a specific candidate VIP protein and display one or more copies of the corresponding fusion coat protein. In some embodiments of the present invention, the phage-displayed candidate proteins that display any property characteristic of a VIP protein are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning will greatly enrich for VIP homologs.

In light of the present disclosure, other forms of mutagenesis generally applicable will be apparent to those skilled in the art in addition to the aforementioned rational mutagenesis based on conserved versus non-conserved residues. For example, VIP homologs can be generated and screened using, for example, alanine scanning mutagenesis and the like (Rufet al., Biochem., 33:1565-1572 [1994]; Wang et al., J. Biol. Chem., 269:3095-3099 [1994]; Balint Gene 137: 109-118 [1993]; Grodberg et al., Eur. J. Biochem., 218:597-601 [1993]; Nagashima et al., J. Biol. Chem., 268:2888-2892 [1993]; Lowman et al., Biochem., 30:10832-10838 [1991]; and Cunningham et al., Science, 244:1081-1085 [1989]), by linker scanning mutagenesis (Gustin et al., Virol., 193:653-660 [1993]; Brown et al., Mol. Cell. Biol., 12:2644-2652 [1992]; McKnight et al., Science, (1982) Science. 217:316), or by saturation mutagenesis (Meyers et al., Science, 232:613 [1986]).

e. Truncation Mutants of VIiP. In addition, the present invention provides isolated nucleic acid sequences encoding fragments of encoded VIIP products (i.e., truncation mutants), and the polypeptides encoded by such nucleic acid sequences. In preferred embodiments, the VIiP fragment is biologically active. In some embodiments of the present invention, when expression of a portion of a VW protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751-757 [1987]) and Salmonella typhimurium and its in vitro activity has been demonstrated on recombinant proteins (Miller et al., Proc. NatI. Acad. Sci. USA, 84:2718-2722 [1987]). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

f. Fusion Proteins Containing VIP. The present invention also provides nucleic acid sequences encoding fusion proteins incorporating all or part of VIP, and the polypeptides encoded by such nucleic acid sequences. In some embodiments, the fusion proteins have a VIP functional domain with a fusion partner. Accordingly, in some embodiments of the present invention, the coding sequences for the polypeptide (e.g., a VIP functional domain) is incorporated as a part of a fusion gene including a nucleotide sequence encoding a different polypeptide. It is contemplated that such a single fusion product polypeptide is able to remove a constitutively vernalized phenotype in a wild type plant which normally requires vernalization for flowering, such that the transgenic plant again requires vernalization for flowering.

In some embodiments of the present invention, chimeric constructs code for fusion proteins containing a portion of a VIP protein and a portion of another gene. In some embodiments, the fusion proteins have biological activity similar to the wild type VIP (e.g., have at least one desired biological activity of a VIP protein). In other embodiments, the fusion protein have altered biological activity.

In addition to utilizing fusion proteins to alter biological activity, it is widely appreciated that fusion proteins can also facilitate the expression and/or purification of proteins, such as the VIP protein of the present invention. Accordingly, in some embodiments of the present invention, a VIP protein is generated as a glutathione-S-transferase (i.e., GST fusion protein). It is contemplated that such GST fusion proteins enables easy purification of the VIP protein, such as by the use of glutathione-derivatized matrices (See e.g., Ausabel et al. (eds.), Current Protocols in Molecular Biology, John Wiley & Sons, N.Y. [1991]).

In another embodiment of the present invention, a fusion gene coding for a purification leader sequence, such as a poly-(His)/enterokinase cleavage site sequence at the N-terminus of the desired portion of a VIP protein allows purification of the expressed VIP fusion protein by affinity chromatography using a $Ni^{2+}$ metal resin. In still another embodiment of the present invention, the purification leader sequence is then subsequently removed by treatment with enterokinase (See e.g., Hochuli et al., J. Chromatogr., 411:177 [1987]; and Janknecht et al., Proc. Natl. Acad. Sci. USA, 88:8972). In yet other embodiments of the present invention, a fusion gene coding for a purification sequence appended to either the N or the C terminus allows for affinity purification; one example is addition of a hexahistidine tag to the carboxy terminus of a VIP protein which is optimal for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra).

B. Encoded VIP Gene Polypeptides

The present invention provides isolated VIP polypeptides, as well as variants, homologs, mutants or fusion proteins thereof, as described above. In some embodiments of the present invention, the polypeptide is a naturally purified product, while in other embodiments it is a product of chemical synthetic procedures, and in still other embodiments it is produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention is glycosylated or non-glycosylated. In other embodiments, the polypeptides of the invention also includes an initial methionine amino acid residue.

1. Purification of VIP Polypeptides

The present invention provides purified VIP polypeptides as well as variants, homologs, mutants or fusion proteins thereof, as described above. In some embodiments of the present invention, VIP polypeptides purified from recombinant organisms as described below are provided. In other embodiments, VIP polypeptides purified from recombinant bacterial extracts transformed with *Arabidopsis* VIP cDNA, and in particular any one or more of VIP3, VIP4, VIP5, or VIP6 cDNA, are provided (as described in the Examples).

The present invention also provides methods for recovering and purifying VIP from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

The present invention further provides nucleic acid sequences having the coding sequence for a VIP protein (e.g., SEQ ID NOs: 1-4 or 7-10) fused in frame to a marker sequence that allows for expression alone or for both expression and purification of the polypeptide of the present invention. A non-limiting example of a marker sequence is a hexahistidine tag that is supplied by a vector, for example, a pQE-30 vector which adds a hexahistidine tag to the N terminal of a VIP gene and which results in expression of the polypeptide in a bacterial host, or, for example, the marker sequence is a hemagglutinin (HA) tag when a mammalian host is used. The HA tag corresponds to an epitope derived from the influenza hemagglutinin protein (Wilson et al., Cell, 37:767 [1984]).

2. Chemical Synthesis of VIP Polypeptides

In an alternate embodiment of the invention, the coding sequence of VIP genes, and in particular of any one or more of VIP3, VIP4, VIP5, or VIP6 genes, is synthesized, in whole or in part, using chemical methods well known in the art (See e.g., Caruthers et al., Nucl. Acids Res. Symp. Ser., 7:215-233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807-2817 [1981]). In other embodiments of the present invention, the protein itself is produced using chemical methods to synthesize either an entire VIP amino acid sequence (for example, SEQ ID NOs: 5 and/or 6) or a portion thereof. For example, peptides are synthesized by solid phase techniques, cleaved from the resin, and purified by preparative high performance liquid chromatography (See e.g., Creighton, Proteins Structures And Molecular Principles, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science, 269:202-204 [1995]) and automated synthesis may be achieved, for example, using ABI 431A Peptide Synthesizer (Perkin Elmer) in accordance with the instructions provided by the manufacturer. Additionally, the amino acid sequence of VIP, or any part thereof, may be altered during direct synthesis and/or combined using chemical methods with other sequences to produce a variant polypeptide.

3. Generation of VIP Antibodies

In some embodiments of the present invention, antibodies are generated to allow for the detection and characterization of a VIP protein. The antibodies may be prepared using various immunogens. In one embodiment, the immunogen is an *Arabidopsis* VIP peptide (e.g., an amino acid sequence as depicted in SEQ ID NOs:5 or 6 or 11 or 12), or a fragment thereof, to generate antibodies that recognize a plant VIP protein. Such antibodies include, but are not limited to polyclonal, monoclonal, chimeric, single chain, Fab fragments, and Fab expression libraries.

Various procedures known in the art may be used for the production of polyclonal antibodies directed against a VIP protein. For the production of antibody, various host animals can be immunized by injection with the peptide corresponding to the VIP protein epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward a VIP protein, it is contemplated that any technique that provides for the production of antibody molecules by continuous cell lines in culture finds use with the present invention (See e.g., Harlow and Lane, Antibodies: A Laboratory Manual, Cold Spring Harbor Laboratory Press, Cold Spring Harbor, N.Y.). These include but are not limited to the hybridoma technique originally developed by Kohler and Milstein (Kohler and Milstein, Nature, 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies may be generated by human hybridomas (Cote et al., Proc. Natl. Acad. Sci. USA, 80:2026-2030 [1983]) or by transforming human B cells with EBV virus in vitro (Cole et al., in Monoclonal Antibodies and Cancer Therapy, Alan R. Liss, pp. 77-96 [1985]).

In addition, it is contemplated that techniques described for the production of single chain antibodies (U.S. Pat. No. 4,946,778) find use in producing a VIP protein-specific single chain antibodies. An additional embodiment of the invention utilizes the techniques described for the construction of Fab expression libraries (Huse et al., Science, 246:1275-1281 [1989]) to allow rapid and easy identification of monoclonal Fab fragments with the desired specificity for a VIP protein.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of a VIP protein (e.g., for Western blotting), measuring levels thereof in appropriate biological samples, etc. The antibodies can be used to detect a VIP protein in a biological sample from a plant. The biological sample can be an extract of a tissue, or a sample fixed for microscopic examination.

The biological samples are then be tested directly for the presence of a VIP protein using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of a VIP protein detected by immunoblotting (Western blotting). Immunoblotting techniques are generally more effective with antibodies generated against a peptide corresponding to an epitope of a protein, and hence, are particularly suited to the present invention.

C. Expression of Cloned VIP Genes

In other embodiment of the present invention, nucleic acid sequences corresponding to the VIP genes, homologs and mutants as described above may be used to generate recombinant DNA molecules that direct the expression of the encoded protein product in appropriate host cells.

As will be understood by those of skill in the art, it may be advantageous to produce VIP-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) can be selected, for example, to increase the rate of VIP expression or to produce recombinant RNA transcripts having desirable properties, such as a longer half-life, than transcripts produced from naturally occurring sequence.

1. Vectors for Production of VIP.

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (e.g., SEQ ID NOs: 1-4). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the nucleic acid sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of VIP

In a further embodiment, the present invention provides host cells containing the above-described constructs. In some embodiments of the present invention, the host cell is a higher eukaryotic cell (e.g., a plant cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), 293T, C127, 3T3, HeLa and BHK cell lines, NT-1 (tobacco cell culture line), root cell and cultured roots in rhizosecretion (Gleba et al., Proc Natl Acad Sci USA 96: 5973-5977 [1999])

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

V. Methods of Modifying Plant Phenotype by Manipulating VIP Gene Expression

The present invention also provides methods of using VIP genes. In some embodiments, the sequences are used for research purposes. For example, nucleic acid sequences comprising coding sequences of a VIP gene, for example any one or more of VIP3, VIP4, VIP5, or VIP6, are used to discover other VIP genes. In other embodiments, endogenous plant VIP genes, such as any one or more of VIP3, VIP4, VIP5, or VIP6 genes, are silenced, for example with antisense RNA or by cosuppression, and the effects on flowering time and development observed. In other embodiments, modifications to nucleic acid sequences encoding VIP genes, such as any one or more of VIP3, VIP4, VIP5, or VIP6 genes, are made, and the effects observed in vivo; for example, modified nucleic sequences encoding at least one VIP gene are utilized to transform plants in which endogenous VIP genes are silenced by antisense RNA technology, and the effects observed. In other embodiments, VIP genes, either unmodified or modified, are expressed in in vitro translation and/or transcription systems, and the interaction of the transcribed and/or translation product with other system components (such as nucleic acids, proteins, lipids, carbohydrates, or any combination of any of these molecules) observed.

In other embodiments, VIP gene sequences are utilized to over-ride a vernalization phenotype, and/or to promote early flowering. In yet other embodiments, VIP gene sequences are utilized to confer a vernalization phenotype, and/or to inhibit or delay early flowering, or to promote late flowering. Thus, it is contemplated that nucleic acids encoding a VIP polypeptide of the present invention may be utilized to either increase or decrease the level of VIP mRNA and/or protein in transfected cells as compared to the levels in wild-type cells.

In some embodiments, the present invention provides methods to over-ride a vernalization phenotype, and/or to promote early flowering, in plants which require vernalization, by disrupting the function of at least one VIP gene in the plant. In these embodiments, the function of at least one VIP gene is disrupted by any effective technique, including but not limited to antisense, co-suppression, and RNA interference, as is described above and below.

In yet other embodiments, the present invention provides methods to add a vernalization phenotype and/or late flowering to plants in which vernalization is not otherwise required and/or which flower early, by expression of at least one heterologous VIP gene. Thus, in some embodiments, nucleic acids comprising coding sequences of at least one VIP gene, for example any one or more of VIP1-7, are used to transform plants without vernalization requirements and/or early flowering, thereby conferring the requirement for vernalization and promoting late flowering. As noted above, it is believed that at least some of the VIP gene products may interact together as components of a multi-molecular protein complex, and act to activate FLC gene expression. It is contemplated that some particular plant species or cultivars do not have any VIP genes; for these plants, it is necessary to transform a plant with all the VIP genes required to confer the vernalization and/or late flowering phenotype. It is contemplated that other particular plant species or cultivars may possess at least one VIP gene; thus, for these plants, it is necessary to transform a plant with those VIP genes which can interact with endogenous VIP genes in order to confer the vernalization and/or late flowering phenotype. The presence of VIP genes in a species or cultivar can be tested by a number of ways, including but not limited to using probes from genomic or cDNA VIP coding sequences, or by using antibodies specific to VIP polypeptides. The additional VIP gene(s) needed to confer the desired phenotype can then be transformed into a plant to confer the phenotype. In these embodiments, plants are transformed with VIP genes as described above and below.

In yet other embodiments, disruption of the function of at least on VIP gene is used to impart male sterility to plants in which flowers are otherwise both male and female fertile. This is based upon the observation that the flowers of vip mutants are typically male sterile, but female fertile. In these embodiments, the function of at least one VIP gene is disrupted by any effective technique, including but not limited to antisense, co-suppression, and RNA interference, as is described above and below.

As described above, in some embodiments, it is contemplated that the nucleic acids encoding a VIP polypeptide of the present invention may be utilized to decrease the level of VIP mRNA and/or protein in transfected cells as compared to the levels in wild-type cells. In some of these embodiments, the nucleic acid sequence encoding a VIP protein of the present invention is used to design a nucleic acid sequence encoding a nucleic acid product which interferes with the expression of the nucleic acid encoding a VIP polypeptide, where the interference is based upon a coding sequence of the encoded VIP polypeptide. Exemplary methods are described further below.

One method of reducing VIP expression utilizes expression of antisense transcripts. Antisense RNA has been used to inhibit plant target genes in a tissue-specific manner (e.g., van der Krol et al. (1988) Biotechniques 6:958-976). Antisense inhibition has been shown using the entire cDNA sequence as well as a partial cDNA sequence (e.g., Sheehy et al. (1988) Proc. Natl. Acad. Sci. USA 85:8805-8809; Cannon et al. (1990) Plant Mol. Biol. 15:39-47). There is also evidence that 3' non-coding sequence fragment and 5' coding sequence fragments, containing as few as 41 basepairs of a 1.87 kb cDNA, can play important roles in antisense inhibition (Ch'ng et al. (1989) Proc. Natl. Acad. Sci. USA 86:10006-10010).

Accordingly, in some embodiments, a VIP encoding-nucleic acid of the present invention are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *Solanum nodiflorum* mottle virus and subterranean clover mottle virus. The design and use of target RNA-specific ribozymes is described in Haseloff, et al. (1988) Nature 334:585-591. Ribozymes targeted to the mRNA of a lipid biosynthetic gene, resulting in a heritable increase of the target enzyme substrate, have also been described (Merlo AO et al. (1998) Plant Cell 10: 1603-1621).

Another method of reducing VIP expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial CDNA sequence (730 bp of a 1770 bp cDNA) are known (e.g., Napoli et al. (1990) Plant Cell 2:279-289; van der Krol et al. (1990) Plant Cell 2:291-299; Smith et al. (1990) Mol. Gen. Genetics 224:477-481). Accordingly, in some embodiments the nucleic acid sequences encoding a VIP of the present invention are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley SV et al. (2001) Plant J. 27: 581-590). Another method to decrease expression of a gene (either endogenous or exogenous) is via siRNAs. siRNAs can be applied to a plant and taken up by plant cells; alternatively, siRNAs can be expressed in vivo from an expression cassette.

A. Transgenic Plants, Seeds, and Plant Parts

Plants are transformed with at least one heterologous gene encoding a VIP gene, or encoding a sequence designed to decrease VIP gene expression, according to any procedure well known or developed in the art. It is contemplated that these heterologous genes, or nucleic acid sequences of the present invention and of interest, are utilized to increase the level of the polypeptide encoded by heterologous genes, or to decrease the level of the protein encoded by endogenous genes.

1. Plants

The methods of the present invention are not limited to any particular plant. Indeed, a variety of plants are contemplated, including but not limited to tomato, potato, tobacco, pepper, rice, corn, barley, wheat, *Brassica, Arabidopsis*, sunflower, soybean, poplar, and pine.

2. Vectors

The methods of the present invention contemplate the use of a heterologous gene encoding a VIP gene, or encoding a sequence designed to decrease VIP gene expression, as described previously. Heterologous genes include but are not limited to naturally occurring coding sequences, as well variants encoding mutants, variants, truncated proteins, and fusion proteins, as described above.

Heterologous genes intended for expression in plants are first assembled in expression cassettes comprising a promoter. Methods which are well known to or developed by those skilled in the art may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (See e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y).

In general, these vectors comprise a nucleic acid sequence encoding a VIP gene, or encoding a sequence designed to decrease VIP gene expression, (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al., Plant Physiol 120: 979-992 [1999]); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187, 267); a tetracycline-inducible promoter (U.S. Pat. No. 5,057, 422); and seed-specific promoters, such as those for seed storage proteins (e.g., phaseolin, napin, oleosin, and a promoter for soybean beta conglycin (Beachy et al., EMBO J. 4: 3047-3053 [1985])). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tm1 terminator, the pea rbcS E9 terminator, and the nopaline and octopine synthase terminator (See e.g., Odell et al., Nature 313:810 [1985]; Rosenberg et al., Gene, 56:125 [1987]; Guerineau et al., Mol. Gen. Genet., 226(1-2):141 [1991]; Proudfoot, Cell, 64:671 [1991]; Sanfacon et al., Genes Dev., 5:141; Mogen et al., Plant Cell, 2:1261 [1990]; Munroe et al., Gene, 91:151 [1990]; Ballas et al., Nucleic Acids Res. 17:7891 [1989]; Joshi et al., Nucleic Acid Res., 15:9627 [1987]).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al., Genes Develop. 1: 1183 [1987]). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Kalderon et al., Cell 39:499 [1984]; Lassner et al., Plant Molecular Biology 17:229 [1991]), a plant translational consensus sequence (Joshi, Nucleic Acids Research 15:6643 [1987]), an intron (Luehrsen and Walbot, Mol.Gen. Genet. 225:81 [1991]), and the like, operably linked to the nucleic acid sequence encoding a VIP gene.

In preparing the construct comprising the nucleic acid sequence encoding a VIP gene, or encoding a sequence designed to decrease VIP gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra, Gene 19: 259 [1982]; Bevan et al., Nature 304:184 [1983]), the bar gene which confers resistance to the herbicide phosphinothricin (White et al., Nucl Acids Res. 18:1062 [1990]; Spencer et al., Theor. Appl. Genet. 79: 625 [1990]), the hph gene which confers resistance to the antibiotic hygromycin (Blochlinger and Diggelmann, Mol. Cell. Biol. 4:2929 [1984]), and the dhfr gene, which confers resistance to methotrexate (Bourouis et al., EMBO J., 2:1099 [1983]).

In some preferred embodiments, the vector is adapted for use in an *Agrobacterium* mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted VIP polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

3. Transformation Techniques

Once a nucleic acid sequence encoding a VIP gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See e.g., U.S. Pat. Nos 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al., PNAS, 87:8526 [1990]; Staub and Maliga, Plant Cell, 4:39 [1992]). The presence of cloning sites between these markers allowed creation of a plastid targeting vector introduction of foreign DNA molecules (Staub and Maliga, EMBO J., 12:601 [1993]). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, PNAS, 90:913 [1993]). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway, Mol. Gen. Genet, 202:179 [1985]). In still other embodiments, the vector is transferred into the plant cell by using polyethylene glycol (Krens et al., Nature, 296:72 [1982]; Crossway et al., BioTechniques, 4:320 [1986]); fusion of protoplasts with other entities, either minicells, cells, lysosomes or other fusible lipid-surfaced bodies (Fraley et al., Proc. Natl. Acad. Sci., USA, 79:1859 [1982]); protoplast transformation (EP 0 292 435); direct gene transfer (Paszkowski et al., EMBO J., 3:2717 [1984]; Hayashimoto et al., Plant Physiol. 93:857 [1990]).

In still further embodiments, the vector may also be introduced into the plant cells by electroporation. (Fromm, et al., Pro. Natl Acad. Sci. USA 82:5824, 1985; Riggs et al., Proc. Natl. Acad. Sci. USA 83:5602 [1986]). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.). (See e.g., U.S. Pat. No. 4,945,050, herein incorporated by reference; and McCabe et al., Biotechnology 6:923 [1988]). See also, Weissinger et al., Annual Rev. Genet. 22:421 [1988]; Sanford et al., Particulate Science and Technology, 5:27 [1987] (onion); Svab et al., Proc. Natl. Acad. Sci. USA, 87:8526 [1990] (tobacco chloroplast); Christou et al., Plant Physiol., 87:671 [1988] (soybean); McCabe et al., Bio/Technology 6:923 [1988] (soybean); Klein et al., Proc. Natl. Acad. Sci. USA, 85:4305 [1988] (maize); Klein et al., Bio/Technology, 6:559 [1988] (maize); Klein et al., Plant Physiol., 91:4404 [1988] (maize); Fromm et al., Bio/Technology; 8:833 [1990]; and Gordon-Kamm et al., Plant Cell, 2:603 [1990] (maize); Koziel et al., Biotechnology, 11:194 [1993] (maize); Hill et al., Euphytica, 85:119 [1995] and Koziel et al., Annals of the New York Academy of Sciences 792:164 [1996]; Shimamoto et al., Nature 338: 274 [1989] (rice); Christou et al., Biotechnology, 9:957 [1991] (rice); Datta et al., Bio/Technology 8:736 [1990] (rice); European Patent Application EP 0 332 581 (orchardgrass and other Pooideae); Vasil et al., Biotechnology, 11:1553 [1993] (wheat); Weeks et al., Plant Physiol., 102: 1077 [1993] (wheat); Wan et al., Plant Physiol. 104: 37 [1994] (barley); Jahne et al., Theor. Appl. Genet. 89:525 [1994] (barley); Knudsen and Muller, Planta, 185:330 [1991] (barley); Umbeck et al., Bio/Technology 5: 263 [1987] (cotton); Casas et al., Proc. Natl. Acad. Sci. USA 90:11212 [1993] (sorghum); Somerset al., Bio/Technology 10:1589 [1992] (oat); Torbert et al., Plant Cell Reports, 14:635 [1995] (oat); Weeks et al., Plant Physiol., 102:1077 [1993] (wheat); Chang et aL, WO 94/13822 (wheat) and Nehra et al., The Plant Journal, 5:285 [1994] (wheat).

In addition to direct transformation, in some embodiments, the vectors comprising a nucleic acid sequence encoding a VIP gene are transferred using *Agrobacterium*-mediated transformation (Hinchee et al., Biotechnology, 6:915 [1988]; Ishida et al., Nature Biotechnology 14:745 [1996]). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell, Science, 237: 1176 [1987]). Species which are susceptible infection by *Agrobacterium* may be transformed in vitro.

4. Regeneration

After selecting for transformed plant material which can express a heterologous gene encoding a VIP gene, whole plants are regenerated. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. III, 1986. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

5. Generation of Transgenic Lines

Transgenic lines are established from transgenic plants by tissue culture propagation. The presence of nucleic acid sequences encoding an exogenous VIP gene or mutants or variants thereof may be transferred to related varieties by traditional plant breeding techniques.

These transgenic lines are then utilized for evaluation of pathogen resistance and other agronomic traits.

B. Evaluation of Flowering Time and Development

The confirmed transgenic plants and lines are tested for the effects of the transgene on flowering requirements and time and development. The parameters evaluated for flowering requirements and time and development are compared to those in control untransformed plants and lines. Parameters evaluated include determining time to flowering from germination, and effects of cold treatment on time of flowering. Time to flowering can be expressed as a number of days, or as a developmental state; for example, time to flowering in *Arabidopsis* can be measured as the total number of leaves produced on the primary stem. These tests are conducted both in the greenhouse and in the field.

EXPERIMENTAL

The following examples are provided in order to demonstrate and further illustrate certain preferred embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade);

Example 1

Experimental Procedures: VIP4 Gene

This example describes the experimental procedures used to identify, clone, and characterize the VIP4 gene.

Plant Material and Growth Conditions

Introgression line Col:FRI$^{SF2}$ consists of the FRI locus from ecotype San Feliu-2 (FRI$^{SF2}$) introgressed into the Columbia (Col) ecotype through six successive backcrosses and made homozygous by self-pollination (Lee et al. (1994) *Plant J.* 6, 903-909). Line FN231 contains a fast-neutronflc allele isolated in the Col:FRI$^{SF2}$ background, and is identical with flc-1 described by Michaels and Amasino ((1999) *Plant Cell*, 11, 949-956). Line FN235, containing a fast-neutronfri allele isolated in the Col:FRISF$^2$ background, is as described by Michaels and Amasino ((1999) *Plant Cell*, 11, 949-956). The ld-1 mutant in the Col background was obtained from the *Arabidopsis* Biological Resource Center (ABRC) at The Ohio State University. Standard growth conditions were 22° C. under 100-180 μmol m-2·sec-1 of cool white fluorescent lighting and 16 hr light/8 hr dark (long-day) or 8 h light/16 h dark (short-day) photoperiods. For vernalizing cold treatments, seeds were surface-sterilized, placed on agar-solidified germination medium as described by van Nocker et al. ((2000) *Plant Mol. Biol.* 44, 107-122), and grown at 4° C. under SD photoperiods. To evaluate flowering time, plants were grown individually in 5.7×5.7×7.5 cm pots. Plant transformations used the floral dip method of Clough and Bent ((1998) *Plant J.* 16, 735-743) and *Agrobacterium* strain ABI.

Mutagenesis and Screening

For T-DNA mutagenesis, a binary vector designated pPZP201 :BAR, containing a 5' mannopine synthase/glufosinate resistance/3' octopine synthase cassette cloned into the SmaI site of pPZP201 (Hajdukiewicz et al. (1994) *Plant Mol. Biol.* 25, 989-994), was introduced into Col:FRI$^{SF2}$ plants. Seeds from infiltrated plants (T1 seeds) were subjected to a vernalizing cold treatment, transferred to soil for further growth, and herbicide-resistant T1 plants were allowed to self-pollinate and set seed. Seeds from approximately 500 T1 plants were pooled. Approximately 5,000 T2 plants from each pool were screened for early flowering in the absence of cold. Fast-neutron mutagenesis and screening were performed as described by Michaels and Amasino ((1999) *Plant Cell*, 11, 949-956). FLC RNA expression was evaluated in approximately 14-d-old progeny (T3 or M3) plants grown without a cold treatment in SD conditions. To test for genetic complementation of theflc orfri mutations, T3 or M3 individuals were crossed with lines FN231 and FN235, and flowering time was evaluated in F1 progeny.

Molecular Techniques

DNA was isolated essentially as described by Murray and Thompson (1980); RNA was isolated as described by Liu et al. ((2002) *Physiol. Plant.* 114, 125-134). DNA and RNA gel-blot analyses were carried out as described by Liu et al. ((2002) *Physiol. Plant.* 114, 125-134). The probe for gel-blot analyses of VIP4 was a 432-bp fragment amplified from genomic DNA using primers VIP4-F1 (5'..ATGGAC-GAAAGGAGAGTGAAAG..3') (SEQ ID NO:17) and VIP4-R1 (5'..GGAATCAGAATATGAGACGGAAG..3') (SEQ ID NO:18); the probe for gel-blot analysis of FLC was a 510-bp RT-PCR product corresponding to FLC coding region but excluding the conserved MADS-domain. This segment of the FLC gene does not exhibit significant sequence homology with any other *Arabidopsis* gene. For inverse-PCR, 200 ng of restriction endonuclease-digested genomic DNA was purified using the QIAquick PCR Purification Kit (QIAGEN; Valencia, Calif.), and subsequently incubated with 10 u T4 DNA ligase (Roche; Indianapolis, Ind.) in a final reaction volume of 30 ml at 16° C. overnight. DNA was amplified directly from 2 µl of the ligation mixture using Advantage CDNA Polymerase Mix (Clontech, Palo Alto, Calif.).

For identification of VIP4 cDNAs, shoot apex cDNA libraries were constructed. Vernalized and nonvernalized Col:FRI$^{SF2}$ plants were grown under SD conditions, and when plants had formed 20-25 rosette leaves, 1-2 mm-thick sections containing the shoot apex were excised. Library construction utilized the ZAP Express XR system (Stratagene; La Jolla, Calif.). Library A contained ~1.5-8.0 kbp cDNAs and had a primary titre of $6.25 \times 10^6$ recombinants; library B contained ~0.5-3.0 kbp cDNAs and had a primary titre of $4.25 \times 10^6$ recombinants.

Construction of Transgenic *Arabidopsis* Lines

For molecular complementation analysis, the bacteriophage P1 clone MAF19 was obtained from the Kazusa DNA Research Institute (Yana, Kisarazu, Chiba, Japan), amplified in *E. coli*, purified using the Qiagen Plasmid Midi Kit, and subjected to restriction with NsiI. A ~7.1 kb fragment containing the VIP4 transcriptional unit and adjacent intergenic regions was cloned into the PstI site of binary vector PZP212 (Hajdukiewicz et al., 1994), and introduced into the vip4-1 mutant background. For antisense expression and constitutive expression, a DNA segment containing the VIP4 transcribed region was amplified by PCR using primers VIP4-F1 and VIP4-R2 (5'..AGGCAAACACAAGCT-CACTATC..3') (SEQ ID NO:19), and cloned into the BamHI site of binary vector pPZP201:BAR:35S in reverse (for antisense expression) or forward (for constitutive expression) orientations. The pPZP201:BAR:35S plasmid was engineered by inserting the cauliflower mosaic virus (CaMV) 35S promoter from plasmid pBI121 (Clontech) into the XbaI site of pPZP201:BAR (above).

Example 2

VIP4 Gene: Identification, Cloning, and Characterization

This example describes the identification, cloning, and characterization of the VIP4 gene.

A Genetic Screen for Activators of FLC

To identify potential activators of FLC, the winter-annual, Col:FRI$^{SF2}$ genetic background, was mutagenized and screened for recessive mutations that conferred cold-independent, early flowering. Early-flowering lines were rescreened by assaying for reduced FLC RNA expression in seedlings, where FLC RNA is typically easily detectable. To eliminate further consideration of lines with mutations in either the FLC or the FRI genes, mutants were also used in genetic complementation analysis with lines FN231 and FN235, carrying loss-of-function mutations in the FLC and FRI genes, respectively. Early-flowering lines that exhibited reduced FLC RNA expression, and that were not likely to represent new alleles of FLC or FRI, were sorted into allelic groups through complementation analysis. This strategy resulted in the identification of several complementation groups representing mutants designated vernalization independence (vip) mutants. The vip4 group, represented by two T-DNA alleles and one fast-neutron allele, was selected for further study. In these experiments, FLC RNA expression was analyzed in wild-type (WT) and vip4 mutant plants. RNA was extracted from aerial portions of 14 d-old, wild-type and vip4-1 seedlings and analyzed by gel blotting using an FLC probe as described in Example 1. The membrane was subsequently stripped and reprobed with an 18S rDNA probe to indicate the integrity and relative quantity of total RNA in each lane. FLC expression was not detectable in plants carrying the T-DNA allele vip4-1, as determined by gel-blot analysis of seedling RNAs, indicating that VIP4 is a strong activator of FLC.

Figure 7:
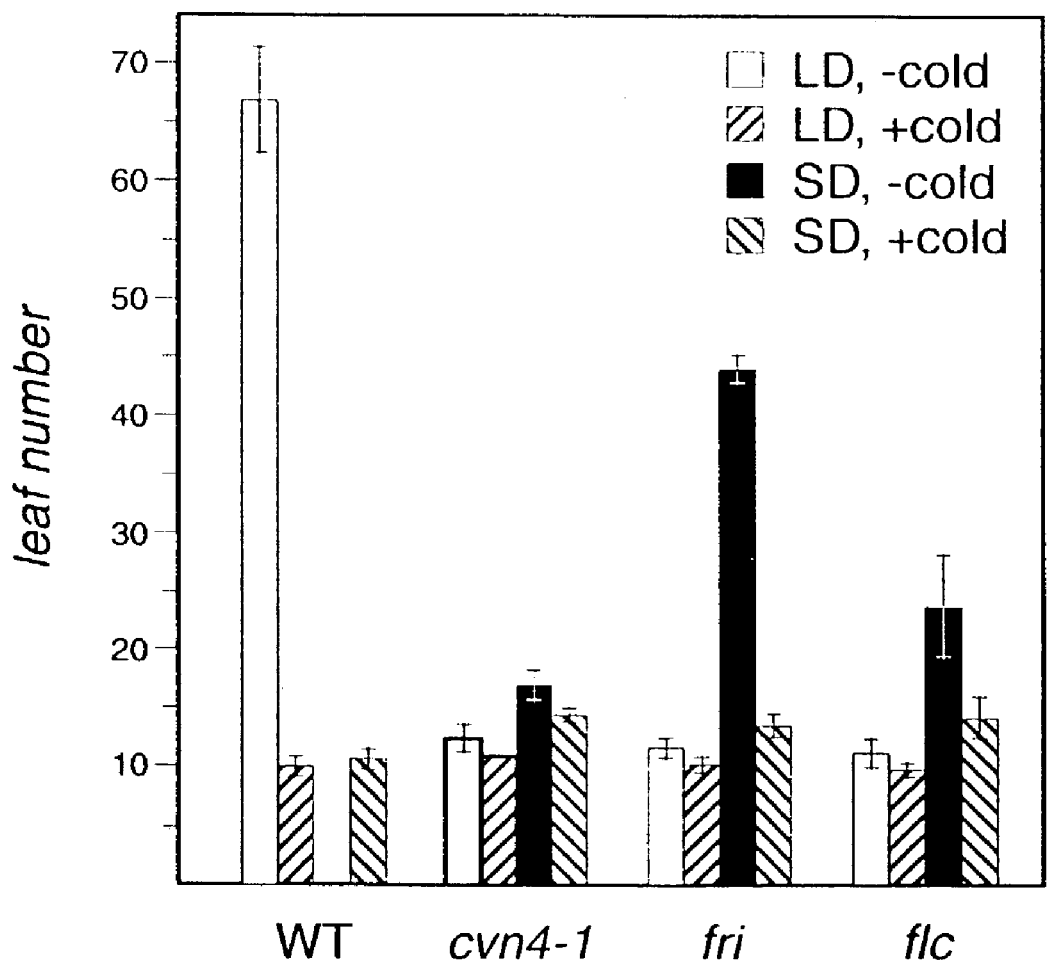
FIG. 7 shows the flowering time of wild-type plants, vip4 (cvn4) mutants, and mutants lacking activity of FRI or FLC. Wild-type (WT), vip4-1 (cvn4-1) mutants, and the FN231 and FN235 mutants lacking activity of FLC or FRI, respectively, were grown without a cold treatment (−cold), or after a 70-d cold treatment (+cold) under long-day (LD) or short-day (SD) photoperiods, as described in Example 1. 'Leaf number' indicates the total number of rosette and cauline leaves produced. Data is the mean and standard deviation for at least 12 plants. Wild-type plants grown in SD without cold did not flower during the course of this experiment.

To address the relationship between VIP4, FLC, and FRI, the effects of a vernalizing cold treatment on the flowering response of vip4-1 relative to that of wild-type, flc, and fri plants was evaluated (FIG. 7). Flowering time was measured from a developmental perspective, as the total number of leaves produced on the primary stem. When grown under inductive (long-day) photoperiods in the absence of cold, vip4 mutants flowered at approximately the same time as the fc and fri mutants and vernalized wild-type plants. However, significant differences were apparent when plants were grown under noninductive (short-day) photoperiods, where the promotive activity of genes acting through perception of inductive photoperiods is expected to be minimized. The flc mutants flowered earlier (23.9±4.4 leaves) than the fri mutants (44.1±1.2 leaves), suggesting that FLC retains a small degree of activity even in the absence of FRI function, and this is in accordance with previous observations (Michaels and Amasino, 2001). However, under these conditions, vip4-1 plants flowered even earlier (17.1±1.3 leaves) than flc plants. This indicates that VIP4 may also repress flowering outside of its positive regulation of FLC. Also similar to previous observations (Michaels and Amasino (2001) *Plant Cell*, 13, 935-941), cold reduced flowering time of flc mutants, suggesting that vernalization targets FLC-independent as well as FLC-dependent mechanisms. However, even vip4-1 plants showed a slight acceleration of flowering in response to cold, and vernalized wild-type plants flowered significantly earlier (10.7±0.9 leaves) than did vip4-1 plants grown in the absence of cold (FIG. 7). This suggests that, if vip4-1 is a null mutation, vernalization also involves a vip4-independent mechanism.

In addition to the flowering-time phenotype, vip4 plants exhibit defects in floral morphology. Among these is a widening of medial sepals, such that sepals typically fail to enclose the remainder of the floral bud in the latest stages of floral development. Petals are narrower than in wild-type flowers, and occasionally are greatly reduced in size. Stamens are often reduced in number to four or five. No defect in carpel morphology was apparent, and flowers are typically fully fertile. No additional phenotypic defects were obvious in vip4 mutants.

Cloning and Identification of the VIP4 Gene

Figure 8:
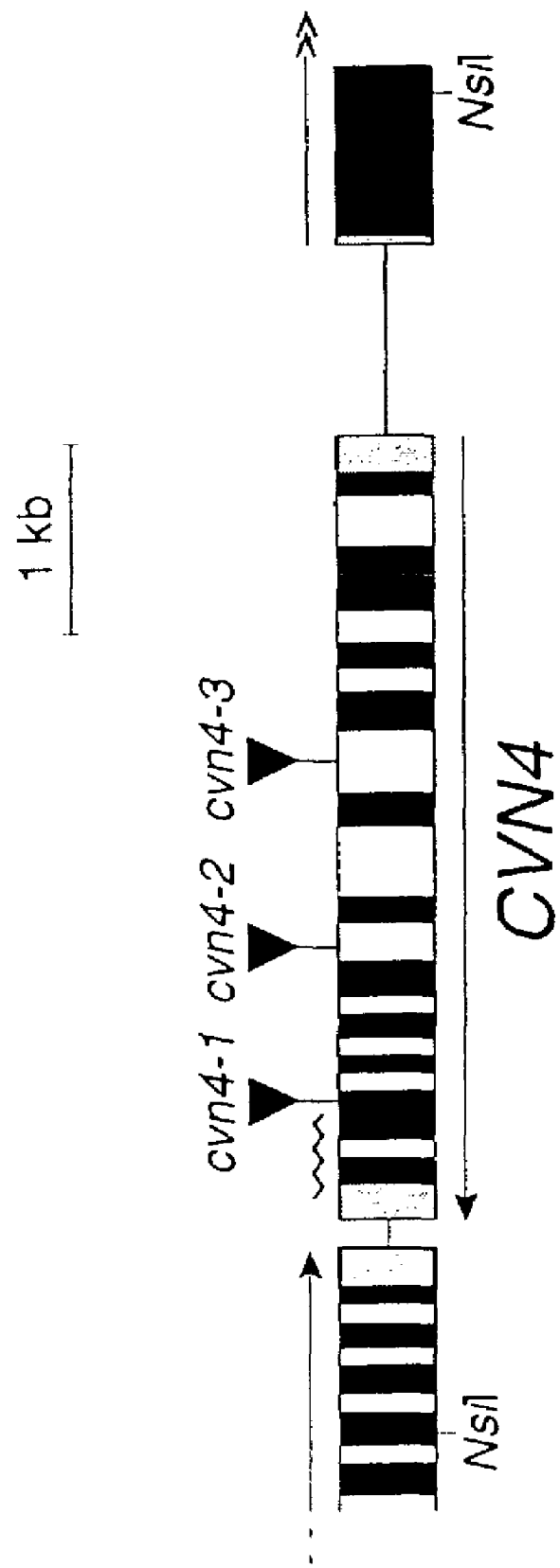
FIG. 8 shows a depiction of the region of chromosome V encompassing the VIP (CVN4) gene. The direction of transcription for VIP4 (CVN4) and two adjacent genes is indicated by arrows. Introns are shown as white boxes, whereas exons are shown as black (translated region) or gray (untranslated region) boxes. Only the proximal portion of adjacent genes are depicted; for these, intron/exon structure is shown as annotated by the *Arabidopsis* Genome Initiative, and the extent of untranslated regions is based on EST sequences in the GenBank/EMBL databases. The position of the inserted DNA for the vip4-1 (cvn4-1), vip4-2 (cvn4-2), and vip4-3 (cvn4-3) alleles is indicated. A zig-zagged line in the 3' region of the VIP4 (CVN4) gene indicates the probe used for RNA gel blot analyses. The NsiI sites delineating the region used to complement the vip4-1 (cvn4-1) mutation are indicated.

Because segregation data indicated that the vip4-1 mutation might be due to T-DNA integration, genomic DNA flanking the T-DNA was recovered by inverse-PCR, where it was observed that the T-DNA was inserted into the transcribed region of a predicted gene near the bottom of chromosome V, designated At5g61150 (FIG. 8). Subsequent characterization of the At5g61150 region of vip4-2 and vip4-3 plants indicated the presence in the transcribed region of a T-DNA for vip4-2, and a large genomic insertion, originating from the top of chromosome V, for vip4-3 (FIG. 8). Expression of VIP4 RNA expression was analyzed in wild-type (WT) and vip4 mutant plants. RNA was extracted from aerial portions of 14 day-old, wild-type and vip4-1 seedlings and analyzed by gel blotting using a VIP4 probe as described in Example 1. The membrane was subsequently stripped and reprobed with an 18S rDNA probe to indicate the integrity and relative quantity of total RNA in each lane. The results showed that in vip4-1 plants, RNAs hybridizing with an At5g61150 probe failed to accumulate to levels detectable by gel blotting of total RNAs, whereas these RNAs were readily detectable in wild-type plants. The observed size of the transcript was approximately 2.4 kb, consistent with the size derived from the annotation of the At5g61150 intron/exon structure provided by the *Arabidopsis* Genome Initiative. This predicted structure was confirmed by isolation and sequencing of several cDNAs from libraries prepared from Col:FRI$^{SF2}$ shoot apices.

To confirm the identification of the VIP4 gene, the entire At5g61150 transcriptional unit, plus immediately adjacent genomic regions, was introduced into the vip4-1 background, through *Agrobacterium*-mediated transformation. Primary transformants (T1 plants) were grown either in the absence of cold, or after a vernalizing cold treatment. All of the 20 T1 plants recovered in both cases were phenotypically indistinguishable from the wild-type, Col:FRI$^{SF2}$ plants, producing at least 60 leaves before flowering in the absence of cold, flowering very early when given a cold treatment, and exhibiting normal floral morphology. In nonvernalized progeny of a representative T1 plant, both VIP4 and FLC RNAs were expressed to levels similar to that seen in the wild-type plant. As additional evidence that At5g61150 is VIP4, expression of the At5g61150 gene in wild-type plants was disrupted through antisense RNA expression. For this experiment, a transgene was engineered in which the part of At5g61150 corresponding to the translated and 3' regions, including introns, was expressed in 3' to 5' orientation from the 35S CaMV promoter. A subset of the T1 plants recovered flowered very early in the absence of cold, and produced flowers with a vip4-like phenotype. Finally, several early-flowering plants from a transgenic population engineered to express the At5g61150 transcribed region in the 5' to 3' orientation from the 35S promoter (35S: VIP4) were recovered. The vernalization-independent early flowering of the VIP4-antisense and 35S: VIP4 plants was presumably due to suppression of the endogenous VIP4 gene, as VIP4 RNA did not accumulate to detectable levels in these plants. In addition, in contrast to nontransgenic, wild-type plants, FLC RNA was not detectable in leaf tissues of these early-flowering, VIP4-antisense and 35S: VIP4 plants, indicating that early flowering was mediated at least partly through loss of FLC expression. In these experiments, VIP4 and FLC RNA expression was analyzed in wild-type and transgenic plants. VIP4 and FLC RNA expression was evaluated in wild-type (WT) plants, a late-flowering transgenic plant expressing the VIP4 gene from the 35S promoter (35S: VIP4#5), and early-flowering transgenic plants expressing VIP4 antisense RNA (VIP4-AS#4) or expressing the VIP4 gene from the 35S promoter (35S:VIP4#9). RNA was extracted from rosette leaves of nonvernalized plants grown in LD photoperiods and analyzed by gel blotting, using VIP4 and FLC probes. Blots were subsequently stripped and reprobed with an 18S rDNA probe to indicate the integrity and relative quantity of total RNA in each lane.

The VIP4 gene (shown in FIG. 5) encodes a 633-residue (shown in FIG. 6), 72-kDa protein with a predicted pI of 4.4. Almost one-half of the residues are charged (Glu, Asp, His, Lys, Arg), and thus the VIP4 protein is highly hydrophilic; this hydrophilicity is most apparent in extensive amino-terminal and carboxyl-terminal regions. The VIP4 protein does not exhibit any motif currently defined in the PROSITE Dictionary of Protein Sites and Patterns. However, predominately within its less hydrophilic central domain, VIP4 exhibits sequence homology with the Leo1 protein from *S. cerevisiae*, and other hydrophilic proteins of unknown function from *S. pombe*, *C. elegans*, and *Drosophila* (23-29% identity over 239-311-amino acid segment).

RNA gel blotting was used to analyze the general spatial expression pattern of VIP4 in nonvernalized plants. Expression was analyzed in seedlings, shoot apices, rosette leaves, cauline leaves, inflorescence apices, flowers, stems, and roots of nonvernalized, Col:FRI$^{SF2}$ plants, as described above. In order to obtain reproductive tissues for analysis, plants were grown under long-day (LD) photoperiods. It was observed that VIP4 was expressed throughout the plant, with the potential exception of rosette leaves. RT-PCR was subsequently used to confirm that VIP4 was expressed in these tissues as well. This expression pattern generally paralleled that of FLC, which was also expressed ubiquitously, but at very low levels in the leaves. A search of current databases of expressed sequence tags (ESTs) resulted in the identification of a single EST (BE527160) originating from developing seeds, indicating that VIP4 is expressed in seed tissues as well.

To determine if the suppression of FLC RNA expression associated with vernalization might be mediated through suppression of VIP4, VIP4 RNA expression was evaluated in vernalized and nonvernalized seedlings. Expression was analyzed in aerial portions of 14 d-old Col:FRI$^{SF2}$ seedlings grown without a cold treatment (nonvernalized), or after a 40-d cold treatment (vernalized) under short-day photoperiods, as described above. It was observed that VIP4 RNA was expressed to similar levels irrespective of the vernalization status. The effectiveness of the cold treatment given to these plants was evident by the decrease of FLC RNA to nondetectable levels. This suggests that VIP4 is insufficient to activate FLC in vernalized plants, and that modulation of VIP4 RNA expression is unlikely to be involved in the vernalization response.

Genetic and Molecular Analysis of VIP4 Function

The relationship between VIP4, FRI, and an autonomous-pathway gene, LD, was further characterized through analysis of molecular epistasis. As previously reported (Michaels and Amasino (1999) *Plant Cell,* 11, 949-956), FLC RNA expression was not detected in the Col ecotype lacking activity of FRI, but it was expressed to readily detectable levels in the Col:FRI$^{SF2}$ line, and in an ld mutant in the Col background, which lacks activity of both FRI and LD. In contrast, VIP4 RNA was expressed to similar levels in all three genotypes. The observation that VIP4 RNA expression was similar between Col and Col:FRI$^{SF2}$ indicates that VIP4 is not likely to mediate the activation of FLC expression by FRI. Likewise, the observation that VIP4 expression was similar between ld-1 and its wild-type genetic background Col indicates that the derepression of FLC seen in mutants compromised for autonomous-pathway gene function is also unlikely to be mediated through VIP4.

To help define the role of VIP4 and especially its relationship to FLC, the effects of enhanced expression of VIP4 in transgenic plants were evaluated. Several plants expressing high levels of VIP4 RNA were identified from a 35S: VIP4 T1 population grown in the absence of cold (from experiments as described above). This RNA was apparently processed to the same extent as the endogenous VIP4 RNA, as evidenced by its co-migration with the VIP4 transcript from wild-type plants. These 35S: VIP4 T1 plants were phenotypically indistinguishable from wild-type Col:FR- $I^{SF2}$. Although VIP4 RNA accumulated to high levels in leaf tissues of these plants, FLC RNA expression was not enhanced in leaves, relative to its levels in wild-type plants (from experiments as described above), suggesting that ectopic VIP4 activity was not sufficient to activate FLC, even in the absence of vernalization.

Example 3

Experimental Procedures: VIP3 Gene

This example describes the experimental procedures used to identify, clone, and characterize the VIP3 gene.

Growth Conditions.

Arabidopsis seeds were either planted directly into artificial soil mix (Baccto Hi-Porosity Mix, Michigan Peat Co., Houston, Tex.) or surface-sterilized and germinated on sterile Germination Medium [2.5 mM 2-[N-Morpholino]ethanesulfonic acid, 375 mg/l Peters 20-20-20 Fertilizer (Scotts Company, Marysville, Ohio), pH adjusted to 5.7 with KOH, supplemented with 0.8% (w/v) Phytagar (Life Technologies, Gaithersburg, Md.)]. Standard growth conditions were 60-100 µmoles $m^{-2}$ $s^{-1}$ of fluorescent lighting in a 16h-light/8h-dark photoperiod at 22° C. and ~50% relative humidity. For a vernalizing cold treatment, seeds on Germination Medium were first placed at 4° C. under 20-50 µmoles $m^{-2}$ $s^{-1}$ of fluorescent lighting in a 8h-light/16h-dark photoperiod for 30 or 70 d. To evaluate flowering time, individual plants were grown in pots containing ~125 $cm^3$ soil.

Strains and Genetic Techniques.

Introgression line Col:FRI$^{SF2}$ consists of the dominant FRI locus from ecotype San Feliu-2 (FRI$^{SF2}$) introgressed into the Columbia (Col) ecotype through six successive backcrosses and made homozygous by self-pollination (Lee and Amasino, (1995) Plant Physiol. 108, 157-162). Introgression line Ler:FRI$^{SF2}$:FLC$^{SF2}$ consists of FRI$^S$ and the semidominant FLC locus from ecotype San Feliu-2 (FLC$^{SF2}$) both introgressed into the Landsberg erecta (Ler) genetic background through seven successive backcrosses and made homozygous through self-pollination (Lee et al., (1994) Plant J. 6, 903-909). The ld-1 mutant (ecotype Col-1) was obtained from the Arabidopsis Biological Resource Center (ABRC) at the Ohio State University (Columbus, Ohio). The E. coli strain harboring BAC F27B13 was obtained from the ABRC.

PCR-based molecular markers were developed to discriminate between wild-type and mutant alleles at the VIP3, FRI, and LD loci. A marker for presence of the wild-type, VIP3 allele was designed to amplify, from the wild-type allele, a region spanning the site of the vip3 mutation [primers: F27B13.7F2 (5'..TTGCAGGTGGAAGTAGTGC-CTC..3') (SEQ ID NO:20) and F27B13.7 R2 (5'..TGTCAT-CAGAGACACTAGCAAGTCG..3') (SEQ ID NO:21)]. To determine presence of the vzp3 allele, a marker was designed to amplify the right border region of the genomic insertion [primers: F27B13.7F2 and T16L4F (5'..GCCACT-GCCGCCAGTTTTATCAAG..3') (SEQ ID NO:22)]. A marker for discrimination between the FRI$^{SF2}$ and fri (in Col) alleles was based on a 16-bp length polymorphism within the FRI promoter as described by Johanson et al., (2000) Science 290, 344-347, and employed primers FRI16F (5'..TGGTGTTCCTTCAAACTTTAGG..3') (SEQ ID NO:23) and FRI16R (5'..GCTCAATCAGTCATTG-CACTC..3') (SEQ ID NO:24). A marker for discrimination between the LD and ld-1 alleles was based on the ld-1 mutation, which is localized within the LD transcribed region, and was generously provided by Dr. Scott Michaels, University of Wisconsin.

For analysis of genetic epistasis between vip3 and vip4-1, flowering time and floral morphology of the progeny of a VIP3/vip3 vip4-1/vip4-1 plant was analyzed. This plant was identified by PCR in an F2 population derived from a cross between vip3 and vip4-1.

Cloning of VIP3.

For mutagenesis of introgression line Col:FRI.sup.SF2, seeds were exposed to .about. 165 Gy of fast-neutron radiation, using the fast-neutron beam at the Michigan State University Cyclotron Laboratory. Seeds were then subjected to a vernalizing cold treatment, planted in soil, and plants were allowed to self-pollinate. M2 seed was collected in pools each representing .about.1,000 M1 individuals. pproximately 5,000 plants from each of 50 M2 families were screened for early flowering in the absence of a vernalizing cold treatment. Positional cloning utilized F2 progeny of a single F1 individual derived from a cross between vip3 and introgression line Ler:FRI.sup.SF2:FLC.sup.SF2. Bulked-segregant analysis was performed with 24 F2 individuals and molecular markers described by Lukowitz et al. (2000) Plant Physiol. 123, 795-805. Fine mapping was done entirely using PCR markers based on small insertion-deletion polymorphisms as characterized and cataloged by Cereon Corporation (TAIR website; courtesy of S. Rounsley).

Molecular Techniques.

BAC DNA was purified from 250-ml bacterial cultures using a conrmercially available kit (Qiagen, Inc., Valencia, Calif.). For PCR purposes, DNA was prepared from plant tissues using the CTAB-based method described by Lukowitz et al. (2000) Plant Physiol. 123:795-805. For DNA gel blotting, DNA was prepared from young leaf tissue the method of Michaels and Amasino (Plant J., 1998, May; 14(3):381-5 and Plant Cell, 2001, Apr; 13(4):935-41). RNA was prepared from plant tissues using Tri Reagent(Sigma) according to the manufacturer's instructions, and then further purified by precipitation in 2M LiCl. DNA- and RNA-gel blot analysis were carried out as previously described (van Nocker et al., (2000) J. Biol. Chem. 12150-12158). For detection of VIP3 RNA, the probe was a DNA corresponding to the entire VIP3 coding region, amplified from flower-derived cDNA using primers F27B13.7FBam (5'..AAAG-GATCCATGAAACTCGCAGGTCTGAAATCG..3') (SEQ ID NO:25) and F27B13.7RBam2 (AAAGGATCCGAAT-TGTTCATGAGTAATCATAGAGC..3') (SEQ ID NO:26). For detection of the FLC RNA the probe was a DNA corresponding to FLC transcribed sequence outside of the conserved MADS-box region, amplified from vegetative-apex-derived cDNA using primers FLC-F1 (5'..GGATCAT-CAGTCCAAAAGCTCTG..3') (SEQ ID NO:27) and FLC-R1 (5'..AGTATCACACACAAAGTCTCTTGG..3') (SEQ ID NO:28). For detection of AG RNA, the probes were DNAs representing transcribed sequence outside of the conserved MADS-box region, amplified from flower-derived cDNA using primers AG-F1 (5'..CGCACT-CATCGTCTTCTCTAGCCG..3') (SEQ ID NO:29), AG-R1 (5'..TCACTCCCGGCCATTTCCTTCAGC..3') (SEQ ID NO:30). PCR products were sequenced to verify identity.

For molecular complementation of the vip3 mutation, a ~6.4-kb Bam HI fragment derived from BAC F27B13 was ligated into the Bam HI site of vector pPZP:BAR, and introduced into wild-type plants through floral dipping. This DNA contained the entire predicted transcriptional units for AT4g29830 and AT4g29820, as well as partial transcriptional units for AT4g29840 and AT4g29810. The transgene was introduced into wild-type plants, several independent T1 lines were established, and then the transgene was introduced into the vip3 mutant through crossing. Herbicide-resistant progeny from these crosses were allowed to self-pollinate, and progeny from these plants were subjected to herbicide selection. Several lines failed to generate herbicide-resistant, vip3-like progeny. In these lines, analysis of several wild-type-like progeny by PCR indicated homozygosity for the vip3 allele.

For overexpression or antisense expression of VIP3 in transgenic plants, the VIP3 coding and 3' nontranslated region was amplified from genomic DNA using primers F27B13.7FBam (SEQ ID NO:25), and F27B13.7RBam (5'..AAAGGATCCAATGCCATCCCTGACATG-GCTTGC..3') (SEQ ID NO:31). These primers incorporate a BarnHI restriction endonuclease site into both termini. The PCR products were ligated into vector pGEM-T (Promega), the resulting construction was subjected to digestion with Bam HI, and the fragment containing the VIP3 coding and 3' region was ligated into the Bam HI site of vector pPZP:BAR:35S. This vector is a derivative of pPZP:BAR that contains a CaMV 35S promoter fragment cloned into the Hind III/Xba I site. Ligation products were obtained that contained the VIP3 fragment in both forward (sense) and reversed (antisense) orientation. These were introduced into Agrobacterium strain ABI, and the resulting strains were used to infect wild-type Col:FRI$^{SF2}$ plants through the floral dip procedure of Clough and Bent (1998). For selection of transgenic plants, seed from infiltrated plants (T1 seed) was distributed onto soil at a density of ~10 seeds/cm$^2$ and plants were sprayed twice weekly with a 1:1000 dilution of Finale (AgrEvo Environmental Health, Montvale, N.J.), which contains the herbicide glufosinate.

Sequence Analysis.

WD motifs in VIP3 and G.beta were identified using the Protein Sequence Analysis server administer at the BioMolecular Engineering Research Center, Boston University. Other sequence analyses were performed using BLAST on web servers maintained by the National Center for Biotechnology Information (NCBI;) or The Arabidopsis Information Resource (TAIR;) and programs of the Genetics Computer Group (GCG; Madison, Wis.).

Example 4

VIP3 Gene: Identification, Cloning, and Characterization

This example describes the identification, cloning, and characterization of the VIP3 gene.

Identification and Genetic Analysis of the VIP3 Locus.

To identify new floral repressors, a synthetic, late-flowering genetic background was mutagenized using fast neutrons, and mutant plants that flowered after producing fewer than 20-25 rosette leaves were recovered. Such early-flowering mutants were identified in 49 of the 50 M2 families screened, and a single mutant individual from each pool was selected for phenotypic analysis, which was performed with M3 plants, or with progeny derived from a backcross of the M2 plant to wild-type. Many of these mutants displayed one or more phenotypes that suggested a primary defect in light signaling e.g., light green foliage and/or elongated petioles. These mutants were not subjected to further analysis. Several of the remaining plants flowered at approximately the same time as wild-type plants that had been subjected to a previous vernalization treatment. One of these, designated CONSTITUTIVELY VERNALIZED 3 (VIP3), was selected for detailed study, and backcrossed three times in succession into the Col-FRI$^{SF2}$ wild-type background for analysis. FLC expression was not detectable in vip3 plants, as determined by gel-blot analysis of seedling RNAs, indicating that VIP3 is a strong activator of FLC. In these experiments, FLC RNA expression was analyzed in wild-type (WT) and vip3 mutant plants. RNA was extracted from aerial portions of 14 d-old, wild-type and vip3 seedlings and analyzed by gel blotting using an FLC probe as described in Example 3. The membrane was subsequently stripped and reprobed with an actin probe to indicate the integrity and relative quantity of total RNA in each lane.

In addition to the defect in flowering time (see below), vip3 plants exhibit several other defects in growth and development. Specifically, rosette leaves of vip3 plants are smaller than those of wild-type plants, and mutant plants have reduced apical dominance. In addition, flowers of vip3 plants exhibit abnormalities of organs in whorls 1-3. Sepals typically have irregular, translucent margins, and lateral sepals are always reduced in size. Petals are also reduced in size. Stamens are typically decreased in number to 4-5. Organs in whorls 1-3 are also often replaced by filamentous structures. The gynoecium is morphologically normal, but slightly reduced in size. Flowers are typically male-sterile, and self-pollination is rare.

To evaluate potential dominance of the vip3 mutation, a mutant was backcrossed to wild-type, and progeny were examined. Similar to wild-type plants, VIP3/vip3 plants flowered very late, or not at all, under photoperiodically inductive (LD) conditions in the absence of cold, and none of the phenotypic defects described above for the vip3 mutant were apparent in VIP3/vip3 plants, indicating that the vip3 mutation is effectively recessive. A population derived from a backcross between vip3 and wild-type plants produced mutant individuals in a ratio expected for Mendelian segregation of a single recessive locus. In addition, analysis of the progeny of reciprocal crosses between a wild-type plant and a VIP3/vip3 plant indicated that the vip3 mutation was transmitted through both male and female gametes with a frequency similar to that seen for the wild-type allele.

Flowering Response of the vip3 Mutant.

Figure 9:
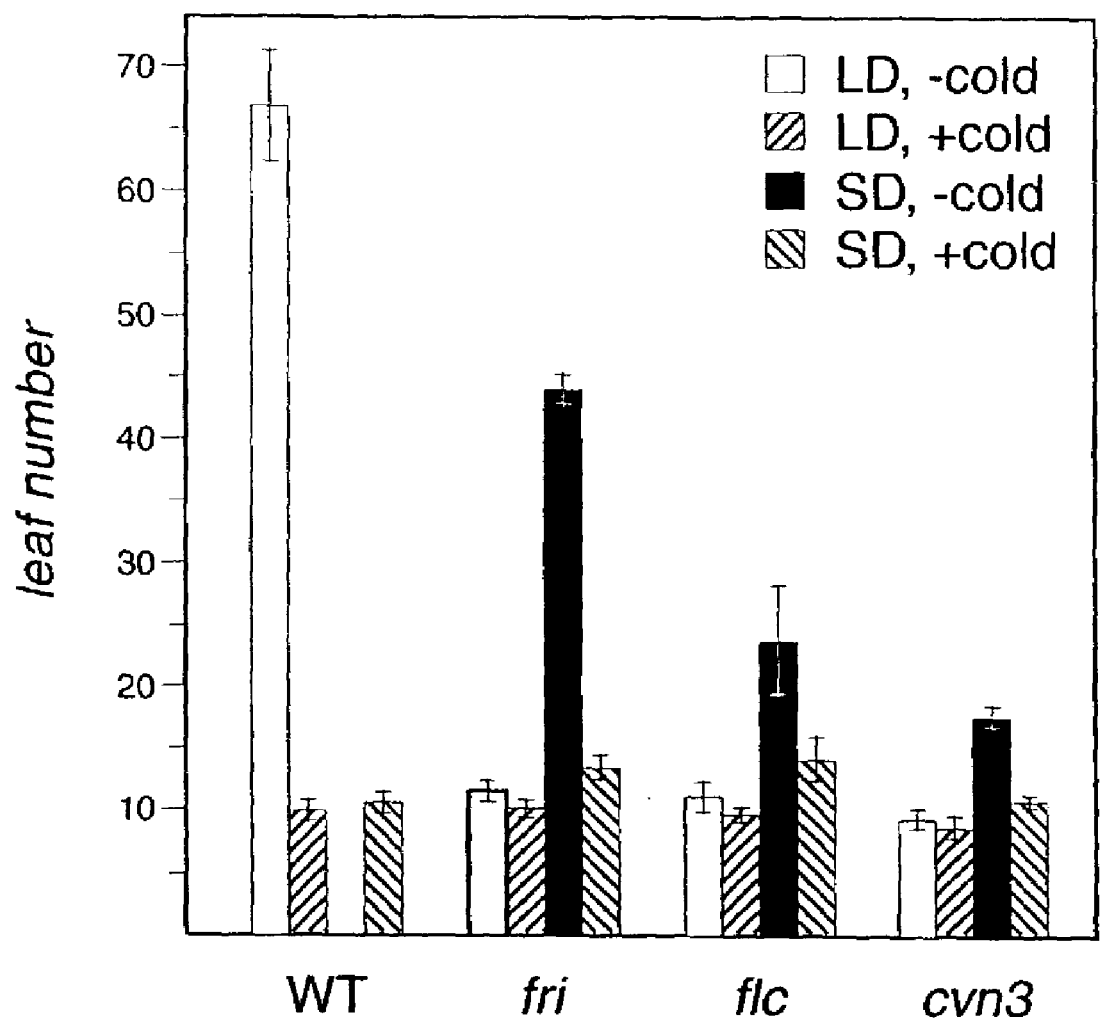
FIG. 9 shows the flowering time of wild-type plants, vip3 (cvn3) mutants, and mutants lacking activity of FRI or FLC. Wild-type (WT), vip3 (cvn3) mutants, and the FN231 and FN235 mutants lacking activity of FLC or FRI, respectively, were grown without a cold treatment (−cold), or after a 70-d cold treatment (+cold) under long-day (LD) or short-day (SD) photoperiods, as described in Example 3. 'Leaf number' indicates the total number of rosette and cauline leaves produced. Data is expressed as the mean and standard deviation for at least 12 plants. Wild-type plants grown in SD without cold did not flower during the course of this experiment.

The observation that the vip3 mutant flowered at approximately the same time as vernalized wild-type plants suggested that the predominant defect conferred by the vip3 mutation is on the vernalization pathway. In Arabidopsis, vernalization is mediated largely through repression of the flowering inhibitor gene FLC, as described above. To address the relationship between VIP3, FLC, and the FLC activator, FRI, the effects of a vernalizing cold treatment on the flowering response of the vip3 mutant relative to that of wild-type, flc, and fri plants was evaluated; the results as shown in FIG. 9. Flowering time was measured from a developmental perspective, and quantitated as the total number of leaves produced on the primary stem. When grown under inductive (long-day, or LD) photoperiods in the absence of cold, vip3 mutants flowered at approximately the same time as the flc and fri mutants, and vernalized wild-type plants. However, significant differences were apparent when plants were grown under noninductive (short-day or SD) photoperiods, where the promotive activity of genes acting through perception of inductive photoperiods is expected to be minimized. It was observed that flc mutants flowered earlier (23.9±4.4 leaves) than fri mutants (44.1±1.2 leaves), suggesting that FLC retains a small degree of activity even in the absence of FRI function, and this is in accordance with previous observations (Michaels and Amasino, 2001). However, under these conditions, vip3 plants flowered even earlier (17.1+1.3 leaves) than flc plants. This indicates that VIP3 may also repress flowering outside of its positive regulation of FLC. Cold also reduced flowering time of flc mutants, which is similar to previous observations, and suggests that vernalization targets FLC-independent as well as FLC-dependent mechanisms (Michaels and Amasino, 2001). However, even vip3 plants showed a slight acceleration of flowering in response to cold, and vernalized wild-type plants flowered significantly earlier (10.7±0.9 leaves) than did vip3 plants grown in the absence of cold (FIG. 9). This suggests that, if vip3 is a null mutation, vernalization also involves a vip3-independent mechanism.

Interactions with FRI and Autonomous Pathway.

Although it is not necessary to understand the underlying mechanism to practice the invention, and it is not intended that the invention be limited to any particular hypothesis or theory, it is hypothesized that one of several potential positions of the VIP3 gene within the regulatory hierarchy of flowering is as a negative regulator of the activity of the autonomous pathway, a function that the inventors have proposed for FRI, as described above. If this hypothesis is correct, then loss of VIP3 function would not be expected to suppress the late flowering associated with loss of autonomous pathway activity. This hypothesis was tested by evaluating the epistatic interactions between VIP3 and the autonomous pathway gene LD. A vip3 mutant plant (vip3/vip3 FRI/FRI iLD/LD) was crossed with the strong ld-1 mutant in the Col background (VIP3/VIP3fri/fri ld/ld), and plants that were homozygous for mutations in FRI, VIP3, and LD (vip3/vip3 fri/fri ld/ld) were identified from the corresponding F2 population using allele-specific molecular markers (as described in Example 3). These triple mutants were phenotypically similar to vip3 plants, flowering very early, failing to express FLC, and exhibiting aberrant floral morphology and a dwarfed growth habit (not shown). It was observed that vip3/ld double mutants containing an active FRI allele showed this phenotype as well. That the vip3 phenotype is effectively epistatic to the late-flowering, ld phenotype indicates that VIP3 is unlikely to function as an upstream regulator of the autonomous pathway, and thus has a function that is distinctly different from that of FRI. Thus, the results suggest that VIP3 functions predominately downstream of the autonomous pathway.

To determine if FRI has any flowering-repressive effect in a vip3 genetic background, the vip3 mutant was crossed with wild-type, Col plants (carrying the loss-of-function FRI$^{Col}$ allele), and a plant homozygous for FRI$^{Col}$ and heterozygous for vip3 was identified in the respective F2 population. This plant was allowed to self-pollinate and set seed, and flowering time was analyzed in the progeny. When grown under SD conditions, there was no significant difference in flowering time between vip3/vip3 fri$^{Col}$/fri$^{Col}$ and vip3/vip3 FRI$^{SF2}$/FRI$^{SF2}$ plants. These results indicated that vip3 was effectively epistatic to FRI.

Positional Cloning of the VIP3 Gene.

Figure 10:
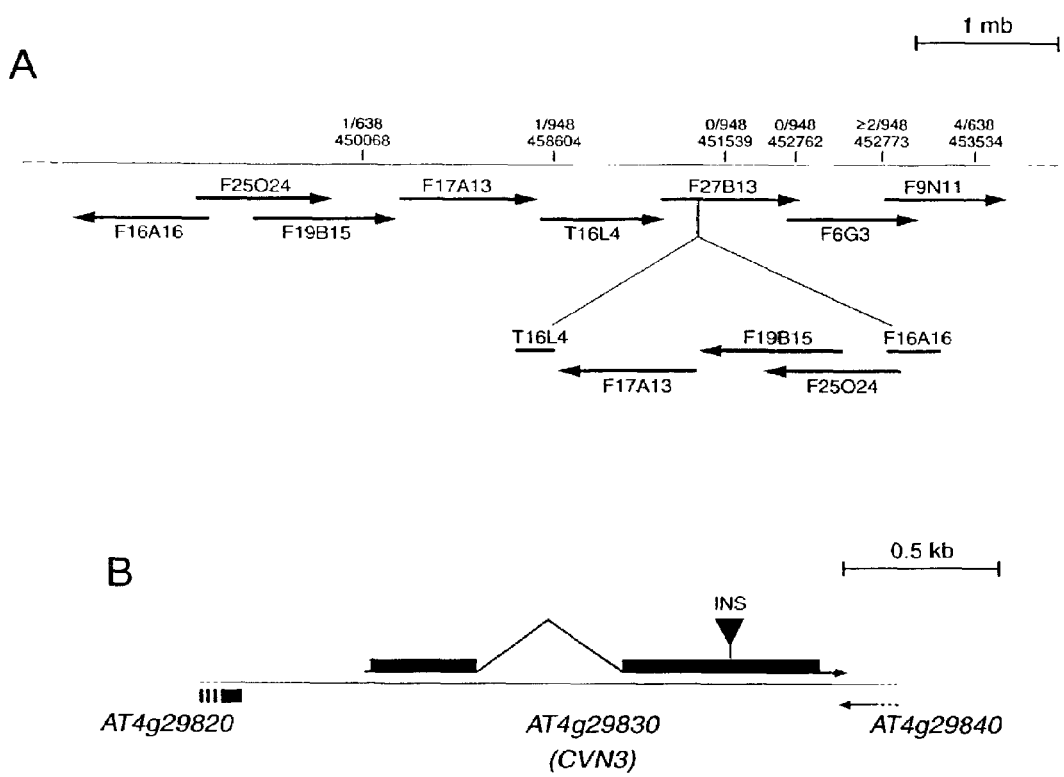
FIG. 10 Panel A shows the region of chromosome IV encompassing the VIP3 (CVN3) (At4g29830) gene. Molecular markers used in mapping are shown above, with recombination (recombinations/chromomosome analyzed) between the marker and vip3 (cvn3) mutation identified. The position and orientation of BAC (bacterial artificial chromosome) clones in this region is shown below. The position and presumed extent of the genomic insertion found in the vip3 (cvn3) mutant is indicated. Panel B shows a depiction of the immediate region of the VIP3 (CVN3) gene. Lines with arrows indicate the orientation and extent of RNA transcripts, as determined from analysis of cDNAs present in databases. No cDNAs were identified for At4g29820. Open reading frames as predicted by the AGI are shown as filled rectangles. The position of the insertion in the vip3 (cvn3) mutant is shown (INS). Panel C shows the results of an analysis of VIP3 (CVN3) RNA expression in wild-type (WT) and vip3 (cvn3) mutant plants. RNA was extracted from aerial portions of 14 d-old, wild-type and vip3 (cvn3) seedlings and analyzed by gel blotting using an VIP3 (CVN3) probe as described in Example 3. The membrane was subsequently stripped and reprobed with an actin probe to indicate the integrity and relative quantity of total RNA in each lane.

Through genetic mapping, the vip3 mutation was localized to a ~2.4 mb region of the lower arm of chromosome IV, represented by three overlapping BAC clones (FIG. 10 Panel A). Subsequently, genomic DNA from vip3 and wild-type plants was analyzed by gel blotting using these three BACs as probes. This approach resulted in the indication of an insertion within the predicted coding region of a transcriptional unit designated AT4g29830 by the *Arabidopsis* Genome Initiative (AGI) (FIG. 10 Panel B). Further analysis of the insertion using inverse-PCR and sequencing indicated that it was associated with the translocation of up to ~320 kb, possibly contiguous sequence from a proximal region of chromosome IV (FIG. 10 Panel A). It was observed that in the vip3 mutant, RNAs hybridizing with a AT4g29830 probe accumulated to detectable levels, but were shorter than those seen in wild-type plants, suggesting that the insertion in the vip3 mutant resulted in a truncation of the AT4g29830 gene (FIG. 10 Panel C). RNA expression of the AT4g29840 gene, which is the adjacent gene nearest the insertion site, did not differ greatly between vip3 and wild-type. A query of *Arabidopsis* expressed sequence tag (EST) databases resulted in the identification of six independent cDNAs corresponding to the AT4g29830 gene. These cDNAs collectively defined a transcribed region and intron/exon structure that is consistent with that predicted by the AGI, and with the size of AT4g29830 RNAs as determined by gel blotting. RNA gel blot analysis indicated that AT4g29830 is expressed throughout the plant, and is most abundant in the shoot apical tissues, which is consistent with the origin of the ESTs from different tissues.

To determine if disruption of AT4g29830 was the lesion causing the vip phenotype, molecular complementation was performed in transgenic plants using a ~6.4-kb DNA containing the entire AT4g29830 transcriptional unit. Because the vip3 mutant is predominately male-sterile, the transgene was first introduced into wild-type plants, and then introduced the transgene into the vip3 mutant through crossing. Several independent lines were generated that were homozygous for the translocation mutation, and contained at least one copy of the VIP3 transgene. These plants were phenotypically indistinguishable from wild-type plants, flowering extremely late in the absence of cold, and producing morphologically normal flowers. Based on these data, and the observation that antisense expression and apparent cosuppression of AT4g29830 resulted in a partial phenocopy of the vip phenotype (below), it was concluded that AT4g29830 is the VIP3 gene.

Based on annotation provided by the AGI, VIP3 encodes a 321-amino acid protein that is composed almost entirely of seven repeats of a motif designated the Trp-Asp (WD) motif (also known as the WD-40 repeat; Neer et al., (1994) Nature 371, 297-300; Smith et al., (1999) Trends Biochem Sci 24, 181-185) (FIG. 11). The predicted VIP3 protein does not show extensive sequence homology with any protein cataloged in current protein databases. However, several known and predicted proteins exhibit an overall structure similar to VIP3, with seven tandem WD repeats and no extensive amino-terminal or carboxyl-terminal extensions. These include the Gβ subunit of heterotrimeric GTP-binding proteins (FIG. 11).

Constitutive and Antisense Expression of VIP3 in Transgenic Plants.

To study the potential effects of manipulated expression of VIP3 on growth and development, transgenic plants were engineered in which the genomic copy of VIP3 was expressed in either sense or antisense orientation, under control of the constitutive CaMV 35S promoter. For both the sense (35S: VIP3) and antisense (VIP3-AS) strategies, at least 150 transgenic plants were recovered.

For the VIP3-AS strategy, self-pollinated offspring from infiltrated plants (designated T1 plants) were grown without a vernalizing cold treatment. Approximately one-half of VIP3-AS plants surviving selection flowered very early, with as few as five rosette leaves. In contrast, nonvernalized, wild-type Col:FRI$^{SF2}$ grown under similar conditions produced at least 60 rosette leaves without flowering. In addition, the typical early-flowering VIP3-AS plants exhibited reduced apical dominance, and produced small leaves and morphologically-abnormal flowers similar to vip3 flowers.

For the 35S: VIP3 strategy, a population of T1 plants was grown without a vernalizing cold treatment. Several of plants flowered, with the earliest of these flowering with 10 rosette leaves. In these early-flowering 35S: VIP3 plants, leaf size, apical dominance, and floral morphology were not greatly affected. Neither VIP3 nor FLC RNAs were detectable in leaf tissues of these plants by gel blotting, suggesting that early flowering resulted from decreased VIP3 expression. The remainder of the 35S: VIP3 population did not flower during the course of this experiment. Analysis of VIP3 mRNA levels in leaf tissues from several of the nonflowering plants indicated that VIP3 was expressed to high levels in the leaves relative to wild-type, nontransgenic plants. To determine if this ectopic expression of VIP3 was sufficient to activate FLC, FLC RNA levels were analyzed by gel blotting, and the results indicated that FLC was not expressed to higher levels in leaves of 35S: VIP3 plants relative to wild-type plants.

To determine if constitutive expression of VIP3 could overcome the repressive effect of cold on FLC expression, another population of 35S: VIP3 TI plants grown after being subjected to a vernalizing cold treatment was analyzed. In this population of approximately 250 individuals, all plants flowered very early, and there was no large variation in flowering time among the plants. Analysis by gel blotting of leaf tissues indicated that VIP3 was expressed to high levels in several of these plants. In these VIP3-expressing plants, however, FLC expression was not detectable, indicating that VIP3 is probably insufficient to activate FLC in vernalized plants.

It was also observed that VIP3 RNA was expressed to similar levels in seedling tissues of Col plants (lacking activity of FRI), ld-1 mutant plants (in the Col genetic background, lacking activity of FRI and severely compromised for LD activity) and wild-type Col:FRI$^{SF2}$ plants. In these experiments, the expression of VIP3 RNA in aerial portions of 14 d-old Columbia (Col), wild-type (Col:FRI$^{SF2}$), and ld-1 (Col:ld-1) seedlings grown without a cold treatment under short-day (SD) photoperiods. RNAs were analyzed by gel blotting using VIP3 and FLC probes. The blot was subsequently stripped and reprobed with an actin probe to indicate the integrity and relative quantity of RNA in each lane. The lack of effect of disruption of FRI or the autonomous pathway on VIP3 RNA expression suggests that modulation of VIP3 expression is unlikely to be involved in the regulation of FLC by FRI or the autonomous pathway, unless modulation of VIP3 expression occurs mostly at the protein level, or within a restricted subset of tissues.

VIP3 is a Member of a Family of Functionally-Related Genes in *Arabidopsis*.

The phenotype of the vip3 mutant is similar to that of plants with mutations in the previously identified gene VIP4 (as described above). For example, vip4 mutants flower very early, do not express detectable levels of FLC, and exhibit reduced apical dominance. In addition, vip4 plants exhibit defects in floral morphology that are similar to those of vip3, albeit weaker. Two additional vip3-like plants were identified in the fast-neutron-mutagenized population that were not allelic to vip3 or vip4. These findings suggest that a family of genes exist in *Arabidopsis* that function in a non-redundant manner to regulate a defined subset of developmental events, including flowering. To define the extent of this gene family, extensive mutagenesis and screenings were performed. This resulted in the identification of 6 additional, vip3/vip4-like mutants. Five additional mutants were recovered in separate screenings by R. Amasino (University of Wisconsin) and generously provided for analyses. All of the respective mutations were mapped to within a ~10 cM region of the genome, and those plants harboring mutations at similar positions were subjected to complementation analysis. This resulted in the identification of six complementation groups, of which two represented VIP3 and VIP4 (Table 1). When evaluated in SD conditions in the absence of cold, all of the mutants were early flowering to a similar degree, and analysis of FLC RNA levels in the mutants indicated that in all cases this early flowering was associated with loss of FLC expression. In addition, all mutants showed similar defects in leaf size, apical dominance, and floral morphology. None of the mutations map to previously described flowering time genes, with the exception of VIP2, which is located within a broad region described for early-flowering in short days (efs) (Soppe et al., (1999) Development 126, 4763-4770).

TABLE 1

Genetic mapping of VIP gene family members in Arabidopsis, showing the approximate map positions of the VIP loci. The molecular markers used, and recombination between the mutation and the marker (recombinations/chromosomes analyzed) are indicated.

| LOCUS | Alleles | Chromosome | Map Position |
| --- | --- | --- | --- |
| VIP1 | 1 | I | nga280 (0/100) |
| VIP2 | 1 | I | nga111 (11/118) |
| VIP3 | 1 | IV | cloned |
| VIP4 | 3 | V | cloned |
| VIP5 | 1 | I | cloned |
| VIP6 | 3 | II | cloned |
| VIP7 | 1 | v | ciw10 (10/136) |

The relationship between VIP3 and VIP4 by was analyzed by genetic and molecular epistasis experiments. In a vip3 mutant background, VIP4 RNA was expressed to levels similar to that seen in wild-type plants. Likewise, in a genetic background containing the vip4-1 allele, there was no apparent difference in VIP3 RNA expression as compared with wild-type plants. When evaluated under long-day growth conditions, there was no apparent additional defect in flowering time or floral morphology conferred by loss of VIP3 activity in a vip4-1 mutant background. Although it is not necessary to understand the underlying mechanism to practice the invention, and it is not intended that the invention be limited to any particular hypothesis or theory, it is contemplated from the results that VIP3 and VIP4 function as indispensable components of a common mechanism.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

The invention claimed is:

1. An isolated nucleic acid sequence comprising an exogenous promoter operably linked to a nucleic acid sequence encoding a vernalization independence polypeptide comprising SEQ ID NO:5, wherein said vernalization independence polypeptide is VIP3, wherein said polypeptide alters flowering phenotype in a plant.

2. An isolated nucleic acid sequence comprising an exogenous promoter operably linked to a nucleic acid sequence encoding a vernalization independence polypeptide encoded by SEQ ID NO:1, wherein said polypeptide alters flowering phenotype in a plant.

* * * * *